US009567607B2

(12) United States Patent
Wilson et al.

(10) Patent No.: US 9,567,607 B2
(45) Date of Patent: *Feb. 14, 2017

(54) ADENO-ASSOCIATED VIRUS SEROTYPE I NUCLEIC ACID SEQUENCES, VECTORS AND HOST CELLS CONTAINING SAME

(71) Applicant: The Trustees of the University of Pennsylvania, Philadelphia, PA (US)

(72) Inventors: James M. Wilson, Glen Mills, PA (US); Weidong Xiao, Fort Washington, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/849,722

(22) Filed: Sep. 10, 2015

(65) Prior Publication Data

US 2015/0376649 A1 Dec. 31, 2015

Related U.S. Application Data

(60) Continuation of application No. 14/136,331, filed on Dec. 20, 2013, now Pat. No. 9,163,260, which is a continuation of application No. 13/048,936, filed on Mar. 16, 2011, now Pat. No. 8,637,255, which is a continuation of application No. 12/617,967, filed on Nov. 13, 2009, now abandoned, which is a continuation of application No. 11/893,697, filed on Aug. 17, 2007, now abandoned, which is a continuation of application No. 11/708,785, filed on Feb. 20, 2007, now abandoned, which is a continuation of application No. 10/696,900, filed on Oct. 30, 2003, now Pat. No. 7,186,552, which is a continuation of application No. 09/807,802, filed as application No. PCT/US99/25694 on Nov. 2, 1999, now Pat. No. 6,759,237, said application No. 11/893,697 is a continuation of application No. 11/430,226, filed on May 8, 2006, now abandoned, which is a division of application No. 10/696,282, filed on Oct. 29, 2003, now Pat. No. 7,105,345, which is a division of application No. 09/807,802, filed as application No. PCT/US99/25694 on Nov. 2, 1999, now Pat. No. 6,759,237.

(60) Provisional application No. 60/107,114, filed on Nov. 5, 1998.

(51) Int. Cl.
| | |
|---|---|
| C12N 15/11 | (2006.01) |
| C12N 15/86 | (2006.01) |
| C07K 14/005 | (2006.01) |
| C07K 14/505 | (2006.01) |
| C07K 14/81 | (2006.01) |
| C12N 7/00 | (2006.01) |

(52) U.S. Cl.
CPC ............ *C12N 15/86* (2013.01); *C07K 14/005* (2013.01); *C07K 14/505* (2013.01); *C07K 14/8125* (2013.01); *C12N 7/00* (2013.01); *C12N 2750/14121* (2013.01); *C12N 2750/14143* (2013.01); *C12N 2799/025* (2013.01)

(58) Field of Classification Search
CPC .................. C12N 15/86; C12N 2750/14121; C12N 2750/14132
See application file for complete search history.

(56) References Cited

U.S. PATENT DOCUMENTS

| | | | |
|---|---|---|---|
| 5,139,941 | A | 8/1992 | Muzyczka et al. |
| 5,252,479 | A | 10/1993 | Srivastava et al. |
| 5,436,146 | A | 7/1995 | Shenk et al. |
| 5,478,745 | A | 12/1995 | Samulski et al. |
| 5,589,377 | A | 12/1996 | Lebkowski et al. |
| 5,622,856 | A | 4/1997 | Natsoulis et al. |
| 5,658,785 | A | 8/1997 | Johnson |
| 5,681,731 | A | 10/1997 | Lebkowski et al. |
| 5,753,500 | A | 5/1998 | Shenk et al. |
| 5,756,283 | A | 5/1998 | Wilson et al. |
| 5,773,289 | A | 6/1998 | Samulski et al. |
| 5,780,280 | A | 7/1998 | Lebkowski et al. |
| 5,780,447 | A | 7/1998 | Nienhuis |
| 5,786,211 | A | 7/1998 | Johnson |
| 5,834,441 | A | 11/1998 | Philip et al. |
| 5,843,742 | A | 12/1998 | Natsoulis et al. |
| 5,846,528 | A | 12/1998 | Podsakoff et al. |
| 5,846,546 | A | 12/1998 | Hurwitz et al. |
| 5,856,152 | A | 1/1999 | Wilson et al. |
| 5,858,351 | A | 1/1999 | Podsakoff et al. |
| 5,858,775 | A | 1/1999 | Johnson |
| 5,861,171 | A | 1/1999 | Philip et al. |
| 5,861,314 | A | 1/1999 | Philip et al. |
| 5,863,541 | A | 1/1999 | Samulski et al. |
| 5,866,552 | A | 2/1999 | Wilson et al. |

(Continued)

FOREIGN PATENT DOCUMENTS

| | | |
|---|---|---|
| AU | 199942205 | 6/2003 |
| WO | WO 95/28493 | 10/1995 |

(Continued)

OTHER PUBLICATIONS

Anderson, et al., "Human gene therapy", Nature, vol. 392, pp. 25-30, Apr. 30, 1998.
Arruda, et al., "Safety and Efficacy of Factor IX Gene Transfer to Skeletal Muscle in Murine and Canine Hemophilia B Models by Adeno-Associated Viral Vector Serotype 1," Blood First Edition Paper (Sep. 11, 2003).
Balague, et al., "Adeno-Associated Virus Rep78 Protein and Terminal Repeats Enhance Integration of DNA Sequences into the Cellular Genome," Journal of Virology, vol. 71 No. 4:3299-3306, (Apr. 1997).
Bartlett, et al., "Genetics and biology of adeno-associated virus," Viral Vectors, Chapter 4, pp. 55-73, (1995).

(Continued)

*Primary Examiner* — Brian Whiteman
(74) *Attorney, Agent, or Firm* — Howson & Howson LLP

(57) ABSTRACT

The nucleic acid sequences of adeno-associated virus (AAV) serotype 1 are provided, as are vectors and host cells containing these sequences and functional fragments thereof. Also provided are methods of delivering genes via AAV-1 derived vectors.

17 Claims, 13 Drawing Sheets

(56) References Cited

U.S. PATENT DOCUMENTS

| | | |
|---|---|---|
| 5,866,696 A | 2/1999 | Carter et al. |
| 5,869,305 A | 2/1999 | Samulski et al. |
| 5,871,982 A | 2/1999 | Wilson et al. |
| 5,872,005 A | 2/1999 | Wang et al. |
| 5,874,304 A | 2/1999 | Zolotukhin et al. |
| 5,874,556 A | 2/1999 | Lupton et al. |
| 5,882,652 A | 3/1999 | Valdes et al. |
| 5,905,040 A | 5/1999 | Mazzara et al. |
| 5,916,563 A | 6/1999 | Young et al. |
| 5,922,315 A | 7/1999 | Roy |
| 5,945,335 A | 8/1999 | Colosi |
| 5,952,221 A | 9/1999 | Kurtzman et al. |
| 5,962,274 A | 10/1999 | Parks |
| 5,962,313 A | 10/1999 | Podsakoff et al. |
| 6,001,371 A | 12/1999 | Young et al. |
| 6,027,931 A | 2/2000 | Natsoulis et al. |
| 6,033,885 A | 3/2000 | Latta et al. |
| 6,093,392 A | 7/2000 | High et al. |
| 6,156,303 A | 12/2000 | Russell et al. |
| 6,207,457 B1 | 3/2001 | Natsoulis et al. |
| 6,251,677 B1 | 6/2001 | Wilson et al. |
| 6,258,595 B1 | 7/2001 | Gao et al. |
| 6,274,354 B1 | 8/2001 | Wilson et al. |
| 6,365,394 B1 | 4/2002 | Gao et al. |
| 6,387,368 B1 | 5/2002 | Wilson et al. |
| 6,399,385 B1 | 6/2002 | Croyle et al. |
| 6,468,524 B1 | 10/2002 | Chiorini et al. |
| 6,475,769 B1 | 11/2002 | Wilson et al. |
| 6,482,634 B1 | 11/2002 | Wilson et al. |
| 6,491,907 B1 | 12/2002 | Rabinowitz |
| 6,521,225 B1 | 2/2003 | Srivastava et al. |
| 6,759,237 B1 | 7/2004 | Wilson et al. |
| 6,953,690 B1 | 10/2005 | Gao et al. |
| 6,984,517 B1 | 1/2006 | Chiorini et al. |
| 7,105,345 B2 | 9/2006 | Wilson et al. |
| 7,172,893 B2 | 2/2007 | Rabinowitz et al. |
| 7,186,552 B2 | 3/2007 | Wilson et al. |
| 7,252,997 B1 | 8/2007 | Hallek et al. |
| 8,637,255 B2 | 1/2014 | Wilson et al. |
| 8,734,809 B2 | 5/2014 | Gao et al. |
| 2002/0159978 A1 | 10/2002 | Allen |
| 2003/0215422 A1 | 11/2003 | Chiorini et al. |
| 2004/0057931 A1 | 3/2004 | Wilson et al. |
| 2004/0057932 A1 | 3/2004 | Wilson et al. |
| 2004/0057933 A1 | 3/2004 | Wilson et al. |
| 2004/0086490 A1 | 5/2004 | Chiorini et al. |
| 2005/0255089 A1 | 11/2005 | Chiorini et al. |
| 2006/0188483 A1 | 8/2006 | Rabinowitz et al. |
| 2006/0188484 A1 | 8/2006 | Rabinowitz et al. |
| 2006/0204479 A1 | 9/2006 | Wilson et al. |
| 2008/0050343 A1 | 2/2008 | Wilson et al. |
| 2008/0050345 A1 | 2/2008 | Wilson et al. |

FOREIGN PATENT DOCUMENTS

| | | |
|---|---|---|
| WO | WO 96/13598 | 5/1996 |
| WO | WO 96/36364 | 11/1996 |
| WO | WO 97/05266 | 2/1997 |
| WO | WO 97/38723 | 10/1997 |
| WO | WO 98/09524 | 3/1998 |
| WO | WO 98/10086 | 3/1998 |
| WO | WO 98/10088 | 3/1998 |
| WO | WO 98/11244 | 3/1998 |
| WO | WO 98/32842 | 7/1998 |
| WO | WO 98/41240 | 9/1998 |
| WO | WO 99/14354 | 3/1999 |
| WO | WO 99/15677 | 4/1999 |
| WO | WO 99/15685 | 4/1999 |
| WO | WO 99/47691 | 9/1999 |
| WO | WO 99/67393 | 12/1999 |
| WO | WO 00/28061 | 5/2000 |
| WO | WO 00/55342 | 9/2000 |
| WO | WO 00/75353 | 12/2000 |
| WO | WO 01/05991 | 1/2001 |
| WO | WO 01/23001 | 4/2001 |
| WO | WO 01/23597 | 4/2001 |
| WO | WO 01/40455 | 6/2001 |
| WO | WO 01/83692 | 11/2001 |
| WO | WO 02/063025 | 8/2002 |
| WO | WO 03/092598 | 11/2003 |
| WO | WO 03/093440 | 11/2003 |

OTHER PUBLICATIONS

K. Berns, "Parvovirus Replication," Microbiological Reviews, vol. 54 No. 3:316-329, Sep. (1990).

K. Berns, "Parvoviridae: The Viruses and Their Republication, in B. N. Fields et al, Fields Virology, 3rd ed.," vol. 2, Chapter 69, pp. 2173-2197 (Lippincott-Raven Publishers, Philadelphia, PA) (1996).

Boyer, et al., "Anti-SARS Humoral and Cellular Immunity Evoked by Adenovirus Vector Expressing Spike Glycoprotein from SARS Coronavirus," Abstract 558, 7th Annual Meeting of the American Society of Gene Therapy, (Jun. 2-6, 2004; e-publ. May 2, 2004).

Brown, et al., "Chimeric parvovirus B19 capsids for the presentation of foreign epitopes," Virology, vol. 198, No. 2, pp. 477-488 (Feb. 1994).

Chao, et al., "Several Log Increase in Therapeutic Transgene Delivery by Distinct Adeno-Associated Viral Serotype Vectors," Molecular Therapy, vol. 2, No. 6:619-623 (Dec. 2000).

Chapman, et al., "Structure, sequence, and function correlations among parvoviruses," Virology, vol. 194, No. 2, pp. 491-508 (Jun. 1993).

Chiorini, et al., "Cloning of Adeno-Associated Virus Type 4 (AAV4) and Generation of Recombinant AAV4 Particles, Journal of Virology," vol. 71, No. 9:6823-6833 (Sep. 1997).

Fisher, et al., "Recombinant Adeno-Associated Virus for Muscle Directed Gene Therapy," Nature Medicine, vol. 3, No. 3:306-312 (Mar. 1997).

Flotte, et al., "An improved system for packaging recombinant adeno-associated virus vectors capable of in vivo transduction," Gene Therapy, vol. 2, No. 1:29-37 (Jan. 1995).

Gao, et al., "High-titer adeno-associated viral vectors from a Rep/Cap cell line and hybrid shuttle virus," Human Gene Therapy, vol. 9, No. 16: 2353-2362 (Nov. 1, 1998).

Gao, et al., "Erythropoietin Gene Therapy Leads to Autoimmune Anemia in Macaques," Blood, vol. 103, No. 9 (May 1, 2004) pp. 3300-2.

Gao, et al., "Clades of Adeno-Associated Viruses are Widely Disseminated in Human Tissues," Journal of Virology, vol. 78, No. 9 (May 1, 2004), pp. 6381-8.

Hauck, et al., "Characterization of Tissue Tropism Determinants of Adeno-Associated Virus Type 1," Journal of Virology, vol. 77, No. 4: 2768-2774 (Feb. 2003).

Hauck, et al., "Generation and Characterization of Chimeric Recombinant AAV Vectors," Molecular Therapy, vol. 7, No. 3:419-425 (Mar. 2003).

Kotin, et al., "Site-Specific Integration by Adeno-Associated Virus," Proc. Natl. Acad. Sci. USA, vol. 87:2211-2215 (Mar. 1990).

Muramatsu, et al., "Nucleotide Sequencing and Generation of an Infectious Clone of Adeno-Associated Virus 3," Virology, vol. 221:208-217 (1996).

N. Muzyczka, "Use of Adeno-Assicated Virus as a General Transduction Vector for Mammalian Cells, Current Topics in Microbiology and Immunology," vol. 158:97-129 (1992).

Orkin, et al., "Report and Recommendations of the Panel to Assess the NIH Investments in Research on Gene Therapy," Issue by the National Institute of Health, (Dec. 7, 1995).

Rabinowitz, et al., "Cross-Packaging of a Single Adeno-Associated Virus (AAV) Type 2 Vector Genome into Multiple AAV Serotypes Enables Transduction with Broad Specificity," Journal of Virology, vol. 76, No. 2: 791-801(Jan. 2002).

Rick, et al., "Congenital Bleeding Disorders," American Society of Hematology: 559-574 (Jan. 1, 2003).

Rose, et al., "Nucleic Acid from an Adeno-Associated Virus: Chemical and Physical Studies," Microbiology, vol. 546: 86-92, (1966).

Rutledge, et al., "Infectious clones and vectors derived from adeno-associated virus (AAV) serotypes other than AAV type 2," Journal of Virology, vol. 72, No. 1: 309-19 (Jan. 1998).

(56) References Cited

OTHER PUBLICATIONS

Samulski, et al., "Helper-free stocks of recombinant adeno-associated viruses: normal integration does not require viral gene expression," Journal of Virology, vol. 63, No. 9: 3822-3828 (Sep. 1989).
Samulski, et al., "Cloning of Adeno-Associated Virus into pBR322: Rescue of Intact Virus from the Recombinant Plasmid in Human Cells," Proc. Natl. Acad. Sci. USA, vol. 79:2077-2081 (Mar. 1982).
Samulski, et al., "Targeted Integration of Adeno-Associated Virus (AAV) into Human Chromosome 19," EMBO Journal, vol. 10, No. 12:3941-3950 (Dec. 1991).
Snyder, et al., "Features of the Adeno-Associated Virus Origin Involved in Substrate Recognition by the Viral Rep Protein," Journal of Virology, vol. 67, No. 10:6096-6104 (Oct. 1993).
Snyder, et al., "Persistent and Therapeutic Concentrations of Human Factor IX in Mice After Hepatic Gene Transfer of Recombinant AAV Vectors," Nature Genetics, vol. 16:270-276 (Jul. 1997).
Srivastava, et al., "Construction of a recombinant human parvovirus B19: adeno-associated virus 2 (AAV) DNA inverted terminal repeats are functional in an AAV-B19 hybrid virus," Proceeding of the National Academy of Sciences of the United States of America, vol. 86, No. 20: 8078-8082 (Oct. 1989).
Surace, et al., "Delivery of Adeno-Associated Virus Vectors to the Fetal Retina: Impact of Viral Capsid Proteins on Retinal Neuronal Progenitor Transduction," Journal of Virology, vol. 77, No. 14: 7957-7963 (Jul. 2003).
Surosky, et al., "Adeno-Associataed Virus Rep Proteins Target DNA Sequences to a Unique Locus in the Human Genome," Journal of Virology, vol. 71, No. 10:7951-7959 (Oct. 1997).
Verma, et al., "Gene therapy—promises, problems and prospects," Nature, vol. 389, pp. 239-242 (Sep. 18, 1997).
Wang, et al., "Rescue and replication of adeno-associated virus type 2 as well as vector DNA sequences from recombinant plasmids containing deletions in the viral inverted terminal repeats: selective encapsidation of viral genomes in progeny virions," Journal of Virology, vol. 70, No. 3: 1668-1677 (Mar. 1996).
Wu, et al., "Mutational analysis of the adeno-associated virus type 2 (AAV2) capsid gene and construction of AAV2 vectors with altered tropism," Journal of Virology, vol. 74, No. 18: 8635-8647 (Sep. 2000).
W. Xiao, et al., "Gene Therapy Vecotrs Based on Adeno-Associated Virus Type 1," Journal of Virology, vol. 73, No. 5:3994-4003 (May 1999).
X. Xiao, et al., "Efficient Long-Term Gene Transfer into Muscle Tissue of Immunocompetent Mice by Adeno-Associataed Virus Vector," Journal of Virology, vol. 70, No. 11:8098-8108 (Nov. 1996).
X. Xiao, et al., "Gene Transfer by Adeno-Associated Virus Vectors into the Central Nervous System," Experimental Neurology, vol. 144:113-124 (Mar. 1997).
Zhi, et al., "Increased Antigen-Specific Humoral Response by Adenoviral Vector Prime and Adeno-Associated Viral Vector Boost, Abstract 569," 7th Annual Meeting of the American Society of Gene Therapy, Minneapolis Minnesota, (Jun. 2-6, 2004; e-publ. May 2, 2004).
Lackner and Muzyczka, Studies of the Mechanism of Transactivation of the Adeno-Associated Virus p19 Promoter by Rep Protein, J. Virology, Aug. 2002, pp. 8225-8235, vol. 76, No. 16.
McCarty, et al., Sequences Required for Coordinate Induction of Adeno-Associated Virus p19 and p40 Promoters by Rep Protein, Journal of Virology, Jun. 1991, pp. 2936-2945, vol. 65, No. 6.

FIG. 1A

```
AAV-1  ttgcccactccctctctgcgcgctcgctcgctcggtggggcctgcggaccaaaggtccgc    60
AAV-2  ...g........................ac..a....g.gc............gc.       60
AAV-6  ...g........................ac..a....g.gc............gc.       60

Rep binding site
AAV-1  agacggcagagctctgctctgccggccc caccgagcgagcgagcgcgcag agagggagtg  120
AAV-2  c....c.c.g...t...c.g.g.....t ..gt...................  ........  120
AAV-6  c....c.c.g...t...c.g.g.....t ..gt...................  ........  120

TRS
AAV-1  ggcaactccatcactaggggtaaTCGCGAAGCGCCTCCCACGCTGCCGCGTCAGCGCTGA    180
AAV-2  .c..................--..ct.G..G.------------.TG.A...G----...   163
AAV-6  .c..................--..ct.G..G.------------.TG.A...G----...   163

E box/USF
AAV-1  CGTAAATTACGTCATAGGG---GAGTGGTCCTGTATTAGCT GTCACGTG AGTGCTTTTGC  237
AAV-2  ...G...............TTA.G.A..........AG   ........ ....-......  222
AAV-6  ...G...............TTA.G.A..........AG   ........ ....-......  222

YY1                         P5/TATA
AAV-1  GACATTTTGCGACACCACGTGGCCATTTAGGGTATATATGGCCGAGTGAGCGAGCAGGAT    297
AAV-2  ................T....T..CGCT......T..A.C..........AC.....G.   282
AAV-6  ................T....T..CGCT......T..A.C..........AC.....G.   282

YY1/p5 RNA                   Rep 78/68
AAV-1  CTCCATTTTGAC-CGCGAAATTTGAACGAGCAGCAGCCATGCCGGGCTTCTACGAGATCG    356
AAV-2  ..........AG..G..GG........C.....C............G..T........T.   342
AAV-6  ..........AG..G..GG........C.....-............G..T........T.   341

AAV-1  TGATCAAGGTGCCGAGCGACCTGGACGAGCACCTGCCGGGCATTTCTGACTCGTTTGTGA    416
AAV-2  ....T.....C..C........T....G...T.....C............AGC.......   402
AAV-6  ....T.....C..C........T........T.....C............AGC.......   401

AAV-1  GCTGGGTGGCCGAGAAGGAATGGGAGCTGCCCCGGATTCTGACATGGATCTGAATCTGA    476
AAV-2  A........................T....G..A........................   462
AAV-6  A........................T....G..A........................   461

AAV-1  TTGAGCAGGCACCCCTGACCGTGGCCGAGAAGCTGCAGCGCGACTTCCTGGTCCAATGGC    536
AAV-2  ..........................................T...ACGG......     522
AAV-6  ...........................................G....              521

AAV-1  GCCGCGTGAGTAAGGCCCCGGAGGCCCTCTTCTTTGTTCAGTTCGAGAAGGGCGAGTCCT    596
AAV-2  ....T.....................T........G..A..T........A...AG..   582
AAV-6  ............................................................   581

AAV-1  ACTTCCACCTCCATATTCTGGTGGAGACCACGGGGGTCAAATCCATGGTGCTGGGCCGCT    656
AAV-2  .........A.G..CG.G..C.....A.....C.....G..........TT....A..T.   642
AAV-6  ............................................................   641

AAV-1  TCCTGAGTCAGATTAGGGACAAGCTGGTGCAGACCATCTACCGCGGGATCGAGCCGACCC    716
AAV-2  ..........C.C..A..A...A.T....GA..T....................TT      702
AAV-6  ............................................................   701

AAV-1  TGCCCAACTGGTTCGCGGTGACCAAGACGCGTAATGGCGCCGGAGGGGGGAACAAGGTGG    776
AAV-2  ....A.........C..A.....CA.A.............C...........          762
AAV-6  ............................................................   761
```

FIG. 1B

```
            TGGACGAGTGCTACATCCCCAACTACCTCCTGCCCAAGACTCAGCCCGAGCTGCAGTGGG
AAV-1       TGGACGAGTGCTACATCCCCAACTACCTCCTGCCCAAGACTCAGCCCGAGCTGCAGTGGG  836
AAV-2       ....T................T...T.G..C.....A..C.....T.....C.......  822
AAV-6       ............................................................  821

P19/TATA              P19 RNA
AAV-1       CGTGGACTAACATGGAGGAGTATATAAGCGCCTGTTTGAACCTGGCCGAGCGCAAACGGC  896
AAV-2       ..........T.....AC.....T.......C.....G..T..CA.G.....T......T  882
AAV-6       ..........C.....GG.....A.......G.....A..C..GG.C.............  881

AAV-1       TCGTGGCGCAGCACCTGACCCACGTCAGCCAGACCCAGGAGCAGAACAAGGAGAATCTGA  956
AAV-2       .G............T.....G.....GTCG.....G..............A.......A..  942
AAV-6       ..........CG................................................  941

Rep_52/40
AAV-1       ACCCCAATTCTGACGCGCCTGTCATCCGGTCAAAAACCTCCGCGCGCTACATGGAGCTGG 1016
AAV-2       .T............T.....G..G...A.A........T..A..CA.G............ 1002
AAV-6       ..............................................A............ 1001

AAV-1       TCGGGTGGCTGGTGGACCGGGGCATCACCTCCGAGAAGCAGTGGATCCAGGAGGACCAGG 1076
AAV-2       ..........C......AA...G..T.....G............................ 1062
AAV-6       ............................................................ 1061

AAV-1       CCTCGTACATCTCCTTCAACGCCGCTTCCAACTCGCGGTCCCAGATCAAGGCCGCTCTGG 1136
AAV-2       ....A................T..G..C..................A........T..CT... 1122
AAV-6       ............................................................ 1121

AAV-1       ACAATGCCGGCAAGATCATGGCGCTGACCAAATCCGCGCCCGACTACCTGGTAGGCCCCG 1196
AAV-2       .......G..A.....T...AGC.....T...A....C..............G....AGC 1182
AAV-6       ............................................................ 1181

AAV-1       CTCCGCCCGCGGACATTAAAACCAACCGCATCTACCGCATCCTGGAGCTGAACGGCTACG 1256
AAV-2       AG..CGTG.A.......TCC.G...T..G..T..TAAA..TT....A..A.....G.... 1242
AAV-6       ..........C....................T............................ 1241

AAV-1       AACCTGCCTACGCCGGCTCCGTCTTTCTCGGCTGGGCCCAGAAAAGGTTCGGGAAGCGCA 1316
AAV-2       .T..CCAA..T..G.CT...........G..A......AC.....A......C...A.G. 1302
AAV-6       .C............................................A..A.... 1301

AAV-1       ACACCATCTGGCTGTTTGGGCCGGCCACCACGGGCAAGACCAACATCGCGGAAGCCATCG 1376
AAV-2       ....................T..A..T..C..G..............G.....A. 1362
AAV-6       ............................................................ 1361

AAV-1       CCCACGCCGTGCCCTTCTACGGCTGCGTCAACTGGACCAATGAGAACTTTCCCTTCAATG 1436
AAV-2       .....A.T............G.....A.........................C. 1422
AAV-6       .......................................................C. 1421

AAV-1       ATTGCGTCGACAAGATGGTGATCTGGTGGGAGGAGGGCAAGATGACGGCCAAGGTCGTGG 1496
AAV-2       .C..T.........................G........C............ 1482
AAV-6       ............................................................ 1481

AAV-1       AGTCCGCCAAGGCCATTCTCGGCGGCAGCAAGGTGCGCGTGGACCAAAAGTGCAAGTCGT 1556
AAV-2       ....G.....A..........A..A................G..A........C. 1542
AAV-6       ............................................................ 1541

AAV-1       CCGCCCAGATCGACCCCACCCCCGTGATCGTCACCTCCAACACCAACATGTGCGCCGTGA 1616
AAV-2       .G.......A.....G..T......................................... 1602
AAV-6       ............T................................................ 1601
```

FIG. 1C

```
AAV-1 TTGACGGGAACAGCACCACCTTCGAGCACCAGCAGCCGTTGCAGGACCGGATGTTCAAAT 1676
AAV-2 ............TCA..G........A....................A............... 1662
AAV-6 ............................................................. 1661

AAV-1 TTGAACTCACCCGCCGTCTGGAGCATGACTTTGGCAAGGTGACAAAGCAGGAAGTCAAAG 1740
AAV-2 ......................T..........G.....C..C................ 1722
AAV-6 ............................................................. 1721

AAV-1 AGTTCTTCCGCTGGGCGCAGGATCACGTGACCGAGGTGGCGCATGAGTTCTACGTCAGAA 1796
AAV-2 .C..T.....G.....AA...........GTT........A......A..........A.. 1782
AAV-6 ............................................................. 1781

P40/TATA
AAV-1 AGGGTGGAGCCAACAAAAGACCCGCCCCCGATGACGCGGATAAAAGCGAGCCCAAGCGGG 1856
AAV-2 .............G...............AG......A....T...T.........A.... 1842
AAV-6 ..............G.............................................. 1841

P40 RNA
AAV-1 CCTGCCCCTCAGTCGCGGATCCATCGACGTCAGACGCGGAAGGAGCTCCGGTGGACTTTG 1916
AAV-2 TGC..GAG.....T...C.G...................---..T..A.CA...AC. 1899
AAV-6 ............................................................. 1901

▼
AAV-1 CCGACAGGTACCAAAACAAATGTTCTCGTCACGCGGGCATGCTTCAGATGCTGTTTCCCT 1976
AAV-2 .A............................T.......AA..T................ 1959
AAV-6 ............................................................. 1961

AAV-1 GCAAGACATGCGAGAGAATGAATCAGAATTTCAACATTTGCTTCACGCACGGGACGAGAG 2036
AAV-2 ...GACA..................CA..T..C........T.....ACA..A.. 2019
AAV-6 ....A........................................................C.... 2021

AAV-1 ACTGTTCAGAGTGCTTCCCCGGCGTGTCAGAATCTCAACCGGTC---GTCAGAAAGAGGA 2093
AAV-2 ......T..........T..---.................C..TTCT...GTC..A.A.G 2076
AAV-6 ..........A..T..........................---,............... 2078

AAV-1 CGTATCGGAAACTCTGTGCCATTCATCATCTGCTGGGGCGGGCTCCCGAGATTGCTTGCT 2153
AAV-2 ......A......G..CTA.........A.CA....AAA..TG..A..---C......A 2133
AAV-6 ............................................................. 2138

Rep 78 stop
AAV-1 CGGCCTGCGATCTGGTCAACGTGGACCTGGATGACTGTGTTTCTGAGCAATAAATGACTT 2213
AAV-2 .T.................T.....TT..........CA.C.T...A..........T.. 2193
AAV-6 ..........................T................................. 2193

▽   VP1                          ▽                Rep 68 stop
AAV-1 AAACCAGGTATGGCTGCCGATGGTTATCTTCCAGATTGGCTCGAGGACAACCTCTCTGAG 2273
AAV-2 ...T.......................................CT........A 2253
AAV-6 .........................................AC........G 2258

AAV-1 GGCATTCGCGAGTGGTGGGACTTGAAACCTGGAGCCCCGAAGCCCAAAGCCAACCAGCAA 2333
AAV-2 ..A..AA.AC........A.GC.C........CC.A..ACCA..A...GC..GCAG...GG 2313
AAV-6 ..........................................A................. 2318

AAV-1 AAGCAGGACGACGGCCGGGGTCTGGTGCTTCCTGGCTACAAGTACCTCGGACCCTTCAAC 2393
AAV-2 C.TA........A..A.......T..........G......................... 2373
AAV-6 ............G..C.......G..........C......................... 2378
```

FIG. 1D

```
AAV-1 GGACTCGACAAGGGGGAGCCCGTCAACGCGGCGGACGCAGCGGCCCTCGAGCACGACAAG 2453
AAV-2 ..............A.....G.......A...A.....C....................A 2433
AAV-6 ................................T........................... 2438

AAV-1 GCCTACGACCAGCAGCTCAAAGCGGGTGACAATCCGTACCTGCGGTATAACCACGCCGAC 2513
AAV-2 ..........G.......G.CAGC..A.....C........CAA...C............ 2493
AAV-6 ................A.AGCG..T.....T........GCG...T.............. 2498

AAV-1 GCCGAGTTTCAGGAGCGTCTGCAAGAAGATACGTCTTTTGGGGGCAACCTCGGGCGAGCA 2573
AAV-2 ..G............C..TA................................A...... 2553
AAV-6 ..C............T..GC................................G...... 2558

AAV-1 GTCTTCCAGGCCAAGAAGCGGGTTCTCGAACCTCTCGGTCTGGTTGAGGAAGGCGCTAAG 2633
AAV-2 ..........G..A...A.......T.......G..C............CCT.T.... 2613
AAV-6 ................A...............T.T..................T...... 2618

VP2
AAV-1 ACGGCTCCTGGAAAGAAACGTCCGGTAGAGCAGTCGCCACAAGAGCCAGACTCCTCCTCG 2693
AAV-2 ........G.....A...GA.G...........C..T..TGTG................ 2673
AAV-6 ........T.....G..AC.T...........G..G..ACAA................. 2678

AAV-1 GGCATCGGCAAGACAGGCCAGCAGCCCGCTAAAAAGAGACTCAATTTTGGTCAGACTGGC 2753
AAV-2 ..A.C...A...G.G...........T..A.G...A...T.G................A 2733
AAV-6 .....T...................................................... 2738

AAV-1 GACTCAGAGTCAGTCCCCGATCCACAACCTCTCGGAGAACCTCCAGCAACCCCCGCTGCT 2813
AAV-2 ...G....C.....A..T..C..C..G.........C.G..A......G.....T...G. 2793
AAV-6 ...T....G.....C..C..C..A..A.........G.A..T......A.....G..... 2798

VP3
AAV-1 GTGGGACCTACTACAATGGCTTCAGGCGGTGGCGCACCAATGGCAGACAATAACGAAGGC 2873
AAV-2 C.....A...A...G.....A.....A.........................G... 2853
AAV-6 ............................................................ 2858

AAV-1 GCCGACGGAGTGGGTAATGCCTCAGGAAATTGGCATTGCGATTCCACATGGCTGGGCGAC 2933
AAV-2 ................T....C............................A........ 2913
AAV-6 ............................................................ 2918

AAV-1 AGAGTCATCACCACCAGCACCCGCACCTGGGCCTTGCCCACCTACAATAACCACCTCTAC 2993
AAV-2 ..................A.........C............C............ 2973
AAV-6 ................A..A................T..C............. 2978

AAV-1 AAGCAAATCTCCAGTGCTTCAACGGGGGCCAGCAACGACAACCACTACTTCGGCTACAGC 3053
AAV-2 ..A.....T.....CCAA...---..A...TCG........T........T......... 3030
AAV-6 ............................................................ 3038

AAV-1 ACCCCCTGGGGGTATTTTGATTTCAACAGATTCCACTGCCACTTTTCACCACGTGACTGG 3113
AAV-2 .....T..........C........................................... 3090
AAV-6 ...........................................T..C............ 3098

AAV-1 CAGCGACTCATCAACAACAATTGGGGATTCCGGCCCAAGAGACTCAACTTCAAACTCTTC 3173
AAV-2 ..AA...............C.........A....................G.....T 3150
AAV-6 ............................................G...... 3158

AAV-1 AACATCCAAGTCAAGGAGGTCACGACGAATGATGGCGTCACAACCATCGCTAATAACCTT 3233
AAV-2 .....T........A........CA......C..TACG..G..G..T..C......... 3210
AAV-6 .............................G................... 3218
```

FIG. 1E

```
AAV-1 ACCAGCACGGTTCAAGTCTTCTCGGACTCGGAGTACCAGCTTCCGTACGTCCTCGGCTCT 3293
AAV-2 ...............G..G..TA.T...................C..................G 3270
AAV-6 ..................................T.G........................ 3278

AAV-1 GCGCACCAGGGCTGCCTCCCTCCGTTCCCGGCGGACGTGTTCATGATTCCGCAATACGGC 3353
AAV-2 .....T..A..A........G........A..A.....C......G.G..A..G..T..A 3330
AAV-6 ..............................................G............ 3338

AAV-1 TACCTGACGCTCAACAATGGCAGCCAAGCCGTGGGACGTTCATCCTTTTACTGCCTGGAA 3413
AAV-2 .....C..C..G.....C..G..T..G..A..A.....C..T..A..............G 3390
AAV-6 .....A...................G..A........G..................... 3398

AAV-1 TATTTCCCTTCTCAGATGCTGAGAACGGGCAACAACTTTACCTTCAGCTACACCTTTGAG 3473
AAV-2 ..C..T...............C.T..C..A......................T....... 3450
AAV-6 ........A..G...................T......................C.... 3458

AAV-1 GAAGTGCCTTTCCACAGCAGCTACGCGCACAGCCAGAGCCTGGACCGGCTGATGAATCCT 3533
AAV-2 ..C..T......................T.............T........T..C...... 3510
AAV-6 ..C.......................................................... 3498

AAV-1 CTCATCGACCAATACCTGTATTACCTGAACAGAACTCAAAATCAGTCCGGAAGTGCCCAA 3593
AAV-2 ............G.............T...G......AA.C.C..CAAGT....CCA..ACG 3570
AAV-6 ............G............................G.................. 3578

AAV-1 AACAAGGACTTGCTGTTTAGCCGTGGGTCTCCAGCTGGCATGTCTGTTCAGCCCAAAAAC 3653
AAV-2 C.GTCAAGGC.T.A....TCT.AG.CCGGAG.GAG..A...TCGG.AC...T.T.GG... 3630
AAV-6 .....................G...................................... 3638

AAV-1 TGGCTACCTGGACCCTGTTATCGGCAGCAGCGCGTTTCTAAAACAAAAACAGACAACAAC 3713
AAV-2 .....T............C..C........A..A.CA..G...TCTG.G..T....... 3690
AAV-6 ................C........................................... 3698

AAV-1 AACAGCAATTTTACCTGGACTGGTGCTTCAAAATATAACCTCAATGGGCGTGAATCCATC 3773
AAV-2 .....TG.A.ACT.G........A...A.C..G..CC..........CA.A..C..TC.G 3750
AAV-6 ........C......................................T...........T..A 3758

AAV-1 ATCAACCCTGGCACTGCTATGGCCTCACACAAAGACGACGAAGACAAGTTCTTTCCCATG 3833
AAV-2 G.G..T..G..GC.C..C.....AAGC.....G.....T.....A.....T.....TCA. 3810
AAV-6 .........................................A.................. 3818

AAV-1 AGCGGTGTCATGATTTTTGGAAAAGAGAGCGCCGGAGCTTCAAACACTGCATTGGACAAT 3893
AAV-2 .....G..TC.C..C.....G..GC.AG..T.A.AGAAAA....TGTGAACA.T..A..G 3870
AAV-6 .......................G.................................... 3878

AAV-1 GTCATGATTACAGACGAAGAGGAAATTAAAGCCACTAACCCTGTGGCCACCGAAAGATTT 3953
AAV-2 ..........................CGG.A.A..C..T..C.....T..G..GCAG.A 3930
AAV-6 ........C............C............C........................ 3938

AAV-1 GGGACCGTGGCAGTCAATTTCCAGAGCAGCAGCACAGACCCTGCGACCGGAGATGTGCAT 4013
AAV-2 ..TT.T..AT.TAC...CC.......AG...A..G.C.AG.A..T....C......CA.C 3990
AAV-6 .....T............C.......................................... 3998

AAV-1 GCTATGGGAGCATTACCTGGCATGGTGTGGCAAGATAGAGACGTGTACCTGCAGGGTCCC 4073
AAV-2 A.ACAA..C.TTC.T..A.........C.....G..C.....T........T.....G... 4050
AAV-6 T..........C.........A..............C........A............T 4058
```

FIG. 1F

```
AAV-1  ATTTGGGCCAAAATTCCTCACACAGATGGACACTTTCACCCGTCTCCTCTTATGGGCGGC  4133
AAV-2  ..C.....A..G.....A.....G..C.....T........C.....C..C.....T..A  4110
AAV-6  ................G............................C..........    4118

AAV-1  TTTGGACTCAAGAACCCGCCTCCTCAGATCCTCATCAAAAACACGCCTGTTCCTGCGAAT  4193
AAV-2  ..C.....T..AC....T.....A.....T........G.....C..G...A........  4170
AAV-6  ........T...C................................................  4178

AAV-1  CCTCCGGCGGAGTTTTCAGCTACAAAGTTTGCTTCATTCATCACCCAATACTCCACAGGA  4253
AAV-2  ...T..A.CACC..CAGT..GG.............C.........A..G........G...  4230
AAV-6  ........A........G...........................G..T..........  4238

AAV-1  CA-AGTGAGTGTGGAAATTGAATGGGAGCTGCAGAAAGAAAACAGCAAGCGCTGGAATCC  4312
AAV-2  ..CG..C..C.....G..C..G............G...........A...........  4290
AAV-6  ..-.....C.....G.............................A...........  4297

AAV-1  CGAAGTGCAGTACACATCCAATTATGCAAAATCTGCCAA-CGTTGATTTTACTGTGGACA  4371
AAV-2  ....A.T........T.....C..CAAC..G....TT..T...G..C.....C.....T.  4350
AAV-6  ..............T.....T..C..............-..........C..........  4356

AAV-1  ACAATGGACTTTATACTGAGCCTCGCCCCATTGGCACCCGTTACCTTACCCGTCCCCTGT  4431
AAV-2  CT.....CG.G...T.A..................A.A.....G..T...AAT....  4410
AAV-6  ................................................C............  4416

VP1-3 stop   PolyA signal
AAV-1  AATTACGTGTTAATCAATAAACCGGTTGATTCGTTTCAGTTGAACTTTGGTCTCCTGTCC  4491
AAV-2  ....G.T................T..A........................TGCGTA  4470
AAV-6  ....GT................A.....G......................A....G  4476

AAV-1  TTCTTATCTTATC-GGTTACCATGGTTAT-AGCTTACACATTA--ACTGCTTGGTTGCGC  4547
AAV-2  ..TC.T.......TA...T.......C..CGTAGA..AGT.GC.TGG.G.G..AA.CATTA  4530
AAV-6  ..A..........T...C.....A.CA.C-C.G..........--.......A.......  4533

AAV-1  TTCGCGATAAAAGACTTACGTCATCGGGttaccoctagtgatggagttgcccactccctc  4607
AAV-2  ACTA.A.gg.a---------------------............g..........  4570
AAV-6  .......at.--------------------..................  4572

AAV-1  tctgcgcgctcgctcgctcggtgggccggcagagcagagctctgccgtctgcggaccct  4667
AAV-2  .c..............ac..a......gc..c..a...g..gc...a.gc.c.gg...  4630
AAV-6  .a..................g....................................  4632

AAV-1  tggtccgcaggccccaccgagcgagcgagcgcgcagagagggagtgggcaa           4718
AAV-2  ..cc.g.gc....t..gt............................c...            4681
AAV-6  ................................t...............             4683
```

FIG. 2

```
AAV-1 TR
            A   A
         A
         G   C
         G   C
         T   A
         C   G
        gC   Gc
        cG   Cg
         C   G
        aA Tg   a   ca                                              ---aav-1 itr
         G  CCGGGGTGGCTCGCTCGGCGTCTCTCCCTCACCCGTT                   ---aav-2 itr
      A                                g                           ---AAV-1 ITR
         C  GGCCCCACCGAGCGAGCGCGAGAGAGGGAGTGGGCAACTCCATCACTAGGGGTAA
         G   C       t   gt                    c                          tcct
        cG  Cg
         C   G
        cA  Tg
         G   C
        gA  Tc
         G   C
         C   G
         T   T
           C
           t
```

FIG. 4A

| Group | 1 | 2 | 3 | 4 | 5 | 6 |
|---|---|---|---|---|---|---|
| Vector1-α1AT | AAV2 | AAV1 | PBS | PBS | AAV2 | AAV1 |
| Vector2-EPO | AAV2 | AAV1 | AAV2 | AAV1 | AAV1 | AAV2 |

| Group | 1 | 2 | 3 | 4 | 5 | 6 |
|---|---|---|---|---|---|---|
| Vector1-α1AT | AAV2 | AAV1 | PBS | PBS | AAV2 | AAV1 |
| Vector2-EPO | AAV2 | AAV1 | AAV2 | AAV1 | AAV1 | AAV2 |

SEQUENCE LISTING

<160> NUMBER OF SEQ ID NOS: 20

<210> SEQ ID NO 1
<211> LENGTH: 4718
<212> TYPE: DNA
<213> ORGANISM: AAV-1
<220> FEATURE:
<221> NAME/KEY: CDS
<222> LOCATION: (335)..(2206)
<223> OTHER INFORMATION:
<220> FEATURE:
<221> NAME/KEY: CDS
<222> LOCATION: (2223)..(4430)
<223> OTHER INFORMATION:

<400> SEQUENCE: 1

```
ttgcccactc cctctctgcg cgctcgctcg ctcggtgggg cctgcggacc aaaggtccgc         60
agacggcaga gctctgctct gccggcccca ccgagcgagc gagcgcgcag agagggagtg        120
ggcaactcca tcactagggg taatcgcgaa gcgcctccca cgctgccgcg tcagcgctga        180
cgtaaattac gtcataggag agtggtcctg tattagctgt cacgtgagtg cttttgcgac        240
attttgcgac accacgtggc catttagggt atatatggcc gagtgagcga gcaggatctc        300
cattttgacc gcgaaatttg aacgagcagc agcc atg ccg ggc ttc tac gag atc       355
                                     Met Pro Gly Phe Tyr Glu Ile
                                       1               5 gtg atc aag gtg ccg agc gac ctg gac gag cac ctg ccg ggc att tct         403
Val Ile Lys Val Pro Ser Asp Leu Asp Glu His Leu Pro Gly Ile Ser
         10                  15                  20 gac tcg ttt gtg agc tgg gtg gcc gag aag gaa tgg gag ctg ccc ccg         451
Asp Ser Phe Val Ser Trp Val Ala Glu Lys Glu Trp Glu Leu Pro Pro
     25                  30                  35 gat tct gac atg gat ctg aat ctg att gag cag gca ccc ctg acc gtg         499
Asp Ser Asp Met Asp Leu Asn Leu Ile Glu Gln Ala Pro Leu Thr Val
 40                  45                  50                  55 gcc gag aag ctg cag cgc gac ttc ctg gtc caa tgg cgc cgc gtg agt         547
Ala Glu Lys Leu Gln Arg Asp Phe Leu Val Gln Trp Arg Arg Val Ser
                 60                  65                  70 aag gcc ccg gag gcc ctc ttc ttt gtt cag ttc gag aag ggc gag tcc         595
Lys Ala Pro Glu Ala Leu Phe Phe Val Gln Phe Glu Lys Gly Glu Ser
             75                  80                  85 tac ttc cac ctc cat att ctg gtg gag acc acg ggg gtc aaa tcc atg         643
Tyr Phe His Leu His Ile Leu Val Glu Thr Thr Gly Val Lys Ser Met
         90                  95                 100 gtg ctg ggc cgc ttc ctg agt cag att agg gac aag ctg gtg cag acc         691
Val Leu Gly Arg Phe Leu Ser Gln Ile Arg Asp Lys Leu Val Gln Thr
    105                 110                 115 atc tac cgc ggg atc gag ccg acc ctg ccc aac tgg ttc gcg gtg acc         739
Ile Tyr Arg Gly Ile Glu Pro Thr Leu Pro Asn Trp Phe Ala Val Thr
120                 125                 130                 135 aag acg cgt aat ggc gcc gga ggg ggg aac aag gtg gtg gac gag tgc         787
Lys Thr Arg Asn Gly Ala Gly Gly Gly Asn Lys Val Val Asp Glu Cys
                140                 145                 150 tac atc ccc aac tac ctc ctg ccc aag act cag ccc gag ctg cag tgg         835
Tyr Ile Pro Asn Tyr Leu Leu Pro Lys Thr Gln Pro Glu Leu Gln Trp
            155                 160                 165 gcg tgg act aac atg gag gag tat ata agc gcc tgt ttg aac ctg gcc         883
Ala Trp Thr Asn Met Glu Glu Tyr Ile Ser Ala Cys Leu Asn Leu Ala
        170                 175                 180 gag cgc aaa cgg ctc gtg gcg cag cac ctg acc cac gtc agc cag acc         931
Glu Arg Lys Arg Leu Val Ala Gln His Leu Thr His Val Ser Gln Thr
    185                 190                 195
```

-continued

| | | |
|---|---|---|
| cag gag cag aac aag gag aat ctg aac ccc aat tct gac gcg cct gtc<br>Gln Glu Gln Asn Lys Glu Asn Leu Asn Pro Asn Ser Asp Ala Pro Val<br>200               205               210               215 | 979 |
| atc cgg tca aaa acc tcc gcg cgc tac atg gag ctg gtc ggg tgg ctg<br>Ile Arg Ser Lys Thr Ser Ala Arg Tyr Met Glu Leu Val Gly Trp Leu<br>               220               225               230 | 1027 |
| gtg gac cgg ggc atc acc tcc gag aag cag tgg atc cag gag gac cag<br>Val Asp Arg Gly Ile Thr Ser Glu Lys Gln Trp Ile Gln Glu Asp Gln<br>235               240               245 | 1075 |
| gcc tcg tac atc tcc ttc aac gcc gct tcc aac tcg cgg tcc cag atc<br>Ala Ser Tyr Ile Ser Phe Asn Ala Ala Ser Asn Ser Arg Ser Gln Ile<br>               250               255               260 | 1123 |
| aag gcc gct ctg gac aat gcc ggc aag atc atg gcg ctg acc aaa tcc<br>Lys Ala Ala Leu Asp Asn Ala Gly Lys Ile Met Ala Leu Thr Lys Ser<br>265               270               275 | 1171 |
| gcg ccc gac tac ctg gta ggc ccc gct ccg ccc gcg gac att aaa acc<br>Ala Pro Asp Tyr Leu Val Gly Pro Ala Pro Pro Ala Asp Ile Lys Thr<br>280               285               290               295 | 1219 |
| aac cgc atc tac cgc atc ctg gag ctg aac ggc tac gaa cct gcc tac<br>Asn Arg Ile Tyr Arg Ile Leu Glu Leu Asn Gly Tyr Glu Pro Ala Tyr<br>               300               305               310 | 1267 |
| gcc ggc tcc gtc ttt ctc ggc tgg gcc cag aaa agg ttc ggg aag cgc<br>Ala Gly Ser Val Phe Leu Gly Trp Ala Gln Lys Arg Phe Gly Lys Arg<br>315               320               325 | 1315 |
| aac acc atc tgg ctg ttt ggg ccg gcc acc acg ggc aag acc aac atc<br>Asn Thr Ile Trp Leu Phe Gly Pro Ala Thr Thr Gly Lys Thr Asn Ile<br>               330               335               340 | 1363 |
| gcg gaa gcc atc gcc cac gcc gtg ccc ttc tac ggc tgc gtc aac tgg<br>Ala Glu Ala Ile Ala His Ala Val Pro Phe Tyr Gly Cys Val Asn Trp<br>345               350               355 | 1411 |
| acc aat gag aac ttt ccc ttc aat gat tgc gtc gac aag atg gtg atc<br>Thr Asn Glu Asn Phe Pro Phe Asn Asp Cys Val Asp Lys Met Val Ile<br>360               365               370               375 | 1459 |
| tgg tgg gag gag ggc aag atg acg gcc aag gtc gtg gag tcc gcc aag<br>Trp Trp Glu Glu Gly Lys Met Thr Ala Lys Val Val Glu Ser Ala Lys<br>               380               385               390 | 1507 |
| gcc att ctc ggc ggc agc aag gtc cgc gtg gac caa aag tgc aag tcg<br>Ala Ile Leu Gly Gly Ser Lys Val Arg Val Asp Gln Lys Cys Lys Ser<br>               395               400               405 | 1555 |
| tcc gcc cag atc gac ccc acc ccc gtg atc gtc acc tcc aac acc aac<br>Ser Ala Gln Ile Asp Pro Thr Pro Val Ile Val Thr Ser Asn Thr Asn<br>               410               415               420 | 1603 |
| atg tgc gcc gtg att gac ggg aac agc acc acc ttc gag cac cag cag<br>Met Cys Ala Val Ile Asp Gly Asn Ser Thr Thr Phe Glu His Gln Gln<br>425               430               435 | 1651 |
| ccg ttg cag gac cgg atg ttc aaa ttt gaa ctc acc cgc cgt ctg gag<br>Pro Leu Gln Asp Arg Met Phe Lys Phe Glu Leu Thr Arg Arg Leu Glu<br>440             445               450               455 | 1699 |
| cat gac ttt ggc aag gtg aca aag cag gaa gtc aaa gag ttc ttc cgc<br>His Asp Phe Gly Lys Val Thr Lys Gln Glu Val Lys Glu Phe Phe Arg<br>               460               465               470 | 1747 |
| tgg gcg cag gat cac gtg acc gag gtg gcg cat gag ttc tac gtc aga<br>Trp Ala Gln Asp His Val Thr Glu Val Ala His Glu Phe Tyr Val Arg<br>               475               480               485 | 1795 |
| aag ggt gga gcc aac aaa aga ccc gcc ccc gat gac gcg gat aaa agc<br>Lys Gly Gly Ala Asn Lys Arg Pro Ala Pro Asp Asp Ala Asp Lys Ser<br>               490               495               500 | 1843 |
| gag ccc aag cgg gcc tgc ccc tca gtc gcg gat cca tcg acg tca gac<br>Glu Pro Lys Arg Ala Cys Pro Ser Val Ala Asp Pro Ser Thr Ser Asp | 1891 |

-continued

```
       505                 510                 515
gcg gaa gga gct ccg gtg gac ttt gcc gac agg tac caa aac aaa tgt        1939
Ala Glu Gly Ala Pro Val Asp Phe Ala Asp Arg Tyr Gln Asn Lys Cys
520                 525                 530                 535 tct cgt cac gcg ggc atg ctt cag atg ctg ttt ccc tgc aag aca tgc        1987
Ser Arg His Ala Gly Met Leu Gln Met Leu Phe Pro Cys Lys Thr Cys
                540                 545                 550 gag aga atg aat cag aat ttc aac att tgc ttc acg cac ggg acg aga        2035
Glu Arg Met Asn Gln Asn Phe Asn Ile Cys Phe Thr His Gly Thr Arg
            555                 560                 565 gac tgt tca gag tgc ttc ccc ggc gtg tca gaa tct caa ccg gtc gtc        2083
Asp Cys Ser Glu Cys Phe Pro Gly Val Ser Glu Ser Gln Pro Val Val
        570                 575                 580 aga aag agg acg tat cgg aaa ctc tgt gcc att cat cat ctg ctg ggg        2131
Arg Lys Arg Thr Tyr Arg Lys Leu Cys Ala Ile His His Leu Leu Gly
585                 590                 595 cgg gct ccc gag att gct tgc tcg gcc tgc gat ctg gtc aac gtg gac        2179
Arg Ala Pro Glu Ile Ala Cys Ser Ala Cys Asp Leu Val Asn Val Asp
600                 605                 610                 615 ctg gat gac tgt gtt tct gag caa taa atgacttaaa ccaggt atg gct gcc     2231
Leu Asp Asp Cys Val Ser Glu Gln                    Met Ala Ala
                620                                     625 gat ggt tat ctt cca gat tgg ctc gag gac aac ctc tct gag ggc att        2279
Asp Gly Tyr Leu Pro Asp Trp Leu Glu Asp Asn Leu Ser Glu Gly Ile
            630                 635                 640 cgc gag tgg tgg gac ttg aaa cct gga gcc ccg aag ccc aaa gcc aac        2327
Arg Glu Trp Trp Asp Leu Lys Pro Gly Ala Pro Lys Pro Lys Ala Asn
        645                 650                 655 cag caa aag cag gac gac ggc cgg ggt ctg gtg ctt cct ggc tac aag        2375
Gln Gln Lys Gln Asp Asp Gly Arg Gly Leu Val Leu Pro Gly Tyr Lys
660                 665                 670 tac ctc gga ccc ttc aac gga ctc gac aag ggg gag ccc gtc aac gcg        2423
Tyr Leu Gly Pro Phe Asn Gly Leu Asp Lys Gly Glu Pro Val Asn Ala
675                 680                 685                 690 gcg gac gca gcg gcc ctc gag cac gac aag gcc tac gac cag cag ctc        2471
Ala Asp Ala Ala Ala Leu Glu His Asp Lys Ala Tyr Asp Gln Gln Leu
                695                 700                 705 aaa gcg ggt gac aat ccg tac ctg cgg tat aac cac gcc gac gcc gag        2519
Lys Ala Gly Asp Asn Pro Tyr Leu Arg Tyr Asn His Ala Asp Ala Glu
            710                 715                 720 ttt cag gag cgt ctg caa gaa gat acg tct ttt ggg ggc aac ctc ggg        2567
Phe Gln Glu Arg Leu Gln Glu Asp Thr Ser Phe Gly Gly Asn Leu Gly
        725                 730                 735 cga gca gtc ttc cag gcc aag aag cgg gtt ctc gaa cct ctc ggt ctg        2615
Arg Ala Val Phe Gln Ala Lys Lys Arg Val Leu Glu Pro Leu Gly Leu
740                 745                 750 gtt gag gaa ggc gct aag acg gct cct gga aag aaa cgt ccg gta gag        2663
Val Glu Glu Gly Ala Lys Thr Ala Pro Gly Lys Lys Arg Pro Val Glu
755                 760                 765                 770 cag tcg cca caa gag cca gac tcc tcc tcg ggc atc ggc aag aca ggc        2711
Gln Ser Pro Gln Glu Pro Asp Ser Ser Ser Gly Ile Gly Lys Thr Gly
                775                 780                 785 cag cag ccc gct aaa aag aga ctc aat ttt ggt cag act ggc gac tca        2759
Gln Gln Pro Ala Lys Lys Arg Leu Asn Phe Gly Gln Thr Gly Asp Ser
            790                 795                 800 gag tca gtc ccc gat cca caa cct ctc gga gaa cct cca gca acc ccc        2807
Glu Ser Val Pro Asp Pro Gln Pro Leu Gly Glu Pro Pro Ala Thr Pro
        805                 810                 815 gct gct gtg gga cct act aca atg gct tca ggc ggt ggc gca cca atg        2855
```

```
                Ala Ala Val Gly Pro Thr Thr Met Ala Ser Gly Gly Ala Pro Met
                        820             825             830 gca aat aac gaa ggc gcc gac gga gtg ggt aat gcc tca gga aat            2903
Ala Asp Asn Asn Glu Gly Ala Asp Gly Val Gly Asn Ala Ser Gly Asn
835                 840                 845                 850 tgg cat tgc gat tcc aca tgg ctg ggc gac aga gtc atc acc acc agc        2951
Trp His Cys Asp Ser Thr Trp Leu Gly Asp Arg Val Ile Thr Thr Ser
                855                 860                 865 acc cgc acc tgg gcc ttg ccc acc tac aat aac cac ctc tac aag caa        2999
Thr Arg Thr Trp Ala Leu Pro Thr Tyr Asn Asn His Leu Tyr Lys Gln
        870                 875                 880 atc tcc agt gct tca acg ggg gcc agc aac gac aac cac tac ttc ggc        3047
Ile Ser Ser Ala Ser Thr Gly Ala Ser Asn Asp Asn His Tyr Phe Gly
            885                 890                 895 tac agc acc ccc tgg ggg tat ttt gat ttc aac aga ttc cac tgc cac        3095
Tyr Ser Thr Pro Trp Gly Tyr Phe Asp Phe Asn Arg Phe His Cys His
        900                 905                 910 ttt tca cca cgt gac tgg cag cga ctc atc aac aac aat tgg gga ttc        3143
Phe Ser Pro Arg Asp Trp Gln Arg Leu Ile Asn Asn Asn Trp Gly Phe
915                 920                 925                 930 cgg ccc aag aga ctc aac ttc aaa ctc ttc aac atc caa gtc aag gag        3191
Arg Pro Lys Arg Leu Asn Phe Lys Leu Phe Asn Ile Gln Val Lys Glu
                935                 940                 945 gtc acg acg aat gat ggc gtc aca acc atc gct aat aac ctt acc agc        3239
Val Thr Thr Asn Asp Gly Val Thr Thr Ile Ala Asn Asn Leu Thr Ser
        950                 955                 960 acg gtt caa gtc ttc tcg gac tcg gag tac cag ctt ccg tac gtc ctc        3287
Thr Val Gln Val Phe Ser Asp Ser Glu Tyr Gln Leu Pro Tyr Val Leu
            965                 970                 975 ggc tct gcg cac cag ggc tgc ctc cct ccg ttc ccg gcg gac gtg ttc        3335
Gly Ser Ala His Gln Gly Cys Leu Pro Pro Phe Pro Ala Asp Val Phe
        980                 985                 990 atg att ccg caa tac ggc tac ctg acg ctc aac aat ggc agc caa            3380
Met Ile Pro Gln Tyr Gly Tyr Leu Thr Leu Asn Asn Gly Ser Gln
995                 1000                1005 gcc gtg gga cgt tca tcc ttt tac tgc ctg gaa tat ttc cct tct            3425
Ala Val Gly Arg Ser Ser Phe Tyr Cys Leu Glu Tyr Phe Pro Ser
1010                1015                1020 cag atg ctg aga acg ggc aac aac ttt acc ttc agc tac acc ttt            3470
Gln Met Leu Arg Thr Gly Asn Asn Phe Thr Phe Ser Tyr Thr Phe
1025                1030                1035 gag gaa gtg cct ttc cac agc agc tac gcg cac agc cag agc ctg            3515
Glu Glu Val Pro Phe His Ser Ser Tyr Ala His Ser Gln Ser Leu
1040                1045                1050 gac cgg ctg atg aat cct ctc atc gac caa tac ctg tat tac ctg            3560
Asp Arg Leu Met Asn Pro Leu Ile Asp Gln Tyr Leu Tyr Tyr Leu
1055                1060                1065 aac aga act caa aat cag tcc gga agt gcc caa aac aag gac ttg            3605
Asn Arg Thr Gln Asn Gln Ser Gly Ser Ala Gln Asn Lys Asp Leu
1070                1075                1080 ctg ttt agc cgt ggg tct cca gct ggc atg tct gtt cag ccc aaa            3650
Leu Phe Ser Arg Gly Ser Pro Ala Gly Met Ser Val Gln Pro Lys
1085                1090                1095 aac tgg cta cct gga ccc tgt tat cgg cag cag cgc gtt tct aaa            3695
Asn Trp Leu Pro Gly Pro Cys Tyr Arg Gln Gln Arg Val Ser Lys
1100                1105                1110 aca aaa aca gac aac aac aac agc aat ttt acc tgg act ggt gct            3740
Thr Lys Thr Asp Asn Asn Asn Ser Asn Phe Thr Trp Thr Gly Ala
1115                1120                1125
```

| | | | | | | | | | | | | | | | |
|---|---|---|---|---|---|---|---|---|---|---|---|---|---|---|---|
| tca | aaa | tat | aac | ctc | aat | ggg | cgt | gaa | tcc | atc | atc | aac | cct | ggc | 3785 |
| Ser | Lys | Tyr | Asn | Leu | Asn | Gly | Arg | Glu | Ser | Ile | Ile | Asn | Pro | Gly | |
| 1130 | | | | 1135 | | | | | 1140 | | | | | | |
| act | gct | atg | gcc | tca | cac | aaa | gac | gac | gaa | gac | aag | ttc | ttt | ccc | 3830 |
| Thr | Ala | Met | Ala | Ser | His | Lys | Asp | Asp | Glu | Asp | Lys | Phe | Phe | Pro | |
| 1145 | | | | 1150 | | | | | 1155 | | | | | | |
| atg | agc | ggt | gtc | atg | att | ttt | gga | aaa | gag | agc | gcc | gga | gct | tca | 3875 |
| Met | Ser | Gly | Val | Met | Ile | Phe | Gly | Lys | Glu | Ser | Ala | Gly | Ala | Ser | |
| 1160 | | | | 1165 | | | | | 1170 | | | | | | |
| aac | act | gca | ttg | gac | aat | gtc | atg | att | aca | gac | gaa | gag | gaa | att | 3920 |
| Asn | Thr | Ala | Leu | Asp | Asn | Val | Met | Ile | Thr | Asp | Glu | Glu | Glu | Ile | |
| 1175 | | | | 1180 | | | | | 1185 | | | | | | |
| aaa | gcc | act | aac | cct | gtg | gcc | acc | gaa | aga | ttt | ggg | acc | gtg | gca | 3965 |
| Lys | Ala | Thr | Asn | Pro | Val | Ala | Thr | Glu | Arg | Phe | Gly | Thr | Val | Ala | |
| 1190 | | | | 1195 | | | | | 1200 | | | | | | |
| gtc | aat | ttc | cag | agc | agc | agc | aca | gac | cct | gcg | acc | gga | gat | gtg | 4010 |
| Val | Asn | Phe | Gln | Ser | Ser | Ser | Thr | Asp | Pro | Ala | Thr | Gly | Asp | Val | |
| 1205 | | | | 1210 | | | | | 1215 | | | | | | |
| cat | gct | atg | gga | gca | tta | cct | ggc | atg | gtg | tgg | caa | gat | aga | gac | 4055 |
| His | Ala | Met | Gly | Ala | Leu | Pro | Gly | Met | Val | Trp | Gln | Asp | Arg | Asp | |
| 1220 | | | | 1225 | | | | | 1230 | | | | | | |
| gtg | tac | ctg | cag | ggt | ccc | att | tgg | gcc | aaa | att | cct | cac | aca | gat | 4100 |
| Val | Tyr | Leu | Gln | Gly | Pro | Ile | Trp | Ala | Lys | Ile | Pro | His | Thr | Asp | |
| 1235 | | | | 1240 | | | | | 1245 | | | | | | |
| gga | cac | ttt | cac | ccg | tct | cct | ctt | atg | ggc | ggc | ttt | gga | ctc | aag | 4145 |
| Gly | His | Phe | His | Pro | Ser | Pro | Leu | Met | Gly | Gly | Phe | Gly | Leu | Lys | |
| 1250 | | | | 1255 | | | | | 1260 | | | | | | |
| aac | ccg | cct | cct | cag | atc | ctc | atc | aaa | aac | acg | cct | gtt | cct | gcg | 4190 |
| Asn | Pro | Pro | Pro | Gln | Ile | Leu | Ile | Lys | Asn | Thr | Pro | Val | Pro | Ala | |
| 1265 | | | | 1270 | | | | | 1275 | | | | | | |
| aat | cct | ccg | gcg | gag | ttt | tca | gct | aca | aag | ttt | gct | tca | ttc | atc | 4235 |
| Asn | Pro | Pro | Ala | Glu | Phe | Ser | Ala | Thr | Lys | Phe | Ala | Ser | Phe | Ile | |
| 1280 | | | | 1285 | | | | | 1290 | | | | | | |
| acc | caa | tac | tcc | aca | gga | caa | gtg | agt | gtg | gaa | att | gaa | tgg | gag | 4280 |
| Thr | Gln | Tyr | Ser | Thr | Gly | Gln | Val | Ser | Val | Glu | Ile | Glu | Trp | Glu | |
| 1295 | | | | 1300 | | | | | 1305 | | | | | | |
| ctg | cag | aaa | gaa | aac | agc | aag | cgc | tgg | aat | ccc | gaa | gtg | cag | tac | 4325 |
| Leu | Gln | Lys | Glu | Asn | Ser | Lys | Arg | Trp | Asn | Pro | Glu | Val | Gln | Tyr | |
| 1310 | | | | 1315 | | | | | 1320 | | | | | | |
| aca | tcc | aat | tat | gca | aaa | tct | gcc | aac | gtt | gat | ttt | act | gtg | gac | 4370 |
| Thr | Ser | Asn | Tyr | Ala | Lys | Ser | Ala | Asn | Val | Asp | Phe | Thr | Val | Asp | |
| 1325 | | | | 1330 | | | | | 1335 | | | | | | |
| aac | aat | gga | ctt | tat | act | gag | cct | cgc | ccc | att | ggc | acc | cgt | tac | 4415 |
| Asn | Asn | Gly | Leu | Tyr | Thr | Glu | Pro | Arg | Pro | Ile | Gly | Thr | Arg | Tyr | |
| 1340 | | | | 1345 | | | | | 1350 | | | | | | |
| ctt | acc | cgt | ccc | ctg | taattacgtg | ttaatcaata | aaccggttga | ttcgtttcag | | | | | | | 4470 |
| Leu | Thr | Arg | Pro | Leu | | | | | | | | | | | |
| 1355 | | | | | | | | | | | | | | | | ttgaactttg gtctcctgtc cttcttatct tatcggttac catggttata gcttacacat 4530 taactgcttg gttgcgcttc gcgataaaag acttacgtca tcgggttacc cctagtgatg 4590 gagttgccca ctccctctct gcgcgctcgc tcgctcggtg gggcctgcgg accaaaggtc 4650 cgcagacggc agagctctgc tctgccggcc ccaccgagcg agcgagcgcg cagagaggga 4710 gtgggcaa 4718

<210> SEQ ID NO 2
<211> LENGTH: 623
<212> TYPE: PRT
<213> ORGANISM: AAV-1

```
<400> SEQUENCE: 2

Met Pro Gly Phe Tyr Glu Ile Val Ile Lys Val Pro Ser Asp Leu Asp
 1               5                  10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Asp Phe Leu
            50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
                100                 105                 110

Arg Asp Lys Leu Val Gln Thr Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
            275                 280                 285

Pro Pro Ala Asp Ile Lys Thr Asn Arg Ile Tyr Arg Ile Leu Glu Leu
290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
```

```
            405                 410                 415
Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
        450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Leu Gln Met
    530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620

<210> SEQ ID NO 3
<211> LENGTH: 736
<212> TYPE: PRT
<213> ORGANISM: AAV-1

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160
```

```
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
    210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
    290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
    370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
    450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
        515                 520                 525
Asp Asp Glu Asp Lys Phe Phe Pro Met Ser Gly Val Met Ile Phe Gly
    530                 535                 540
Lys Glu Ser Ala Gly Ala Ser Asn Thr Ala Leu Asp Asn Val Met Ile
545                 550                 555                 560
Thr Asp Glu Glu Glu Ile Lys Ala Thr Asn Pro Val Ala Thr Glu Arg
                565                 570                 575
Phe Gly Thr Val Ala Val Asn Phe Gln Ser Ser Ser Thr Asp Pro Ala
```

-continued

```
                580                 585                 590
Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
        610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 4
<211> LENGTH: 1872
<212> TYPE: DNA
<213> ORGANISM: AAV-1
<220> FEATURE:
<221> NAME/KEY: CDS
<222> LOCATION: (1)..(1869)
<223> OTHER INFORMATION:

<400> SEQUENCE: 4 atg ccg ggc ttc tac gag atc gtg atc aag gtg ccg agc gac ctg gac        48
Met Pro Gly Phe Tyr Glu Ile Val Ile Lys Val Pro Ser Asp Leu Asp
1               5                   10                  15 gag cac ctg ccg ggc att tct gac tcg ttt gtg agc tgg gtg gcc gag        96
Glu His Leu Pro Gly Ile Ser Asp Ser Phe Val Ser Trp Val Ala Glu
            20                  25                  30 aag gaa tgg gag ctg ccc ccg gat tct gac atg gat ctg aat ctg att       144
Lys Glu Trp Glu Leu Pro Pro Asp Ser Asp Met Asp Leu Asn Leu Ile
        35                  40                  45 gag cag gca ccc ctg acc gtg gcc gag aag ctg cag cgc gac ttc ctg       192
Glu Gln Ala Pro Leu Thr Val Ala Glu Lys Leu Gln Arg Asp Phe Leu
    50                  55                  60 gtc caa tgg cgc cgc gtg agt aag gcc ccg gag gcc ctc ttc ttt gtt       240
Val Gln Trp Arg Arg Val Ser Lys Ala Pro Glu Ala Leu Phe Phe Val
65                  70                  75                  80 cag ttc gag aag ggc gag tcc tac ttc cac ctc cat att ctg gtg gag       288
Gln Phe Glu Lys Gly Glu Ser Tyr Phe His Leu His Ile Leu Val Glu
                85                  90                  95 acc acg ggg gtc aaa tcc atg gtg ctg ggc cgc ttc ctg agt cag att       336
Thr Thr Gly Val Lys Ser Met Val Leu Gly Arg Phe Leu Ser Gln Ile
            100                 105                 110 agg gac aag ctg gtg cag acc atc tac cgc ggg atc gag ccg acc ctg       384
Arg Asp Lys Leu Val Gln Thr Ile Tyr Arg Gly Ile Glu Pro Thr Leu
        115                 120                 125 ccc aac tgg ttc gcg gtg acc aag acg cgt aat ggc gcc gga ggg ggg       432
Pro Asn Trp Phe Ala Val Thr Lys Thr Arg Asn Gly Ala Gly Gly Gly
    130                 135                 140 aac aag gtg gtg gac gag tgc tac atc ccc aac tac ctc ctg ccc aag       480
Asn Lys Val Val Asp Glu Cys Tyr Ile Pro Asn Tyr Leu Leu Pro Lys
```

|  |  |
|---|---|
| act cag ccc gag ctg cag tgg gcg tgg act aac atg gag gag tat ata<br>Thr Gln Pro Glu Leu Gln Trp Ala Trp Thr Asn Met Glu Glu Tyr Ile<br>                      165                      170                        175 | 528 |
| agc gcc tgt ttg aac ctg gcc gag cgc aaa cgg ctc gtg gcg cag cac<br>Ser Ala Cys Leu Asn Leu Ala Glu Arg Lys Arg Leu Val Ala Gln His<br>                      180                      185                      190 | 576 |
| ctg acc cac gtc agc cag acc cag gag cag aac aag gag aat ctg aac<br>Leu Thr His Val Ser Gln Thr Gln Glu Gln Asn Lys Glu Asn Leu Asn<br>           195                      200                      205 | 624 |
| ccc aat tct gac gcg cct gtc atc cgg tca aaa acc tcc gcg cgc tac<br>Pro Asn Ser Asp Ala Pro Val Ile Arg Ser Lys Thr Ser Ala Arg Tyr<br>210                      215                      220 | 672 |
| atg gag ctg gtc ggg tgg ctg gtg gac cgg ggc atc acc tcc gag aag<br>Met Glu Leu Val Gly Trp Leu Val Asp Arg Gly Ile Thr Ser Glu Lys<br>225                      230                      235                      240 | 720 |
| cag tgg atc cag gag gac cag gcc tcg tac atc tcc ttc aac gcc gct<br>Gln Trp Ile Gln Glu Asp Gln Ala Ser Tyr Ile Ser Phe Asn Ala Ala<br>                      245                      250                      255 | 768 |
| tcc aac tcg cgg tcc cag atc aag gcc gct ctg gac aat gcc ggc aag<br>Ser Asn Ser Arg Ser Gln Ile Lys Ala Ala Leu Asp Asn Ala Gly Lys<br>           260                      265                      270 | 816 |
| atc atg gcg ctg acc aaa tcc gcg ccc gac tac ctg gta ggc ccc gct<br>Ile Met Ala Leu Thr Lys Ser Ala Pro Asp Tyr Leu Val Gly Pro Ala<br>               275                      280                      285 | 864 |
| ccg ccc gcg gac att aaa acc aac cgc atc tac cgc atc ctg gag ctg<br>Pro Pro Ala Asp Ile Lys Thr Asn Arg Ile Tyr Arg Ile Leu Glu Leu<br>290                      295                      300 | 912 |
| aac ggc tac gaa cct gcc tac gcc ggc tcc gtc ttt ctc ggc tgg gcc<br>Asn Gly Tyr Glu Pro Ala Tyr Ala Gly Ser Val Phe Leu Gly Trp Ala<br>305                      310                      315                      320 | 960 |
| cag aaa agg ttc ggg aag cgc aac acc atc tgg ctg ttt ggg ccg gcc<br>Gln Lys Arg Phe Gly Lys Arg Asn Thr Ile Trp Leu Phe Gly Pro Ala<br>                      325                      330                      335 | 1008 |
| acc acg ggc aag acc aac atc gcg gaa gcc atc gcc cac gcc gtg ccc<br>Thr Thr Gly Lys Thr Asn Ile Ala Glu Ala Ile Ala His Ala Val Pro<br>                      340                      345                      350 | 1056 |
| ttc tac ggc tgc gtc aac tgg acc aat gag aac ttt ccc ttc aat gat<br>Phe Tyr Gly Cys Val Asn Trp Thr Asn Glu Asn Phe Pro Phe Asn Asp<br>           355                      360                      365 | 1104 |
| tgc gtc gac aag atg gtg atc tgg tgg gag gag ggc aag atg acg gcc<br>Cys Val Asp Lys Met Val Ile Trp Trp Glu Glu Gly Lys Met Thr Ala<br>370                      375                      380 | 1152 |
| aag gtc gtg gag tcc gcc aag gcc att ctc ggc ggc agc aag gtg cgc<br>Lys Val Val Glu Ser Ala Lys Ala Ile Leu Gly Gly Ser Lys Val Arg<br>385                      390                      395                      400 | 1200 |
| gtg gac caa aag tgc aag tcg tcc gcc cag atc gac ccc acc ccc gtg<br>Val Asp Gln Lys Cys Lys Ser Ser Ala Gln Ile Asp Pro Thr Pro Val<br>                      405                      410                      415 | 1248 |
| atc gtc acc tcc aac acc aac atg tgc gcc gtg att gac ggg aac agc<br>Ile Val Thr Ser Asn Thr Asn Met Cys Ala Val Ile Asp Gly Asn Ser<br>                      420                      425                      430 | 1296 |
| acc acc ttc gag cac cag cag ccg ttg cag gac cgg atg ttc aaa ttt<br>Thr Thr Phe Glu His Gln Gln Pro Leu Gln Asp Arg Met Phe Lys Phe<br>           435                      440                      445 | 1344 |
| gaa ctc acc cgc cgt ctg gag cat gac ttt ggc aag gtg aca aag cag<br>Glu Leu Thr Arg Arg Leu Glu His Asp Phe Gly Lys Val Thr Lys Gln<br>450                      455                      460 | 1392 |
| gaa gtc aaa gag ttc ttc cgc tgg gcg cag gat cac gtg acc gag gtg |  1440 |

```
Glu Val Lys Glu Phe Phe Arg Trp Ala Gln Asp His Val Thr Glu Val
465                 470                 475                 480 gcg cat gag ttc tac gtc aga aag ggt gga gcc aac aaa aga ccc gcc      1488
Ala His Glu Phe Tyr Val Arg Lys Gly Gly Ala Asn Lys Arg Pro Ala
                    485                 490                 495 ccc gat gac gcg gat aaa agc gag ccc aag cgg gcc tgc ccc tca gtc      1536
Pro Asp Asp Ala Asp Lys Ser Glu Pro Lys Arg Ala Cys Pro Ser Val
                500                 505                 510 gcg gat cca tcg acg tca gac gcg gaa gga gct ccg gtg gac ttt gcc      1584
Ala Asp Pro Ser Thr Ser Asp Ala Glu Gly Ala Pro Val Asp Phe Ala
            515                 520                 525 gac agg tac caa aac aaa tgt tct cgt cac gcg ggc atg ctt cag atg      1632
Asp Arg Tyr Gln Asn Lys Cys Ser Arg His Ala Gly Met Leu Gln Met
        530                 535                 540 ctg ttt ccc tgc aag aca tgc gag aga atg aat cag aat ttc aac att      1680
Leu Phe Pro Cys Lys Thr Cys Glu Arg Met Asn Gln Asn Phe Asn Ile
545                 550                 555                 560 tgc ttc acg cac ggg acg aga gac tgt tca gag tgc ttc ccc ggc gtg      1728
Cys Phe Thr His Gly Thr Arg Asp Cys Ser Glu Cys Phe Pro Gly Val
                    565                 570                 575 tca gaa tct caa ccg gtc gtc aga aag agg acg tat cgg aaa ctc tgt      1776
Ser Glu Ser Gln Pro Val Val Arg Lys Arg Thr Tyr Arg Lys Leu Cys
                580                 585                 590 gcc att cat cat ctg ctg ggg cgg gct ccc gag att gct tgc tcg gcc      1824
Ala Ile His His Leu Leu Gly Arg Ala Pro Glu Ile Ala Cys Ser Ala
            595                 600                 605 tgc gat ctg gtc aac gtg gac ctg gat gac tgt gtt tct gag caa taa      1872
Cys Asp Leu Val Asn Val Asp Leu Asp Asp Cys Val Ser Glu Gln
        610                 615                 620

<210> SEQ ID NO 5
<211> LENGTH: 623
<212> TYPE: PRT
<213> ORGANISM: AAV-1

<400> SEQUENCE: 5

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
                100                 105                 110

Arg Asp Lys Leu Val Gln Thr Ile Tyr Arg Gly Ile Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175
```

```
Ser Ala Cys Leu Asn Leu Ala Glu Arg Lys Leu Val Ala Gln His
            180                 185                 190
Leu Thr His Val Ser Gln Thr Gln Glu Gln Asn Lys Glu Asn Leu Asn
        195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ala Leu Thr Lys Ser Ala Pro Asp Tyr Leu Val Gly Pro Ala
        275                 280                 285
Pro Pro Ala Asp Ile Lys Thr Asn Arg Ile Tyr Arg Ile Leu Glu Leu
    290                 295                 300
Asn Gly Tyr Glu Pro Ala Tyr Ala Gly Ser Val Phe Leu Gly Trp Ala
305                 310                 315                 320
Gln Lys Arg Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Arg Arg Leu Glu His Asp Phe Gly Lys Val Thr Lys Gln
    450                 455                 460
Glu Val Lys Glu Phe Phe Arg Trp Ala Gln Asp His Val Thr Glu Val
465                 470                 475                 480
Ala His Glu Phe Tyr Val Arg Lys Gly Gly Ala Asn Lys Arg Pro Ala
                485                 490                 495
Pro Asp Asp Ala Asp Lys Ser Glu Pro Lys Arg Ala Cys Pro Ser Val
            500                 505                 510
Ala Asp Pro Ser Thr Ser Asp Ala Glu Gly Ala Pro Val Asp Phe Ala
        515                 520                 525
Asp Arg Tyr Gln Asn Lys Cys Ser Arg His Ala Gly Met Leu Gln Met
    530                 535                 540
Leu Phe Pro Cys Lys Thr Cys Glu Arg Met Asn Gln Asn Phe Asn Ile
545                 550                 555                 560
Cys Phe Thr His Gly Thr Arg Asp Cys Ser Glu Cys Phe Pro Gly Val
                565                 570                 575
Ser Glu Ser Gln Pro Val Val Arg Lys Arg Thr Tyr Arg Lys Leu Cys
            580                 585                 590
```

```
Ala Ile His His Leu Leu Gly Arg Ala Pro Glu Ile Ala Cys Ser Ala
        595                 600                 605
Cys Asp Leu Val Asn Val Asp Leu Asp Asp Cys Val Ser Glu Gln
    610                 615                 620

<210> SEQ ID NO 6
<211> LENGTH: 1641
<212> TYPE: DNA
<213> ORGANISM: AAV-1
<220> FEATURE:
<221> NAME/KEY: CDS
<222> LOCATION: (1)..(1638)
<223> OTHER INFORMATION:

<400> SEQUENCE: 6
```

| | | | | | | | | | | | | | | | | |
|---|---|---|---|---|---|---|---|---|---|---|---|---|---|---|---|---|
| atg | ccg | ggc | ttc | tac | gag | atc | gtg | atc | aag | gtg | ccg | agc | gac | ctg | gac | 48 |
| Met | Pro | Gly | Phe | Tyr | Glu | Ile | Val | Ile | Lys | Val | Pro | Ser | Asp | Leu | Asp | |
| 1 | | | | 5 | | | | | 10 | | | | | 15 | | |
| gag | cac | ctg | ccg | ggc | att | tct | gac | tcg | ttt | gtg | agc | tgg | gtg | gcc | gag | 96 |
| Glu | His | Leu | Pro | Gly | Ile | Ser | Asp | Ser | Phe | Val | Ser | Trp | Val | Ala | Glu | |
| | | | 20 | | | | | 25 | | | | | 30 | | | |
| aag | gaa | tgg | gag | ctg | ccc | ccg | gat | tct | gac | atg | gat | ctg | aat | ctg | att | 144 |
| Lys | Glu | Trp | Glu | Leu | Pro | Pro | Asp | Ser | Asp | Met | Asp | Leu | Asn | Leu | Ile | |
| | | 35 | | | | | 40 | | | | | 45 | | | | |
| gag | cag | gca | ccc | ctg | acc | gtg | gcc | gag | aag | ctg | cag | cgc | gac | ttc | ctg | 192 |
| Glu | Gln | Ala | Pro | Leu | Thr | Val | Ala | Glu | Lys | Leu | Gln | Arg | Asp | Phe | Leu | |
| | 50 | | | | | 55 | | | | | 60 | | | | | |
| gtc | caa | tgg | cgc | cgc | gtg | agt | aag | gcc | ccg | gag | gcc | ctc | ttc | ttt | gtt | 240 |
| Val | Gln | Trp | Arg | Arg | Val | Ser | Lys | Ala | Pro | Glu | Ala | Leu | Phe | Phe | Val | |
| 65 | | | | 70 | | | | | 75 | | | | | 80 | | |
| cag | ttc | gag | aag | ggc | gag | tcc | tac | ttc | cac | ctc | cat | att | ctg | gtg | gag | 288 |
| Gln | Phe | Glu | Lys | Gly | Glu | Ser | Tyr | Phe | His | Leu | His | Ile | Leu | Val | Glu | |
| | | | | 85 | | | | | 90 | | | | | 95 | | |
| acc | acg | ggg | gtc | aaa | tcc | atg | gtg | ctg | ggc | cgc | ttc | ctg | agt | cag | att | 336 |
| Thr | Thr | Gly | Val | Lys | Ser | Met | Val | Leu | Gly | Arg | Phe | Leu | Ser | Gln | Ile | |
| | | | | 100 | | | | | 105 | | | | | 110 | | |
| agg | gac | aag | ctg | gtg | cag | acc | atc | tac | cgc | ggg | atc | gag | ccg | acc | ctg | 384 |
| Arg | Asp | Lys | Leu | Val | Gln | Thr | Ile | Tyr | Arg | Gly | Ile | Glu | Pro | Thr | Leu | |
| | | | 115 | | | | | 120 | | | | | 125 | | | |
| ccc | aac | tgg | ttc | gcg | gtg | acc | aag | acg | cgt | aat | ggc | gcc | gga | ggg | ggg | 432 |
| Pro | Asn | Trp | Phe | Ala | Val | Thr | Lys | Thr | Arg | Asn | Gly | Ala | Gly | Gly | Gly | |
| | | 130 | | | | | 135 | | | | | 140 | | | | |
| aac | aag | gtg | gtg | gac | gag | tgc | tac | atc | ccc | aac | tac | ctc | ctg | ccc | aag | 480 |
| Asn | Lys | Val | Val | Asp | Glu | Cys | Tyr | Ile | Pro | Asn | Tyr | Leu | Leu | Pro | Lys | |
| 145 | | | | 150 | | | | | 155 | | | | | 160 | | |
| act | cag | ccc | gag | ctg | cag | tgg | gcg | tgg | act | aac | atg | gag | gag | tat | ata | 528 |
| Thr | Gln | Pro | Glu | Leu | Gln | Trp | Ala | Trp | Thr | Asn | Met | Glu | Glu | Tyr | Ile | |
| | | | | 165 | | | | | 170 | | | | | 175 | | |
| agc | gcc | tgt | ttg | aac | ctg | gcc | gag | cgc | aaa | cgg | ctc | gtg | gcg | cag | cac | 576 |
| Ser | Ala | Cys | Leu | Asn | Leu | Ala | Glu | Arg | Lys | Arg | Leu | Val | Ala | Gln | His | |
| | | | | 180 | | | | | 185 | | | | | 190 | | |
| ctg | acc | cac | gtc | agc | cag | acc | cag | gag | cag | aac | aag | gag | aat | ctg | aac | 624 |
| Leu | Thr | His | Val | Ser | Gln | Thr | Gln | Glu | Gln | Asn | Lys | Glu | Asn | Leu | Asn | |
| | | | 195 | | | | | 200 | | | | | 205 | | | |
| ccc | aat | tct | gac | gcg | cct | gtc | atc | cgg | tca | aaa | acc | tcc | gcg | cgc | tac | 672 |
| Pro | Asn | Ser | Asp | Ala | Pro | Val | Ile | Arg | Ser | Lys | Thr | Ser | Ala | Arg | Tyr | |
| | | 210 | | | | | 215 | | | | | 220 | | | | |
| atg | gag | ctg | gtc | ggg | tgg | ctg | gtg | gac | cgg | ggc | atc | acc | tcc | gag | aag | 720 |
| Met | Glu | Leu | Val | Gly | Trp | Leu | Val | Asp | Arg | Gly | Ile | Thr | Ser | Glu | Lys | |
| 225 | | | | 230 | | | | | 235 | | | | | 240 | | |
| cag | tgg | atc | cag | gag | gac | cag | gcc | tcg | tac | atc | tcc | ttc | aac | gcc | gct | 768 |
| Gln | Trp | Ile | Gln | Glu | Asp | Gln | Ala | Ser | Tyr | Ile | Ser | Phe | Asn | Ala | Ala | |

-continued

```
                Gln Trp Ile Gln Glu Asp Gln Ala Ser Tyr Ile Ser Phe Asn Ala Ala
                                245                 250                 255 tcc aac tcg cgg tcc cag atc aag gcc gct ctg gac aat gcc ggc aag        816
Ser Asn Ser Arg Ser Gln Ile Lys Ala Ala Leu Asp Asn Ala Gly Lys
            260                 265                 270 atc atg gcg ctg acc aaa tcc gcg ccc gac tac ctg gta ggc ccc gct        864
Ile Met Ala Leu Thr Lys Ser Ala Pro Asp Tyr Leu Val Gly Pro Ala
        275                 280                 285 ccg ccc gcg gac att aaa acc aac cgc atc tac cgc atc ctg gag ctg        912
Pro Pro Ala Asp Ile Lys Thr Asn Arg Ile Tyr Arg Ile Leu Glu Leu
    290                 295                 300 aac ggc tac gaa cct gcc tac gcc ggc tcc gtc ttt ctc ggc tgg gcc        960
Asn Gly Tyr Glu Pro Ala Tyr Ala Gly Ser Val Phe Leu Gly Trp Ala
305                 310                 315                 320 cag aaa agg ttc ggg aag cgc aac acc atc tgg ctg ttt ggg ccg gcc       1008
Gln Lys Arg Phe Gly Lys Arg Asn Thr Ile Trp Leu Phe Gly Pro Ala
                325                 330                 335 acc acg ggc aag acc aac atc gcg gaa gcc atc gcc cac gcc gtg ccc       1056
Thr Thr Gly Lys Thr Asn Ile Ala Glu Ala Ile Ala His Ala Val Pro
            340                 345                 350 ttc tac ggc tgc gtc aac tgg acc aat gag aac ttt ccc ttc aat gat       1104
Phe Tyr Gly Cys Val Asn Trp Thr Asn Glu Asn Phe Pro Phe Asn Asp
        355                 360                 365 tgc gtc gac aag atg gtg atc tgg tgg gag gag ggc aag atg acg gcc       1152
Cys Val Asp Lys Met Val Ile Trp Trp Glu Glu Gly Lys Met Thr Ala
    370                 375                 380 aag gtc gtg gag tcc gcc aag gcc att ctc ggc ggc agc aag gtg cgc       1200
Lys Val Val Glu Ser Ala Lys Ala Ile Leu Gly Gly Ser Lys Val Arg
385                 390                 395                 400 gtg gac caa aag tgc aag tcg tcc gcc cag atc gac ccc acc ccc gtg       1248
Val Asp Gln Lys Cys Lys Ser Ser Ala Gln Ile Asp Pro Thr Pro Val
                405                 410                 415 atc gtc acc tcc aac acc aac atg tgc gcc gtg att gac ggg aac agc       1296
Ile Val Thr Ser Asn Thr Asn Met Cys Ala Val Ile Asp Gly Asn Ser
            420                 425                 430 acc acc ttc gag cac cag cag ccg ttg cag gac cgg atg ttc aaa ttt       1344
Thr Thr Phe Glu His Gln Gln Pro Leu Gln Asp Arg Met Phe Lys Phe
        435                 440                 445 gaa ctc acc cgc cgt ctg gag cat gac ttt ggc aag gtg aca aag cag       1392
Glu Leu Thr Arg Arg Leu Glu His Asp Phe Gly Lys Val Thr Lys Gln
    450                 455                 460 gaa gtc aaa gag ttc ttc cgc tgg gcg cag gat cac gtg acc gag gtg       1440
Glu Val Lys Glu Phe Phe Arg Trp Ala Gln Asp His Val Thr Glu Val
465                 470                 475                 480 gcg cat gag ttc tac gtc aga aag ggt gga gcc aac aaa aga ccc gcc       1488
Ala His Glu Phe Tyr Val Arg Lys Gly Gly Ala Asn Lys Arg Pro Ala
                485                 490                 495 ccc gat gac gcg gat aaa agc gag ccc aag cgg gcc tgc ccc tca gtc       1536
Pro Asp Asp Ala Asp Lys Ser Glu Pro Lys Arg Ala Cys Pro Ser Val
            500                 505                 510 gcg gat cca tcg acg tca gac gcg gaa gga gct ccg gtg gac ttt gcc       1584
Ala Asp Pro Ser Thr Ser Asp Ala Glu Gly Ala Pro Val Asp Phe Ala
        515                 520                 525 gac agg tat ggc tgc cga tgg tta tct tcc aga ttg gct cga gga caa       1632
Asp Arg Tyr Gly Cys Arg Trp Leu Ser Ser Arg Leu Ala Arg Gly Gln
    530                 535                 540 cct ctc tga                                                           1641
Pro Leu
545
```

<210> SEQ ID NO 7
<211> LENGTH: 546
<212> TYPE: PRT
<213> ORGANISM: AAV-1

<400> SEQUENCE: 7

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

-continued

```
Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
        420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gly Cys Arg Trp Leu Ser Ser Arg Leu Ala Arg Gly Gln
    530                 535                 540

Pro Leu
545
```

<210> SEQ ID NO 8
<211> LENGTH: 1200
<212> TYPE: DNA
<213> ORGANISM: AAV-1
<220> FEATURE:
<221> NAME/KEY: CDS
<222> LOCATION: (1)..(1197)
<223> OTHER INFORMATION:

<400> SEQUENCE: 8

```
atg gag ctg gtc ggg tgg ctg gtg gac cgg ggc atc acc tcc gag aag      48
Met Glu Leu Val Gly Trp Leu Val Asp Arg Gly Ile Thr Ser Glu Lys
1               5                   10                  15 cag tgg atc cag gag gac cag gcc tcg tac atc tcc ttc aac gcc gct      96
Gln Trp Ile Gln Glu Asp Gln Ala Ser Tyr Ile Ser Phe Asn Ala Ala
            20                  25                  30 tcc aac tcg cgg tcc cag atc aag gcc gct ctg gac aat gcc ggc aag     144
Ser Asn Ser Arg Ser Gln Ile Lys Ala Ala Leu Asp Asn Ala Gly Lys
        35                  40                  45 atc atg gcg ctg acc aaa tcc gcg ccc gac tac ctg gta ggc ccc gct     192
Ile Met Ala Leu Thr Lys Ser Ala Pro Asp Tyr Leu Val Gly Pro Ala
    50                  55                  60 ccg ccc gcg gac att aaa acc aac cgc atc tac cgc atc ctg gag ctg     240
Pro Pro Ala Asp Ile Lys Thr Asn Arg Ile Tyr Arg Ile Leu Glu Leu
65                  70                  75                  80 aac ggc tac gaa cct gcc tac gcc ggc tcc gtc ttt ctc ggc tgg gcc     288
Asn Gly Tyr Glu Pro Ala Tyr Ala Gly Ser Val Phe Leu Gly Trp Ala
                85                  90                  95 cag aaa agg ttc ggg aag cgc aac acc atc tgg ctg ttt ggg ccg gcc     336
Gln Lys Arg Phe Gly Lys Arg Asn Thr Ile Trp Leu Phe Gly Pro Ala
            100                 105                 110 acc acg ggc aag acc aac atc gcg gaa gcc atc gcc cac gcc gtg ccc     384
Thr Thr Gly Lys Thr Asn Ile Ala Glu Ala Ile Ala His Ala Val Pro
        115                 120                 125 ttc tac ggc tgc gtc aac tgg acc aat gag aac ttt ccc ttc aat gat     432
```

```
                Phe Tyr Gly Cys Val Asn Trp Thr Asn Glu Asn Phe Pro Phe Asn Asp
                    130                 135                 140 tgc gtc gac aag atg gtg atc tgg tgg gag gag ggc aag atg acg gcc       480
Cys Val Asp Lys Met Val Ile Trp Trp Glu Glu Gly Lys Met Thr Ala
145                 150                 155                 160 aag gtc gtg gag tcc gcc aag gcc att ctc ggc ggc agc aag gtg cgc       528
Lys Val Val Glu Ser Ala Lys Ala Ile Leu Gly Gly Ser Lys Val Arg
                165                 170                 175 gtg gac caa aag tgc aag tcg tcc gcc cag atc gac ccc acc ccc gtg       576
Val Asp Gln Lys Cys Lys Ser Ser Ala Gln Ile Asp Pro Thr Pro Val
            180                 185                 190 atc gtc acc tcc aac acc aac atg tgc gcc gtg att gac ggg aac agc       624
Ile Val Thr Ser Asn Thr Asn Met Cys Ala Val Ile Asp Gly Asn Ser
        195                 200                 205 acc acc ttc gag cac cag cag ccg ttg cag gac cgg atg ttc aaa ttt       672
Thr Thr Phe Glu His Gln Gln Pro Leu Gln Asp Arg Met Phe Lys Phe
    210                 215                 220 gaa ctc acc cgc cgt ctg gag cat gac ttt ggc aag gtg aca aag cag       720
Glu Leu Thr Arg Arg Leu Glu His Asp Phe Gly Lys Val Thr Lys Gln
225                 230                 235                 240 gaa gtc aaa gag ttc ttc cgc tgg gcg cag gat cac gtg acc gag gtg       768
Glu Val Lys Glu Phe Phe Arg Trp Ala Gln Asp His Val Thr Glu Val
                245                 250                 255 gcg cat gag ttc tac gtc aga aag ggt gga gcc aac aaa aga ccc gcc       816
Ala His Glu Phe Tyr Val Arg Lys Gly Gly Ala Asn Lys Arg Pro Ala
            260                 265                 270 ccc gat gac gcg gat aaa agc gag ccc aag cgg gcc tgc ccc tca gtc       864
Pro Asp Asp Ala Asp Lys Ser Glu Pro Lys Arg Ala Cys Pro Ser Val
        275                 280                 285 gcg gat cca tcg acg tca gac gcg gaa gga gct ccg gtg gac ttt gcc       912
Ala Asp Pro Ser Thr Ser Asp Ala Glu Gly Ala Pro Val Asp Phe Ala
    290                 295                 300 gac agg tac caa aac aaa tgt tct cgt cac gcg ggc atg ctt cag atg       960
Asp Arg Tyr Gln Asn Lys Cys Ser Arg His Ala Gly Met Leu Gln Met
305                 310                 315                 320 ctg ttt ccc tgc aag aca tgc gag aga atg aat cag aat ttc aac att      1008
Leu Phe Pro Cys Lys Thr Cys Glu Arg Met Asn Gln Asn Phe Asn Ile
                325                 330                 335 tgc ttc acg cac ggg acg aga gac tgt tca gag tgc ttc ccc ggc gtg      1056
Cys Phe Thr His Gly Thr Arg Asp Cys Ser Glu Cys Phe Pro Gly Val
            340                 345                 350 tca gaa tct caa ccg gtc gtc aga aag agg acg tat cgg aaa ctc tgt      1104
Ser Glu Ser Gln Pro Val Val Arg Lys Arg Thr Tyr Arg Lys Leu Cys
        355                 360                 365 gcc att cat cat ctg ctg ggg cgg gct ccc gag att gct tgc tcg gcc      1152
Ala Ile His His Leu Leu Gly Arg Ala Pro Glu Ile Ala Cys Ser Ala
    370                 375                 380 tgc gat ctg gtc aac gtg gac ctg gat gac tgt gtt tct gag caa taa     1200
Cys Asp Leu Val Asn Val Asp Leu Asp Asp Cys Val Ser Glu Gln
385                 390                 395

<210> SEQ ID NO 9
<211> LENGTH: 399
<212> TYPE: PRT
<213> ORGANISM: AAV-1

<400> SEQUENCE: 9

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
```

```
                     20                  25                  30
    Ser Asn Ser Arg Ser Gln Ile Lys Ala Ala Leu Asp Asn Ala Gly Lys
                 35                  40                  45

Ile Met Ala Leu Thr Lys Ser Ala Pro Asp Tyr Leu Val Gly Pro Ala
     50                  55                  60

Pro Pro Ala Asp Ile Lys Thr Asn Arg Ile Tyr Arg Ile Leu Glu Leu
     65                  70                  75                  80

Asn Gly Tyr Glu Pro Ala Tyr Ala Gly Ser Val Phe Leu Gly Trp Ala
                     85                  90                  95

Gln Lys Arg Phe Gly Lys Arg Asn Thr Ile Trp Leu Phe Gly Pro Ala
                100                 105                 110

Thr Thr Gly Lys Thr Asn Ile Ala Glu Ala Ile Ala His Ala Val Pro
                115                 120                 125

Phe Tyr Gly Cys Val Asn Trp Thr Asn Glu Asn Phe Pro Phe Asn Asp
                130                 135                 140

Cys Val Asp Lys Met Val Ile Trp Trp Glu Glu Gly Lys Met Thr Ala
    145                 150                 155                 160

Lys Val Val Glu Ser Ala Lys Ala Ile Leu Gly Gly Ser Lys Val Arg
                    165                 170                 175

Val Asp Gln Lys Cys Lys Ser Ser Ala Gln Ile Asp Pro Thr Pro Val
                180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
                210                 215                 220

Glu Leu Thr Arg Arg Leu Glu His Asp Phe Gly Lys Val Thr Lys Gln
    225                 230                 235                 240

Glu Val Lys Glu Phe Phe Arg Trp Ala Gln Asp His Val Thr Glu Val
                    245                 250                 255

Ala His Glu Phe Tyr Val Arg Lys Gly Gly Ala Asn Lys Arg Pro Ala
                260                 265                 270

Pro Asp Asp Ala Asp Lys Ser Glu Pro Lys Arg Ala Cys Pro Ser Val
                275                 280                 285

Ala Asp Pro Ser Thr Ser Asp Ala Glu Gly Ala Pro Val Asp Phe Ala
                290                 295                 300

Asp Arg Tyr Gln Asn Lys Cys Ser Arg His Ala Gly Met Leu Gln Met
    305                 310                 315                 320

Leu Phe Pro Cys Lys Thr Cys Glu Arg Met Asn Gln Asn Phe Asn Ile
                    325                 330                 335

Cys Phe Thr His Gly Thr Arg Asp Cys Ser Glu Cys Phe Pro Gly Val
                340                 345                 350

Ser Glu Ser Gln Pro Val Val Arg Lys Arg Thr Tyr Arg Lys Leu Cys
                355                 360                 365

Ala Ile His His Leu Leu Gly Arg Ala Pro Glu Ile Ala Cys Ser Ala
                370                 375                 380

Cys Asp Leu Val Asn Val Asp Leu Asp Asp Cys Val Ser Glu Gln
    385                 390                 395

<210> SEQ ID NO 10
<211> LENGTH: 969
<212> TYPE: DNA
<213> ORGANISM: AAV-1
<220> FEATURE:
<221> NAME/KEY: CDS
<222> LOCATION: (1)..(966)
```

```
<223> OTHER INFORMATION:
<220> FEATURE:
<221> NAME/KEY: misc_feature
<222> LOCATION: (943)..(944)
<223> OTHER INFORMATION: minor splice site

<400> SEQUENCE: 10 atg gag ctg gtc ggg tgg ctg gtg gac cgg ggc atc acc tcc gag aag      48
Met Glu Leu Val Gly Trp Leu Val Asp Arg Gly Ile Thr Ser Glu Lys
1               5                   10                  15 cag tgg atc cag gag gac cag gcc tcg tac atc tcc ttc aac gcc gct      96
Gln Trp Ile Gln Glu Asp Gln Ala Ser Tyr Ile Ser Phe Asn Ala Ala
            20                  25                  30 tcc aac tcg cgg tcc cag atc aag gcc gct ctg gac aat gcc ggc aag     144
Ser Asn Ser Arg Ser Gln Ile Lys Ala Ala Leu Asp Asn Ala Gly Lys
        35                  40                  45 atc atg gcg ctg acc aaa tcc gcg ccc gac tac ctg gta ggc ccc gct     192
Ile Met Ala Leu Thr Lys Ser Ala Pro Asp Tyr Leu Val Gly Pro Ala
    50                  55                  60 ccg ccc gcg gac att aaa acc aac cgc atc tac cgc atc ctg gag ctg     240
Pro Pro Ala Asp Ile Lys Thr Asn Arg Ile Tyr Arg Ile Leu Glu Leu
65                  70                  75                  80 aac ggc tac gaa cct gcc tac gcc ggc tcc gtc ttt ctc ggc tgg gcc     288
Asn Gly Tyr Glu Pro Ala Tyr Ala Gly Ser Val Phe Leu Gly Trp Ala
                85                  90                  95 cag aaa agg ttc ggg aag cgc aac acc atc tgg ctg ttt ggg ccg gcc     336
Gln Lys Arg Phe Gly Lys Arg Asn Thr Ile Trp Leu Phe Gly Pro Ala
            100                 105                 110 acc acg ggc aag acc aac atc gcg gaa gcc atc gcc cac gcc gtg ccc     384
Thr Thr Gly Lys Thr Asn Ile Ala Glu Ala Ile Ala His Ala Val Pro
        115                 120                 125 ttc tac ggc tgc gtc aac tgg acc aat gag aac ttt ccc ttc aat gat     432
Phe Tyr Gly Cys Val Asn Trp Thr Asn Glu Asn Phe Pro Phe Asn Asp
    130                 135                 140 tgc gtc gac aag atg gtg atc tgg tgg gag gag ggc aag atg acg gcc     480
Cys Val Asp Lys Met Val Ile Trp Trp Glu Glu Gly Lys Met Thr Ala
145                 150                 155                 160 aag gtc gtg gag tcc gcc aag gcc att ctc ggc ggc agc aag gtg cgc     528
Lys Val Val Glu Ser Ala Lys Ala Ile Leu Gly Gly Ser Lys Val Arg
                165                 170                 175 gtg gac caa aag tgc aag tcg tcc gcc cag atc gac ccc acc ccc gtg     576
Val Asp Gln Lys Cys Lys Ser Ser Ala Gln Ile Asp Pro Thr Pro Val
            180                 185                 190 atc gtc acc tcc aac acc aac atg tgc gcc gtg att gac ggg aac agc     624
Ile Val Thr Ser Asn Thr Asn Met Cys Ala Val Ile Asp Gly Asn Ser
        195                 200                 205 acc acc ttc gag cac cag cag ccg ttg cag gac cgg atg ttc aaa ttt     672
Thr Thr Phe Glu His Gln Gln Pro Leu Gln Asp Arg Met Phe Lys Phe
    210                 215                 220 gaa ctc acc cgc cgt ctg gag cat gac ttt ggc aag gtg aca aag cag     720
Glu Leu Thr Arg Arg Leu Glu His Asp Phe Gly Lys Val Thr Lys Gln
225                 230                 235                 240 gaa gtc aaa gag ttc ttc cgc tgg gcg cag gat cac gtg acc gag gtg     768
Glu Val Lys Glu Phe Phe Arg Trp Ala Gln Asp His Val Thr Glu Val
                245                 250                 255 gcg cat gag ttc tac gtc aga aag ggt gga gcc aac aaa aga ccc gcc     816
Ala His Glu Phe Tyr Val Arg Lys Gly Gly Ala Asn Lys Arg Pro Ala
            260                 265                 270 ccc gat gac gcg gat aaa agc gag ccc aag cgg gcc tgc ccc tca gtc     864
Pro Asp Asp Ala Asp Lys Ser Glu Pro Lys Arg Ala Cys Pro Ser Val
        275                 280                 285
```

| | | | | | | | | | | | | | | | |
|---|---|---|---|---|---|---|---|---|---|---|---|---|---|---|---|
| gcg | gat | cca | tcg | acg | tca | gac | gcg | gaa | gga | gct | ccg | gtg | gac | ttt | gcc | 912
| Ala | Asp | Pro | Ser | Thr | Ser | Asp | Ala | Glu | Gly | Ala | Pro | Val | Asp | Phe | Ala |
| | 290 | | | | 295 | | | | 300 | | | | | | |

| | | | | | | | | | | | | | | | |
|---|---|---|---|---|---|---|---|---|---|---|---|---|---|---|---|
| gac | agg | tat | ggc | tgc | cga | tgg | tta | tct | tcc | aga | ttg | gct | cga | gga | caa | 960
| Asp | Arg | Tyr | Gly | Cys | Arg | Trp | Leu | Ser | Ser | Arg | Leu | Ala | Arg | Gly | Gln |
| 305 | | | | 310 | | | | | 315 | | | | | 320 | | cct ctc tga        969
Pro Leu

```
<210> SEQ ID NO 11
<211> LENGTH: 322
<212> TYPE: PRT
<213> ORGANISM: AAV-1
<220> FEATURE:
<221> NAME/KEY: misc_feature
<222> LOCATION: (943)..(944)
<223> OTHER INFORMATION: minor splice site

<400> SEQUENCE: 11
```

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala

|   |   |   |   |   |   |   |   |   |   |   |   |   |   |   |   |     |
|---|---|---|---|---|---|---|---|---|---|---|---|---|---|---|---|-----|
|   |   |   | 290 |   |   |   | 295 |   |   |   | 300 |   |   |   |   |     |
| Asp | Arg | Tyr | Gly | Cys | Arg | Trp | Leu | Ser | Ser | Arg | Leu | Ala | Arg | Gly | Gln |     |
| 305 |   |   |   | 310 |   |   |   | 315 |   |   |   | 320 |   |   |   |     |
| Pro | Leu |   |   |   |   |   |   |   |   |   |   |   |   |   |   |     |

<210> SEQ ID NO 12
<211> LENGTH: 2211
<212> TYPE: DNA
<213> ORGANISM: AAV-1
<220> FEATURE:
<221> NAME/KEY: CDS
<222> LOCATION: (1)..(2208)
<223> OTHER INFORMATION:

<400> SEQUENCE: 12

| atg | gct | gcc | gat | ggt | tat | ctt | cca | gat | tgg | ctc | gag | gac | aac | ctc | tct | 48 |
|---|---|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |   |
| 1 |   |   |   | 5 |   |   |   |   | 10 |   |   |   |   | 15 |   |   |

| gag | ggc | att | cgc | gag | tgg | tgg | gac | ttg | aaa | cct | gga | gcc | ccg | aag | ccc | 96 |
|---|---|---|---|---|---|---|---|---|---|---|---|---|---|---|---|---|
| Glu | Gly | Ile | Arg | Glu | Trp | Trp | Asp | Leu | Lys | Pro | Gly | Ala | Pro | Lys | Pro |   |
|   |   | 20 |   |   |   |   | 25 |   |   |   |   | 30 |   |   |   |   |

| aaa | gcc | aac | cag | caa | aag | cag | gac | gac | ggc | cgg | ggt | ctg | gtg | ctt | cct | 144 |
|---|---|---|---|---|---|---|---|---|---|---|---|---|---|---|---|---|
| Lys | Ala | Asn | Gln | Gln | Lys | Gln | Asp | Asp | Gly | Arg | Gly | Leu | Val | Leu | Pro |   |
|   | 35 |   |   |   |   | 40 |   |   |   |   | 45 |   |   |   |   |   |

| ggc | tac | aag | tac | ctc | gga | ccc | ttc | aac | gga | ctc | gac | aag | ggg | gag | ccc | 192 |
|---|---|---|---|---|---|---|---|---|---|---|---|---|---|---|---|---|
| Gly | Tyr | Lys | Tyr | Leu | Gly | Pro | Phe | Asn | Gly | Leu | Asp | Lys | Gly | Glu | Pro |   |
| 50 |   |   |   |   | 55 |   |   |   |   | 60 |   |   |   |   |   |   |

| gtc | aac | gcg | gcg | gac | gca | gcg | gcc | ctc | gag | cac | gac | aag | gcc | tac | gac | 240 |
|---|---|---|---|---|---|---|---|---|---|---|---|---|---|---|---|---|
| Val | Asn | Ala | Ala | Asp | Ala | Ala | Ala | Leu | Glu | His | Asp | Lys | Ala | Tyr | Asp |   |
| 65 |   |   |   |   | 70 |   |   |   |   | 75 |   |   |   |   | 80 |   |

| cag | cag | ctc | aaa | gcg | ggt | gac | aat | ccg | tac | ctg | cgg | tat | aac | cac | gcc | 288 |
|---|---|---|---|---|---|---|---|---|---|---|---|---|---|---|---|---|
| Gln | Gln | Leu | Lys | Ala | Gly | Asp | Asn | Pro | Tyr | Leu | Arg | Tyr | Asn | His | Ala |   |
|   |   |   |   | 85 |   |   |   |   | 90 |   |   |   |   | 95 |   |   |

| gac | gcc | gag | ttt | cag | gag | cgt | ctg | caa | gaa | gat | acg | tct | ttt | ggg | ggc | 336 |
|---|---|---|---|---|---|---|---|---|---|---|---|---|---|---|---|---|
| Asp | Ala | Glu | Phe | Gln | Glu | Arg | Leu | Gln | Glu | Asp | Thr | Ser | Phe | Gly | Gly |   |
|   |   |   | 100 |   |   |   |   | 105 |   |   |   |   | 110 |   |   |   |

| aac | ctc | ggg | cga | gca | gtc | ttc | cag | gcc | aag | aag | cgg | gtt | ctc | gaa | cct | 384 |
|---|---|---|---|---|---|---|---|---|---|---|---|---|---|---|---|---|
| Asn | Leu | Gly | Arg | Ala | Val | Phe | Gln | Ala | Lys | Lys | Arg | Val | Leu | Glu | Pro |   |
|   |   | 115 |   |   |   |   | 120 |   |   |   |   | 125 |   |   |   |   |

| ctc | ggt | ctg | gtt | gag | gaa | ggc | gct | aag | acg | gct | cct | gga | aag | aaa | cgt | 432 |
|---|---|---|---|---|---|---|---|---|---|---|---|---|---|---|---|---|
| Leu | Gly | Leu | Val | Glu | Glu | Gly | Ala | Lys | Thr | Ala | Pro | Gly | Lys | Lys | Arg |   |
| 130 |   |   |   |   | 135 |   |   |   |   | 140 |   |   |   |   |   |   |

| ccg | gta | gag | cag | tcg | cca | caa | gag | cca | gac | tcc | tcc | tcg | ggc | atc | ggc | 480 |
|---|---|---|---|---|---|---|---|---|---|---|---|---|---|---|---|---|
| Pro | Val | Glu | Gln | Ser | Pro | Gln | Glu | Pro | Asp | Ser | Ser | Ser | Gly | Ile | Gly |   |
| 145 |   |   |   |   | 150 |   |   |   |   | 155 |   |   |   |   | 160 |   |

| aag | aca | ggc | cag | cag | ccc | gct | aaa | aag | aga | ctc | aat | ttt | ggt | cag | act | 528 |
|---|---|---|---|---|---|---|---|---|---|---|---|---|---|---|---|---|
| Lys | Thr | Gly | Gln | Gln | Pro | Ala | Lys | Lys | Arg | Leu | Asn | Phe | Gly | Gln | Thr |   |
|   |   |   |   | 165 |   |   |   |   | 170 |   |   |   |   | 175 |   |   |

| ggc | gac | tca | gag | tca | gtc | ccc | gat | cca | caa | cct | ctc | gga | gaa | cct | cca | 576 |
|---|---|---|---|---|---|---|---|---|---|---|---|---|---|---|---|---|
| Gly | Asp | Ser | Glu | Ser | Val | Pro | Asp | Pro | Gln | Pro | Leu | Gly | Glu | Pro | Pro |   |
|   |   |   | 180 |   |   |   |   | 185 |   |   |   |   | 190 |   |   |   |

| gca | acc | ccc | gct | gct | gtg | gga | cct | act | aca | atg | gct | tca | ggc | ggt | ggc | 624 |
|---|---|---|---|---|---|---|---|---|---|---|---|---|---|---|---|---|
| Ala | Thr | Pro | Ala | Ala | Val | Gly | Pro | Thr | Thr | Met | Ala | Ser | Gly | Gly | Gly |   |
|   |   | 195 |   |   |   |   | 200 |   |   |   |   | 205 |   |   |   |   |

| gca | cca | atg | gca | gac | aat | aac | gaa | ggc | gcc | gac | gga | gtg | ggt | aat | gcc | 672 |
|---|---|---|---|---|---|---|---|---|---|---|---|---|---|---|---|---|
| Ala | Pro | Met | Ala | Asp | Asn | Asn | Glu | Gly | Ala | Asp | Gly | Val | Gly | Asn | Ala |   |
| 210 |   |   |   |   | 215 |   |   |   |   | 220 |   |   |   |   |   |   |

| tca | gga | aat | tgg | cat | tgc | gat | tcc | aca | tgg | ctg | ggc | gac | aga | gtc | atc | 720 |
|---|---|---|---|---|---|---|---|---|---|---|---|---|---|---|---|---|
| Ser | Gly | Asn | Trp | His | Cys | Asp | Ser | Thr | Trp | Leu | Gly | Asp | Arg | Val | Ile |   |
| 225 |   |   |   |   | 230 |   |   |   |   | 235 |   |   |   |   | 240 |   |

```
acc acc agc acc cgc acc tgg gcc ttg ccc acc tac aat aac cac ctc      768
Thr Thr Ser Thr Arg Thr Trp Ala Leu Pro Thr Tyr Asn Asn His Leu
            245                 250                 255 tac aag caa atc tcc agt gct tca acg ggg gcc agc aac gac aac cac      816
Tyr Lys Gln Ile Ser Ser Ala Ser Thr Gly Ala Ser Asn Asp Asn His
                260                 265                 270 tac ttc ggc tac agc acc ccc tgg ggg tat ttt gat ttc aac aga ttc      864
Tyr Phe Gly Tyr Ser Thr Pro Trp Gly Tyr Phe Asp Phe Asn Arg Phe
                    275                 280                 285 cac tgc cac ttt tca cca cgt gac tgg cag cga ctc atc aac aac aat      912
His Cys His Phe Ser Pro Arg Asp Trp Gln Arg Leu Ile Asn Asn Asn
        290                 295                 300 tgg gga ttc cgg ccc aag aga ctc aac ttc aaa ctc ttc aac atc caa      960
Trp Gly Phe Arg Pro Lys Arg Leu Asn Phe Lys Leu Phe Asn Ile Gln
305                 310                 315                 320 gtc aag gag gtc acg acg aat gat ggc gtc aca acc atc gct aat aac     1008
Val Lys Glu Val Thr Thr Asn Asp Gly Val Thr Thr Ile Ala Asn Asn
                325                 330                 335 ctt acc agc acg gtt caa gtc ttc tcg gac tcg gag tac cag ctt ccg     1056
Leu Thr Ser Thr Val Gln Val Phe Ser Asp Ser Glu Tyr Gln Leu Pro
            340                 345                 350 tac gtc ctc ggc tct gcg cac cag ggc tgc ctc cct ccg ttc ccg gcg     1104
Tyr Val Leu Gly Ser Ala His Gln Gly Cys Leu Pro Pro Phe Pro Ala
                355                 360                 365 gac gtg ttc atg att ccg caa tac ggc tac ctg acg ctc aac aat ggc     1152
Asp Val Phe Met Ile Pro Gln Tyr Gly Tyr Leu Thr Leu Asn Asn Gly
        370                 375                 380 agc caa gcc gtg gga cgt tca tcc ttt tac tgc ctg gaa tat ttc cct     1200
Ser Gln Ala Val Gly Arg Ser Ser Phe Tyr Cys Leu Glu Tyr Phe Pro
385                 390                 395                 400 tct cag atg ctg aga acg ggc aac aac ttt acc ttc agc tac acc ttt     1248
Ser Gln Met Leu Arg Thr Gly Asn Asn Phe Thr Phe Ser Tyr Thr Phe
                405                 410                 415 gag gaa gtg cct ttc cac agc agc tac gcg cac agc cag agc ctg gac     1296
Glu Glu Val Pro Phe His Ser Ser Tyr Ala His Ser Gln Ser Leu Asp
            420                 425                 430 cgg ctg atg aat cct ctc atc gac caa tac ctg tat tac ctg aac aga     1344
Arg Leu Met Asn Pro Leu Ile Asp Gln Tyr Leu Tyr Tyr Leu Asn Arg
                435                 440                 445 act caa aat cag tcc gga agt gcc caa aac aag gac ttg ctg ttt agc     1392
Thr Gln Asn Gln Ser Gly Ser Ala Gln Asn Lys Asp Leu Leu Phe Ser
        450                 455                 460 cgt ggg tct cca gct ggc atg tct gtt cag ccc aaa aac tgg cta cct     1440
Arg Gly Ser Pro Ala Gly Met Ser Val Gln Pro Lys Asn Trp Leu Pro
465                 470                 475                 480 gga ccc tgt tat cgg cag cag cgc gtt tct aaa aca aaa aca gac aac     1488
Gly Pro Cys Tyr Arg Gln Gln Arg Val Ser Lys Thr Lys Thr Asp Asn
                485                 490                 495 aac aac agc aat ttt acc tgg act ggt gct tca aaa tat aac ctc aat     1536
Asn Asn Ser Asn Phe Thr Trp Thr Gly Ala Ser Lys Tyr Asn Leu Asn
            500                 505                 510 ggg cgt gaa tcc atc atc aac cct ggc act gct atg gcc tca cac aaa     1584
Gly Arg Glu Ser Ile Ile Asn Pro Gly Thr Ala Met Ala Ser His Lys
                515                 520                 525 gac gac gaa gac aag ttc ttt ccc atg agc ggt gtc atg att ttt gga     1632
Asp Asp Glu Asp Lys Phe Phe Pro Met Ser Gly Val Met Ile Phe Gly
        530                 535                 540 aaa gag agc gcc gga gct tca aac act gca ttg gac aat gtc atg att     1680
Lys Glu Ser Ala Gly Ala Ser Asn Thr Ala Leu Asp Asn Val Met Ile
545                 550                 555                 560
```

```
aca gac gaa gag gaa att aaa gcc act aac cct gtg gcc acc gaa aga       1728
Thr Asp Glu Glu Glu Ile Lys Ala Thr Asn Pro Val Ala Thr Glu Arg
                565                 570                 575 ttt ggg acc gtg gca gtc aat ttc cag agc agc agc aca gac cct gcg       1776
Phe Gly Thr Val Ala Val Asn Phe Gln Ser Ser Ser Thr Asp Pro Ala
            580                 585                 590 acc gga gat gtg cat gct atg gga gca tta cct ggc atg gtg tgg caa       1824
Thr Gly Asp Val His Ala Met Gly Ala Leu Pro Gly Met Val Trp Gln
        595                 600                 605 gat aga gac gtg tac ctg cag ggt ccc att tgg gcc aaa att cct cac       1872
Asp Arg Asp Val Tyr Leu Gln Gly Pro Ile Trp Ala Lys Ile Pro His
    610                 615                 620 aca gat gga cac ttt cac ccg tct cct ctt atg ggc ggc ttt gga ctc       1920
Thr Asp Gly His Phe His Pro Ser Pro Leu Met Gly Gly Phe Gly Leu
625                 630                 635                 640 aag aac ccg cct cct cag atc ctc atc aaa aac acg cct gtt cct gcg       1968
Lys Asn Pro Pro Pro Gln Ile Leu Ile Lys Asn Thr Pro Val Pro Ala
                645                 650                 655 aat cct ccg gcg gag ttt tca gct aca aag ttt gct tca ttc atc acc       2016
Asn Pro Pro Ala Glu Phe Ser Ala Thr Lys Phe Ala Ser Phe Ile Thr
            660                 665                 670 caa tac tcc aca gga caa gtg agt gtg gaa att gaa tgg gag ctg cag       2064
Gln Tyr Ser Thr Gly Gln Val Ser Val Glu Ile Glu Trp Glu Leu Gln
        675                 680                 685 aaa gaa aac agc aag cgc tgg aat ccc gaa gtg cag tac aca tcc aat       2112
Lys Glu Asn Ser Lys Arg Trp Asn Pro Glu Val Gln Tyr Thr Ser Asn
    690                 695                 700 tat gca aaa tct gcc aac gtt gat ttt act gtg gac aac aat gga ctt       2160
Tyr Ala Lys Ser Ala Asn Val Asp Phe Thr Val Asp Asn Asn Gly Leu
705                 710                 715                 720 tat act gag cct cgc ccc att ggc acc cgt tac ctt acc cgt ccc ctg       2208
Tyr Thr Glu Pro Arg Pro Ile Gly Thr Arg Tyr Leu Thr Arg Pro Leu
                725                 730                 735 taa                                                                    2211

<210> SEQ ID NO 13
<211> LENGTH: 736
<212> TYPE: PRT
<213> ORGANISM: AAV-1

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Met Ala Ser Gly Gly Gly
        195                 200                 205

Ala Pro Met Ala Asp Asn Asn Glu Gly Ala Asp Gly Val Gly Asn Ala
210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
530                 535                 540

Lys Glu Ser Ala Gly Ala Ser Asn Thr Ala Leu Asp Asn Val Met Ile
```

|   |   |   |   |   |   |   |   |   |   |   |   |   |   |   |   |
|---|---|---|---|---|---|---|---|---|---|---|---|---|---|---|---|
| 545 | | | | | 550 | | | | | 555 | | | | | 560 |

Thr Asp Glu Glu Glu Ile Lys Ala Thr Asn Pro Val Ala Thr Glu Arg
                565                570                575

Phe Gly Thr Val Ala Val Asn Phe Gln Ser Ser Thr Asp Pro Ala
            580                585              590

Thr Gly Asp Val His Ala Met Gly Ala Leu Pro Gly Met Val Trp Gln
        595                600              605

Asp Arg Asp Val Tyr Leu Gln Gly Pro Ile Trp Ala Lys Ile Pro His
610                615                620

Thr Asp Gly His Phe His Pro Ser Pro Leu Met Gly Gly Phe Gly Leu
625                630              635              640

Lys Asn Pro Pro Pro Gln Ile Leu Ile Lys Asn Thr Pro Val Pro Ala
                645                650              655

Asn Pro Pro Ala Glu Phe Ser Ala Thr Lys Phe Ala Ser Phe Ile Thr
            660                665              670

Gln Tyr Ser Thr Gly Gln Val Ser Val Glu Ile Glu Trp Glu Leu Gln
        675                680              685

Lys Glu Asn Ser Lys Arg Trp Asn Pro Glu Val Gln Tyr Thr Ser Asn
690                695              700

Tyr Ala Lys Ser Ala Asn Val Asp Phe Thr Val Asp Asn Asn Gly Leu
705                710              715              720

Tyr Thr Glu Pro Arg Pro Ile Gly Thr Arg Tyr Leu Thr Arg Pro Leu
        725                730              735

<210> SEQ ID NO 14
<211> LENGTH: 1800
<212> TYPE: DNA
<213> ORGANISM: AAV-1
<220> FEATURE:
<221> NAME/KEY: CDS
<222> LOCATION: (1)..(1797)
<223> OTHER INFORMATION:

<400> SEQUENCE: 14

```
acg gct cct gga aag aaa cgt ccg gta gag cag tcg cca caa gag cca      48
Thr Ala Pro Gly Lys Lys Arg Pro Val Glu Gln Ser Pro Gln Glu Pro
1               5                   10                  15 gac tcc tcc tcg ggc atc ggc aag aca ggc cag cag ccc gct aaa aag      96
Asp Ser Ser Ser Gly Ile Gly Lys Thr Gly Gln Gln Pro Ala Lys Lys
            20                  25                  30 aga ctc aat ttt ggt cag act ggc gac tca gag tca gtc ccc gat cca    144
Arg Leu Asn Phe Gly Gln Thr Gly Asp Ser Glu Ser Val Pro Asp Pro
        35                  40                  45 caa cct ctc gga gaa cct cca gca acc ccc gct gct gtg gga cct act    192
Gln Pro Leu Gly Glu Pro Pro Ala Thr Pro Ala Ala Val Gly Pro Thr
    50                  55                  60 aca atg gct tca ggc ggt ggc gca cca atg gca gac aat aac gaa ggc    240
Thr Met Ala Ser Gly Gly Gly Ala Pro Met Ala Asp Asn Asn Glu Gly
65                  70                  75                  80 gcc gac gga gtg ggt aat gcc tca gga aat tgg cat tgc gat tcc aca    288
Ala Asp Gly Val Gly Asn Ala Ser Gly Asn Trp His Cys Asp Ser Thr
                85                  90                  95 tgg ctg ggc gac aga gtc atc acc acc agc acc cgc acc tgg gcc ttg    336
Trp Leu Gly Asp Arg Val Ile Thr Thr Ser Thr Arg Thr Trp Ala Leu
            100                 105                 110 ccc acc tac aat aac cac ctc tac aag caa atc tcc agt gct tca acg    384
Pro Thr Tyr Asn Asn His Leu Tyr Lys Gln Ile Ser Ser Ala Ser Thr
        115                 120                 125
```

```
ggg gcc agc aac gac aac cac tac ttc ggc tac agc acc ccc tgg ggg    432
Gly Ala Ser Asn Asp Asn His Tyr Phe Gly Tyr Ser Thr Pro Trp Gly
    130                 135                 140 tat ttt gat ttc aac aga ttc cac tgc cac ttt tca cca cgt gac tgg    480
Tyr Phe Asp Phe Asn Arg Phe His Cys His Phe Ser Pro Arg Asp Trp
145                 150                 155                 160 cag cga ctc atc aac aac aat tgg gga ttc cgg ccc aag aga ctc aac    528
Gln Arg Leu Ile Asn Asn Asn Trp Gly Phe Arg Pro Lys Arg Leu Asn
                165                 170                 175 ttc aaa ctc ttc aac atc caa gtc aag gag gtc acg acg aat gat ggc    576
Phe Lys Leu Phe Asn Ile Gln Val Lys Glu Val Thr Thr Asn Asp Gly
            180                 185                 190 gtc aca acc atc gct aat aac ctt acc agc acg gtt caa gtc ttc tcg    624
Val Thr Thr Ile Ala Asn Asn Leu Thr Ser Thr Val Gln Val Phe Ser
        195                 200                 205 gac tcg gag tac cag ctt ccg tac gtc ctc ggc tct gcg cac cag ggc    672
Asp Ser Glu Tyr Gln Leu Pro Tyr Val Leu Gly Ser Ala His Gln Gly
    210                 215                 220 tgc ctc cct ccg ttc ccg gcg gac gtg ttc atg att ccg caa tac ggc    720
Cys Leu Pro Pro Phe Pro Ala Asp Val Phe Met Ile Pro Gln Tyr Gly
225                 230                 235                 240 tac ctg acg ctc aac aat ggc agc caa gcc gtg gga cgt tca tcc ttt    768
Tyr Leu Thr Leu Asn Asn Gly Ser Gln Ala Val Gly Arg Ser Ser Phe
                245                 250                 255 tac tgc ctg gaa tat ttc cct tct cag atg ctg aga acg ggc aac aac    816
Tyr Cys Leu Glu Tyr Phe Pro Ser Gln Met Leu Arg Thr Gly Asn Asn
            260                 265                 270 ttt acc ttc agc tac acc ttt gag gaa gtg cct ttc cac agc agc tac    864
Phe Thr Phe Ser Tyr Thr Phe Glu Glu Val Pro Phe His Ser Ser Tyr
        275                 280                 285 gcg cac agc cag agc ctg gac cgg ctg atg aat cct ctc atc gac caa    912
Ala His Ser Gln Ser Leu Asp Arg Leu Met Asn Pro Leu Ile Asp Gln
    290                 295                 300 tac ctg tat tac ctg aac aga act caa aat cag tcc gga agt gcc caa    960
Tyr Leu Tyr Tyr Leu Asn Arg Thr Gln Asn Gln Ser Gly Ser Ala Gln
305                 310                 315                 320 aac aag gac ttg ctg ttt agc cgt ggg tct cca gct ggc atg tct gtt   1008
Asn Lys Asp Leu Leu Phe Ser Arg Gly Ser Pro Ala Gly Met Ser Val
                325                 330                 335 cag ccc aaa aac tgg cta cct gga ccc tgt tat cgg cag cag cgc gtt   1056
Gln Pro Lys Asn Trp Leu Pro Gly Pro Cys Tyr Arg Gln Gln Arg Val
            340                 345                 350 tct aaa aca aaa aca gac aac aac aac agc aat ttt acc tgg act ggt   1104
Ser Lys Thr Lys Thr Asp Asn Asn Asn Ser Asn Phe Thr Trp Thr Gly
        355                 360                 365 gct tca aaa tat aac ctc aat ggg cgt gaa tcc atc atc aac cct ggc   1152
Ala Ser Lys Tyr Asn Leu Asn Gly Arg Glu Ser Ile Ile Asn Pro Gly
    370                 375                 380 act gct atg gcc tca cac aaa gac gac gaa gac aag ttc ttt ccc atg   1200
Thr Ala Met Ala Ser His Lys Asp Asp Glu Asp Lys Phe Phe Pro Met
385                 390                 395                 400 agc ggt gtc atg att ttt gga aaa gag agc gcc gga gct tca aac act   1248
Ser Gly Val Met Ile Phe Gly Lys Glu Ser Ala Gly Ala Ser Asn Thr
                405                 410                 415 gca ttg gac aat gtc atg att aca gac gaa gag gaa att aaa gcc act   1296
Ala Leu Asp Asn Val Met Ile Thr Asp Glu Glu Glu Ile Lys Ala Thr
            420                 425                 430 aac cct gtg gcc acc gaa aga ttt ggg acc gtg gca gtc aat ttc cag   1344
Asn Pro Val Ala Thr Glu Arg Phe Gly Thr Val Ala Val Asn Phe Gln
        435                 440                 445
```

-continued

```
agc agc agc aca gac cct gcg acc gga gat gtg cat gct atg gga gca    1392
Ser Ser Ser Thr Asp Pro Ala Thr Gly Asp Val His Ala Met Gly Ala
    450                 455                 460 tta cct ggc atg gtg tgg caa gat aga gac gtg tac ctg cag ggt ccc    1440
Leu Pro Gly Met Val Trp Gln Asp Arg Asp Val Tyr Leu Gln Gly Pro
465                 470                 475                 480 att tgg gcc aaa att cct cac aca gat gga cac ttt cac ccg tct cct    1488
Ile Trp Ala Lys Ile Pro His Thr Asp Gly His Phe His Pro Ser Pro
                485                 490                 495 ctt atg ggc ggc ttt gga ctc aag aac ccg cct cct cag atc ctc atc    1536
Leu Met Gly Gly Phe Gly Leu Lys Asn Pro Pro Pro Gln Ile Leu Ile
            500                 505                 510 aaa aac acg cct gtt cct gcg aat cct ccg gcg gag ttt tca gct aca    1584
Lys Asn Thr Pro Val Pro Ala Asn Pro Pro Ala Glu Phe Ser Ala Thr
        515                 520                 525 aag ttt gct tca ttc atc acc caa tac tcc aca gga caa gtg agt gtg    1632
Lys Phe Ala Ser Phe Ile Thr Gln Tyr Ser Thr Gly Gln Val Ser Val
    530                 535                 540 gaa att gaa tgg gag ctg cag aaa gaa aac agc aag cgc tgg aat ccc    1680
Glu Ile Glu Trp Glu Leu Gln Lys Glu Asn Ser Lys Arg Trp Asn Pro
545                 550                 555                 560 gaa gtg cag tac aca tcc aat tat gca aaa tct gcc aac gtt gat ttt    1728
Glu Val Gln Tyr Thr Ser Asn Tyr Ala Lys Ser Ala Asn Val Asp Phe
                565                 570                 575 act gtg gac aac aat gga ctt tat act gag cct cgc ccc att ggc acc    1776
Thr Val Asp Asn Asn Gly Leu Tyr Thr Glu Pro Arg Pro Ile Gly Thr
            580                 585                 590 cgt tac ctt acc cgt ccc ctg taa                                    1800
Arg Tyr Leu Thr Arg Pro Leu
        595

<210> SEQ ID NO 15
<211> LENGTH: 599
<212> TYPE: PRT
<213> ORGANISM: AAV-1

<400> SEQUENCE: 15

Thr Ala Pro Gly Lys Lys Arg Pro Val Glu Gln Ser Pro Gln Glu Pro
1               5                   10                  15

Asp Ser Ser Ser Gly Ile Gly Lys Thr Gly Gln Gln Pro Ala Lys Lys
            20                  25                  30

Arg Leu Asn Phe Gly Gln Thr Gly Asp Ser Glu Ser Val Pro Asp Pro
        35                  40                  45

Gln Pro Leu Gly Glu Pro Pro Ala Thr Pro Ala Ala Val Gly Pro Thr
    50                  55                  60

Thr Met Ala Ser Gly Gly Gly Ala Pro Met Ala Asp Asn Asn Glu Gly
65                  70                  75                  80

Ala Asp Gly Val Gly Asn Ala Ser Gly Asn Trp His Cys Asp Ser Thr
                85                  90                  95

Trp Leu Gly Asp Arg Val Ile Thr Thr Ser Thr Arg Thr Trp Ala Leu
            100                 105                 110

Pro Thr Tyr Asn Asn His Leu Tyr Lys Gln Ile Ser Ser Ala Ser Thr
        115                 120                 125

Gly Ala Ser Asn Asp Asn His Tyr Phe Gly Tyr Ser Thr Pro Trp Gly
    130                 135                 140

Tyr Phe Asp Phe Asn Arg Phe His Cys His Phe Ser Pro Arg Asp Trp
145                 150                 155                 160
```

```
Gln Arg Leu Ile Asn Asn Asn Trp Gly Phe Arg Pro Lys Arg Leu Asn
            165                 170                 175
Phe Lys Leu Phe Asn Ile Gln Val Lys Glu Val Thr Thr Asn Asp Gly
        180                 185                 190
Val Thr Thr Ile Ala Asn Asn Leu Thr Ser Thr Val Gln Val Phe Ser
            195                 200                 205
Asp Ser Glu Tyr Gln Leu Pro Tyr Val Leu Gly Ser Ala His Gln Gly
210                 215                 220
Cys Leu Pro Pro Phe Pro Ala Asp Val Phe Met Ile Pro Gln Tyr Gly
225                 230                 235                 240
Tyr Leu Thr Leu Asn Asn Gly Ser Gln Ala Val Gly Arg Ser Ser Phe
                245                 250                 255
Tyr Cys Leu Glu Tyr Phe Pro Ser Gln Met Leu Arg Thr Gly Asn Asn
            260                 265                 270
Phe Thr Phe Ser Tyr Thr Phe Glu Glu Val Pro Phe His Ser Ser Tyr
        275                 280                 285
Ala His Ser Gln Ser Leu Asp Arg Leu Met Asn Pro Leu Ile Asp Gln
            290                 295                 300
Tyr Leu Tyr Tyr Leu Asn Arg Thr Gln Asn Gln Ser Gly Ser Ala Gln
305                 310                 315                 320
Asn Lys Asp Leu Leu Phe Ser Arg Gly Ser Pro Ala Gly Met Ser Val
                325                 330                 335
Gln Pro Lys Asn Trp Leu Pro Gly Pro Cys Tyr Arg Gln Gln Arg Val
            340                 345                 350
Ser Lys Thr Lys Thr Asp Asn Asn Asn Ser Asn Phe Thr Trp Thr Gly
        355                 360                 365
Ala Ser Lys Tyr Asn Leu Asn Gly Arg Glu Ser Ile Ile Asn Pro Gly
            370                 375                 380
Thr Ala Met Ala Ser His Lys Asp Asp Glu Asp Lys Phe Phe Pro Met
385                 390                 395                 400
Ser Gly Val Met Ile Phe Gly Lys Glu Ser Ala Gly Ala Ser Asn Thr
                405                 410                 415
Ala Leu Asp Asn Val Met Ile Thr Asp Glu Glu Glu Ile Lys Ala Thr
            420                 425                 430
Asn Pro Val Ala Thr Glu Arg Phe Gly Thr Val Ala Val Asn Phe Gln
        435                 440                 445
Ser Ser Ser Thr Asp Pro Ala Thr Gly Asp Val His Ala Met Gly Ala
            450                 455                 460
Leu Pro Gly Met Val Trp Gln Asp Arg Asp Val Tyr Leu Gln Gly Pro
465                 470                 475                 480
Ile Trp Ala Lys Ile Pro His Thr Asp Gly His Phe His Pro Ser Pro
                485                 490                 495
Leu Met Gly Gly Phe Gly Leu Lys Asn Pro Pro Gln Ile Leu Ile
            500                 505                 510
Lys Asn Thr Pro Val Pro Ala Asn Pro Ala Glu Phe Ser Ala Thr
        515                 520                 525
Lys Phe Ala Ser Phe Ile Thr Gln Tyr Ser Thr Gly Gln Val Ser Val
530                 535                 540
Glu Ile Glu Trp Glu Leu Gln Lys Glu Asn Ser Lys Arg Trp Asn Pro
545                 550                 555                 560
Glu Val Gln Tyr Thr Ser Asn Tyr Ala Lys Ser Ala Asn Val Asp Phe
                565                 570                 575
Thr Val Asp Asn Asn Gly Leu Tyr Thr Glu Pro Arg Pro Ile Gly Thr
```

-continued

```
                580                 585                 590
Arg Tyr Leu Thr Arg Pro Leu
        595

<210> SEQ ID NO 16
<211> LENGTH: 1605
<212> TYPE: DNA
<213> ORGANISM: AAV-1
<220> FEATURE:
<221> NAME/KEY: CDS
<222> LOCATION: (1)..(1602)
<223> OTHER INFORMATION:

<400> SEQUENCE: 16 atg gct tca ggc ggt ggc gca cca atg gca gac aat aac gaa ggc gcc    48
Met Ala Ser Gly Gly Gly Ala Pro Met Ala Asp Asn Asn Glu Gly Ala
1               5                  10                  15 gac gga gtg ggt aat gcc tca gga aat tgg cat tgc gat tcc aca tgg    96
Asp Gly Val Gly Asn Ala Ser Gly Asn Trp His Cys Asp Ser Thr Trp
            20                  25                  30 ctg ggc gac aga gtc atc acc acc agc acc cgc acc tgg gcc ttg ccc   144
Leu Gly Asp Arg Val Ile Thr Thr Ser Thr Arg Thr Trp Ala Leu Pro
        35                  40                  45 acc tac aat aac cac ctc tac aag caa atc tcc agt gct tca acg ggg   192
Thr Tyr Asn Asn His Leu Tyr Lys Gln Ile Ser Ser Ala Ser Thr Gly
    50                  55                  60 gcc agc aac gac aac cac tac ttc ggc tac agc acc ccc tgg ggg tat   240
Ala Ser Asn Asp Asn His Tyr Phe Gly Tyr Ser Thr Pro Trp Gly Tyr
65                  70                  75                  80 ttt gat ttc aac aga ttc cac tgc cac ttt tca cca cgt gac tgg cag   288
Phe Asp Phe Asn Arg Phe His Cys His Phe Ser Pro Arg Asp Trp Gln
                85                  90                  95 cga ctc atc aac aac aat tgg gga ttc cgg ccc aag aga ctc aac ttc   336
Arg Leu Ile Asn Asn Asn Trp Gly Phe Arg Pro Lys Arg Leu Asn Phe
            100                 105                 110 aaa ctc ttc aac atc caa gtc aag gag gtc acg acg aat gat ggc gtc   384
Lys Leu Phe Asn Ile Gln Val Lys Glu Val Thr Thr Asn Asp Gly Val
        115                 120                 125 aca acc atc gct aat aac ctt acc agc acg gtt caa gtc ttc tcg gac   432
Thr Thr Ile Ala Asn Asn Leu Thr Ser Thr Val Gln Val Phe Ser Asp
    130                 135                 140 tcg gag tac cag ctt ccg tac gtc ctc ggc tct gcg cac cag ggc tgc   480
Ser Glu Tyr Gln Leu Pro Tyr Val Leu Gly Ser Ala His Gln Gly Cys
145                 150                 155                 160 ctc cct ccg ttc ccg gcg gac gtg ttc atg att ccg caa tac ggc tac   528
Leu Pro Pro Phe Pro Ala Asp Val Phe Met Ile Pro Gln Tyr Gly Tyr
                165                 170                 175 ctg acg ctc aac aat ggc agc caa gcc gtg gga cgt tca tcc ttt tac   576
Leu Thr Leu Asn Asn Gly Ser Gln Ala Val Gly Arg Ser Ser Phe Tyr
            180                 185                 190 tgc ctg gaa tat ttc cct tct cag atg ctg aga acg ggc aac aac ttt   624
Cys Leu Glu Tyr Phe Pro Ser Gln Met Leu Arg Thr Gly Asn Asn Phe
        195                 200                 205 acc ttc agc tac acc ttt gag gaa gtg cct ttc cac agc agc tac gcg   672
Thr Phe Ser Tyr Thr Phe Glu Glu Val Pro Phe His Ser Ser Tyr Ala
    210                 215                 220 cac agc cag agc ctg gac cgg ctg atg aat cct ctc atc gac caa tac   720
His Ser Gln Ser Leu Asp Arg Leu Met Asn Pro Leu Ile Asp Gln Tyr
225                 230                 235                 240 ctg tat tac ctg aac aga act caa aat cag tcc gga agt gcc caa aac   768
Leu Tyr Tyr Leu Asn Arg Thr Gln Asn Gln Ser Gly Ser Ala Gln Asn
```

```
                    245                 250                 255
aag gac ttg ctg ttt agc cgt ggg tct cca gct ggc atg tct gtt cag       816
Lys Asp Leu Leu Phe Ser Arg Gly Ser Pro Ala Gly Met Ser Val Gln
            260                 265                 270 ccc aaa aac tgg cta cct gga ccc tgt tat cgg cag cag cgc gtt tct       864
Pro Lys Asn Trp Leu Pro Gly Pro Cys Tyr Arg Gln Gln Arg Val Ser
        275                 280                 285 aaa aca aaa aca gac aac aac aac agc aat ttt acc tgg act ggt gct       912
Lys Thr Lys Thr Asp Asn Asn Asn Ser Asn Phe Thr Trp Thr Gly Ala
    290                 295                 300 tca aaa tat aac ctc aat ggg cgt gaa tcc atc atc aac cct ggc act       960
Ser Lys Tyr Asn Leu Asn Gly Arg Glu Ser Ile Ile Asn Pro Gly Thr
305                 310                 315                 320 gct atg gcc tca cac aaa gac gac gaa gac aag ttc ttt ccc atg agc      1008
Ala Met Ala Ser His Lys Asp Asp Glu Asp Lys Phe Phe Pro Met Ser
                325                 330                 335 ggt gtc atg att ttt gga aaa gag agc gcc gga gct tca aac act gca      1056
Gly Val Met Ile Phe Gly Lys Glu Ser Ala Gly Ala Ser Asn Thr Ala
            340                 345                 350 ttg gac aat gtc atg att aca gac gaa gag gaa att aaa gcc act aac      1104
Leu Asp Asn Val Met Ile Thr Asp Glu Glu Glu Ile Lys Ala Thr Asn
        355                 360                 365 cct gtg gcc acc gaa aga ttt ggg acc gtg gca gtc aat ttc cag agc      1152
Pro Val Ala Thr Glu Arg Phe Gly Thr Val Ala Val Asn Phe Gln Ser
    370                 375                 380 agc agc aca gac cct gcg acc gga gat gtg cat gct atg gga gca tta      1200
Ser Ser Thr Asp Pro Ala Thr Gly Asp Val His Ala Met Gly Ala Leu
385                 390                 395                 400 cct ggc atg gtg tgg caa gat aga gac gtg tac ctg cag ggt ccc att      1248
Pro Gly Met Val Trp Gln Asp Arg Asp Val Tyr Leu Gln Gly Pro Ile
                405                 410                 415 tgg gcc aaa att cct cac aca gat gga cac ttt cac ccg tct cct ctt      1296
Trp Ala Lys Ile Pro His Thr Asp Gly His Phe His Pro Ser Pro Leu
            420                 425                 430 atg ggc ggc ttt gga ctc aag aac ccg cct cct cag atc ctc atc aaa      1344
Met Gly Gly Phe Gly Leu Lys Asn Pro Pro Pro Gln Ile Leu Ile Lys
        435                 440                 445 aac acg cct gtt cct gcg aat cct ccg gcg gag ttt tca gct aca aag      1392
Asn Thr Pro Val Pro Ala Asn Pro Pro Ala Glu Phe Ser Ala Thr Lys
    450                 455                 460 ttt gct tca ttc atc acc caa tac tcc aca gga caa gtg agt gtg gaa      1440
Phe Ala Ser Phe Ile Thr Gln Tyr Ser Thr Gly Gln Val Ser Val Glu
465                 470                 475                 480 att gaa tgg gag ctg cag aaa gaa aac agc aag cgc tgg aat ccc gaa      1488
Ile Glu Trp Glu Leu Gln Lys Glu Asn Ser Lys Arg Trp Asn Pro Glu
                485                 490                 495 gtg cag tac aca tcc aat tat gca aaa tct gcc aac gtt gat ttt act      1536
Val Gln Tyr Thr Ser Asn Tyr Ala Lys Ser Ala Asn Val Asp Phe Thr
            500                 505                 510 gtg gac aac aat gga ctt tat act gag cct cgc ccc att ggc acc cgt      1584
Val Asp Asn Asn Gly Leu Tyr Thr Glu Pro Arg Pro Ile Gly Thr Arg
        515                 520                 525 tac ctt acc cgt ccc ctg taa                                          1605
Tyr Leu Thr Arg Pro Leu
    530

<210> SEQ ID NO 17
<211> LENGTH: 534
<212> TYPE: PRT
<213> ORGANISM: AAV-1
```

<400> SEQUENCE: 17

```
Met Ala Ser Gly Gly Ala Pro Met Ala Asp Asn Asn Glu Gly Ala
1               5                   10                  15

Asp Gly Val Gly Asn Ala Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Ala Ser Thr Gly
    50                  55                  60

Ala Ser Asn Asp Asn His Tyr Phe Gly Tyr Ser Thr Pro Trp Gly Tyr
65                  70                  75                  80

Phe Asp Phe Asn Arg Phe His Cys His Phe Ser Pro Arg Asp Trp Gln
                85                  90                  95

Arg Leu Ile Asn Asn Asn Trp Gly Phe Arg Pro Lys Arg Leu Asn Phe
            100                 105                 110

Lys Leu Phe Asn Ile Gln Val Lys Glu Val Thr Thr Asn Asp Gly Val
        115                 120                 125

Thr Thr Ile Ala Asn Asn Leu Thr Ser Thr Val Gln Val Phe Ser Asp
    130                 135                 140

Ser Glu Tyr Gln Leu Pro Tyr Val Leu Gly Ser Ala His Gln Gly Cys
145                 150                 155                 160

Leu Pro Pro Phe Pro Ala Asp Val Phe Met Ile Pro Gln Tyr Gly Tyr
                165                 170                 175

Leu Thr Leu Asn Asn Gly Ser Gln Ala Val Gly Arg Ser Ser Phe Tyr
            180                 185                 190

Cys Leu Glu Tyr Phe Pro Ser Gln Met Leu Arg Thr Gly Asn Asn Phe
        195                 200                 205

Thr Phe Ser Tyr Thr Phe Glu Glu Val Pro Phe His Ser Ser Tyr Ala
    210                 215                 220

His Ser Gln Ser Leu Asp Arg Leu Met Asn Pro Leu Ile Asp Gln Tyr
225                 230                 235                 240

Leu Tyr Tyr Leu Asn Arg Thr Gln Asn Gln Ser Gly Ser Ala Gln Asn
                245                 250                 255

Lys Asp Leu Leu Phe Ser Arg Gly Ser Pro Ala Gly Met Ser Val Gln
            260                 265                 270

Pro Lys Asn Trp Leu Pro Gly Pro Cys Tyr Arg Gln Gln Arg Val Ser
        275                 280                 285

Lys Thr Lys Thr Asp Asn Asn Asn Ser Asn Phe Thr Trp Thr Gly Ala
    290                 295                 300

Ser Lys Tyr Asn Leu Asn Gly Arg Glu Ser Ile Ile Asn Pro Gly Thr
305                 310                 315                 320

Ala Met Ala Ser His Lys Asp Asp Glu Asp Lys Phe Phe Pro Met Ser
                325                 330                 335

Gly Val Met Ile Phe Gly Lys Glu Ser Ala Gly Ala Ser Asn Thr Ala
            340                 345                 350

Leu Asp Asn Val Met Ile Thr Asp Glu Glu Glu Ile Lys Ala Thr Asn
        355                 360                 365

Pro Val Ala Thr Glu Arg Phe Gly Thr Val Ala Val Asn Phe Gln Ser
    370                 375                 380

Ser Ser Thr Asp Pro Ala Thr Gly Asp Val His Ala Met Gly Ala Leu
385                 390                 395                 400

Pro Gly Met Val Trp Gln Asp Arg Asp Val Tyr Leu Gln Gly Pro Ile
```

```
                405                 410                 415
Trp Ala Lys Ile Pro His Thr Asp Gly His Phe His Pro Ser Pro Leu
            420                 425                 430
Met Gly Gly Phe Gly Leu Lys Asn Pro Pro Gln Ile Leu Ile Lys
            435                 440                 445
Asn Thr Pro Val Pro Ala Asn Pro Pro Ala Glu Phe Ser Ala Thr Lys
    450                 455                 460
Phe Ala Ser Phe Ile Thr Gln Tyr Ser Thr Gly Gln Val Ser Val Glu
465                 470                 475                 480
Ile Glu Trp Glu Leu Gln Lys Glu Asn Ser Lys Arg Trp Asn Pro Glu
            485                 490                 495
Val Gln Tyr Thr Ser Asn Tyr Ala Lys Ser Ala Asn Val Asp Phe Thr
            500                 505                 510
Val Asp Asn Asn Gly Leu Tyr Thr Glu Pro Arg Pro Ile Gly Thr Arg
            515                 520                 525
Tyr Leu Thr Arg Pro Leu
    530

<210> SEQ ID NO 18
<211> LENGTH: 4681
<212> TYPE: DNA
<213> ORGANISM: AAV-2

<400> SEQUENCE: 18
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcctggagg ggtggagtcg tgacgtgaat tacgtcatag    180
ggttagggag gtcctgtatt agaggtcacg tgagtgtttt gcgacatttt gcgacaccat    240
gtggtcacgc tgggtattta agcccgagtg agcacgcagg gtctccattt tgaagcggga    300
ggtttgaacg cgcagccgcc atgccggggt tttacgagat tgtgattaag gtccccagcg    360
accttgacgg gcatctgccc ggcatttctg acagctttgt gaactgggtg gccgagaagg    420
aatgggagtt gccgccagat tctgacatgg atctgaatct gattgagcag caccccctga    480
ccgtggccga aagctgcag gcgacttttc tgacggaatg cgccgtgtg agtaaggccc     540 cggaggcct tttctttgtg caatttgaga agggagagag ctacttccac atgcacgtgc    600
tcgtggaaac caccggggtg aaatccatgg ttttgggacg ttttcctgagt cagattcgcg    660 aaaaactgat tcagagaatt taccgcggga tcgagccgac tttgccaaac tggttcgcgg    720
tcacaaagac cagaaatggc gccggaggcg ggaacaaggt ggtggatgag tgctacatcc    780
ccaattactt gctccccaaa acccagcctg agctccagtg ggcgtggact aatatggaac    840
agtatttaag cgcctgtttg aatctcacgg agcgtaaacg gttggtggcg cagcatctga    900
cgcacgtgtc gcagacgcag gagcagaaca aagagaatca gaatcccaat tctgatgcgc    960
cggtgatcag atcaaaaact tcagccaggt acatggagct ggtcgggtgg ctcgtggaca   1020 agggattac ctcggagaag cagtggatcc aggaggacca ggcctcatac atctccttca   1080
atgcggcctc caactcgcgg tcccaaatca aggctgcctt ggacaatgcg ggaaagatta   1140
tgagcctgac taaaaccgcc cccgactacc tggtgggcca gcagccgtg gaggacattt   1200 ccagcaatcg gatttataaa attttggaac taaacgggta cgatcccaa tatgcggctt   1260 ccgtcttttct gggatgggcc acgaaaaagt tcggcaagag gaacaccatc tggctgtttg   1320
ggcctgcaac taccgggaag accaacatcg cggaggccat agcccacact gtgcccttct   1380
```

-continued

```
acgggtgcgt aaactggacc aatgagaact ttcccttcaa cgactgtgtc gacaagatgg   1440
tgatctggtg ggaggagggg aagatgaccg ccaaggtcgt ggagtcggcc aaagccattc   1500
tcggaggaag caaggtgcgc gtggaccaga aatgcaagtc ctcggcccag atagacccga   1560
ctcccgtgat cgtcacctcc aacaccaaca tgtgcgccgt gattgacggg aactcaacga   1620
ccttcgaaca ccagcagccg ttgcaagacc ggatgttcaa atttgaactc acccgccgtc   1680
tggatcatga ctttgggaag gtcaccaagc aggaagtcaa agacttttc cggtgggcaa    1740 aggatcacgt ggttgaggtg gagcatgaat tctacgtcaa aaagggtgga gccaagaaaa   1800
gacccgcccc cagtgacgca gatataagtg agcccaaacg ggtgcgcgag tcagttgcgc   1860
agccatcgac gtcagacgcg gaagcttcga tcaactacgc agacaggtac caaaacaaat   1920
gttctcgtca cgtgggcatg aatctgatgc tgtttccctg cagacaatgc gagagaatga   1980
atcagaattc aaatatctgc ttcactcacg gacagaaaga ctgtttagag tgctttcccg   2040
tgtcagaatc tcaaccggtt tctgtcgtca aaaaggcgta tcagaaactg tgctacattc   2100
atcatatcat gggaaaggtg ccagacgctt gcactgcctg cgatctggtc aatgtggatt   2160
tggatgactg catctttgaa caataaatga tttaaatcag gtatggctgc cgatggttat   2220
cttccagatt ggctcgagga cactctctct gaaggaataa gacagtggtg gaagctcaaa   2280
cctggcccac caccaccaaa gcccgcagag cggcataagg acgacagcag gggtcttgtg   2340
cttcctgggt acaagtacct cggacccttc aacggactcg acaagggaga gccggtcaac   2400
gaggcagacg ccgcggccct cgagcacgac aaagcctacg accggcagct cgacagcgga   2460
gacaacccgt acctcaagta caaccacgcc gacgcggagt tcaggagcg ccttaaagaa     2520 gatacgtctt ttggggggcaa cctcggacga gcagtcttcc aggcgaaaaa gagggttctt   2580
gaacctctcg gcctggttga ggaacctgtt aagacggctc cgggaaaaaa gaggccggta   2640
gagcactctc ctgtggagcc agactcctcc tcgggaaccg gaaagccggg ccagcagcct   2700
gcaagaaaaa gattgaattt tggtcagact ggagacgcag actcagtacc tgaccccag    2760 cctctcggac agccaccagc agcccctct ggtctgggaa ctaatacgat ggctacaggc     2820
agtggcgcac caatggcaga caataacgag ggcgccgacg gagtgggtaa ttcctccgga   2880
aattggcatt gcgattccac atggatgggc gacagagtca tcaccaccag cacccgaacc   2940
tgggccctgc ccacctacaa caaccacctc tacaaacaaa tttccagcca atcaggagcc   3000
tcgaacgaca atcactactt tggctacagc accccttggg ggtattttga cttcaacaga   3060
ttccactgcc acttttcacc acgtgactgg caaagactca tcaacaacaa ctggggattc   3120
cgacccaaga gactcaactt caacctcttt aacattcaag tcaaagaggt cacgcagaat   3180
gacggtacga cgacgattgc caataacctt accagcacgg ttcaggtgtt tactgactcg   3240
gagtaccagc tcccgtacgt cctcggctcg cgcatcaagg gatgcctccc gccgttccca   3300
gcagacgtct tcatggtgcc acagtatgga tacctcaccc tgaacaacgg gagtcaggca   3360
gtaggacgct cttcatttta ctgcctggag tactttcctt ctcagatgct gcgtaccgga   3420
aacaacttta ccttcagcta cacttttgag gacgttcctt tccacagcag ctacgctcac   3480
agccagagtc tggaccgtct catgaatcct ctcatcgacc agtacctgta ttacttgagc   3540
agaacaaaca ctccaagtgg aaccaccacg cagtcaaggc ttcagttttc tcaggcccca   3600
gccagtgaca ttcgggacca gtctaggaac tggcttcctg acccctgtta ccgccagcag   3660
cgagtatgaa agacatctgc ggataacaac aacagtgaat actcgtggac tggagctacc   3720
```

-continued

| | |
|---|---|
| aagtaccacc tcaatggcag agactctctg gtgaatccgg ggcccgccat ggcaagccac | 3780 |
| aaggacgatg aagaaaagtt ttttcctcag agcggggttc tcatctttgg gaagcaaggc | 3840 |
| tcagagaaaa caaatgtgaa cattgaaaag gtcatgatta cagacgaaga ggaaatccca | 3900 |
| acaaccaatc ccgtggctac ggagcagtat ggttctgtat ctaccaacct ccagagaggc | 3960 |
| aacagacaag cagctaccgc agatgtcaac acacaaggcg ttcttccagg catggtctgg | 4020 |
| caggacagag atgtgtacct tcaggggccc atctgggcaa agattccaca cacgacggga | 4080 |
| cattttcacc cctctcccct catgggtgga ttcggactta aacaccctcc tccacagatt | 4140 |
| ctcatcaaga acaccccggt acctgcgaat ccttcgacca ccttcagtgc ggcaaagttt | 4200 |
| gcttccttca tcacacagta ctccacggga cacggtcagc gtggagatcg agtgggagct | 4260 |
| gcagaacgaa aacagcaaac gctggaatcc cgaaattcag tacacttcca actacaacaa | 4320 |
| gtctgttaat cgtggacttt accgtggata ctaatggcgt gtattcagag cctcgcccca | 4380 |
| ttggcaccag atacctgact cgtaatctgt aattgcttgt taatcaataa accgtttaat | 4440 |
| tcgtttcagt tgaactttgg tctctgcgta tttctttctt atctagtttc catggctacg | 4500 |
| tagataagta gcatggcggg ttaatcatta actacaagga accctagtg atggagttgg | 4560 |
| ccactccctc tctgcgcgct cgctcgctca ctgaggccgg cgaccaaag gtcgcccgac | 4620 |
| gcccgggctt tgccccggcg gcctcagtga gcgagcgagc gcgcagagag ggagtgggca | 4680 |
| a | 4681 |

<210> SEQ ID NO 19
<211> LENGTH: 4683
<212> TYPE: DNA
<213> ORGANISM: AAV-6

<400> SEQUENCE: 19

| | |
|---|---|
| ttggccactc cctctctgcg cgctcgctcg ctcactgagg ccgggcgacc aaaggtcgcc | 60 |
| cgacgcccgg gctttgcccg gcggcctca gtgagcgagc gagcgcgcag agagggagtg | 120 |
| gccaactcca tcactagggg ttcctggagg ggtggagtcg tgacgtgaat tacgtcatag | 180 |
| ggttagggag gtcctgtatt agaggtcacg tgagtgtttt gcgacatttt gcgacaccat | 240 |
| gtggtcacgc tgggtattta agcccgagtg agcacgcagg gtctccattt tgaagcggga | 300 |
| ggtttgaacg cgcagcgcca tgccggggtt ttacgagatt gtgattaagg tccccagcga | 360 |
| ccttgacgag catctgcccg gcatttctga cagctttgtg aactgggtgg ccgagaagga | 420 |
| atgggagttg ccgccagatt ctgacatgga tctgaatctg attgagcagg caccccctgac | 480 |
| cgtggccgag aagctgcagc gcgacttcct ggtccactgg cgccgcgtga gtaaggcccc | 540 |
| ggaggccctc ttctttgttc agttcgagaa gggcgagtcc tacttccacc tccatattct | 600 |
| ggtggagacc acggggtca atccatggt gctgggccgc ttcctgagtc agattagcga | 660 |
| caagctggtg cagaccatct accgcgggat cgagccgacc ctgcccaact ggttcgcggt | 720 |
| gaccaagacg cgtaatggcg ccggaggggg gaacaaggtg gtggacgagt gctacatccc | 780 |
| caactacctc ctgcccaaga ctcagcccga gctgcagtgg gcgtggacta acatggagga | 840 |
| gtatataagc gcgtgtttaa acctggccga gcgcaaacgg ctcgtggcgc acgacctgac | 900 |
| ccacgtcagc cagacccagg agcagaacaa ggagaatctg aaccccaatt ctgacgcgcc | 960 |
| tgtcatccgg tcaaaaacct ccgcacgcta catggagctg gtcgggtggc tggtggaccg | 1020 |
| gggcatcacc tccgagaagc agtggatcca ggaggaccag gcctcgtaca tctccttcaa | 1080 |
| cgccgcctcc aactcgcggt cccagatcaa ggccgctctg gacaatgccg gcaagatcat | 1140 |

```
ggcgctgacc aaatccgcgc ccgactacct ggtaggcccc gctccgcccg ccgacattaa    1200
aaccaaccgc atttaccgca tcctggagct gaacggctac gaccctgcct acgccggctc    1260
cgtctttctc ggctgggccc agaaaaggtt cggaaaacgc aacaccatct ggctgtttgg    1320
gccggccacc acgggcaaga ccaacatcgc ggaagccatc gcccacgccg tgcccttcta    1380
cggctgcgtc aactggacca atgagaactt tcccttcaac gattgcgtcg acaagatggt    1440
gatctggtgg gaggagggca agatgacggc caaggtcgtg gagtccgcca aggccattct    1500
cggcggcagc aaggtgcgcg tggaccaaaa gtgcaagtcg tccgcccaga tcgatcccac    1560
ccccgtgatc gtcacctcca acaccaacat gtgcgccgtg attgacggga acagcaccac    1620
cttcgagcac cagcagccgt tgcaggaccg gatgttcaaa tttgaactca cccgccgtct    1680
ggagcatgac tttggcaagg tgacaaagca ggaagtcaaa gagttcttcc gctgggcgca    1740
ggatcacgtg accgaggtgg cgcatgagtt ctacgtcaga aagggtggag ccaacaacag    1800
acccgccccc gatgacgcgg ataaaagcga gcccaagcgg gcctgcccct cagtcgcgga    1860
tccatcgacg tcagacgcgg aaggagctcc ggtggacttt gccgacaggt accaaaacaa    1920
atgttctcgt cacgcgggca tgcttcagat gctgtttccc tgcaaaacat gcgagagaat    1980
gaatcagaat ttcaacattt gcttcacgca cgggaccaga gactgttcag aatgtttccc    2040
cggcgtgtca gaatctcaac cggtcgtcag aaagaggacg tatcggaaac tctgtgccat    2100
tcatcatctg ctggggcggg ctcccgagat tgcttgctcg gcctgcgatc tggtcaacgt    2160
ggatctggat gactgtgttt ctgagcaata aatgacttaa accaggtatg gctgccgatg    2220
gttatcttcc agattggctc gaggacaacc tctctgaggg cattcggcag tggtgggact    2280
tgaaacctgg agccccgaaa cccaaagcca accagcaaaa gcaggacgac ggccggggtc    2340
tggtgcttcc tggctacaag tacctcggac ccttcaacgg actcgacaag ggggagcccg    2400
tcaacgcggc ggatgcagcg gccctcgagc acgacaaggc ctacgaccag cagctcaaag    2460
cgggtgacaa tccgtacctg cggtataacc acgccgacgc cgagtttcag gagcgtctgc    2520
aagaagatac gtcttttggg ggcaacctcg gcgagcagt cttccaggcc aagaagaggg    2580
ttctcgaacc ttttggtctg gttgaggaag gtgctaagac ggctcctgga agaaacgtc    2640 cggtagagca gtcgccacaa gagccagact cctcctcggg cattggcaag acaggccagc    2700
agcccgctaa aaagagactc aatttttggtc agactgcga ctcagagtca gtccccgacc    2760
cacaacctct cggagaacct ccagcaaccc ccgctgctgt gggacctact acaatggctt    2820
caggcggtgg cgcaccaatg gcagacaata acgaaggcgc cgacggagtg ggtaatgcct    2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000
cgggggccag caacgacaac cactacttcg gctacagcac ccctggggg tatttttgatt    3060 tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttgt    3240
cggactcgga gtaccagttc ccgtacgtcc tcggctctgc gcaccagggc tgcctccctc    3300
cgttcccggc ggacgtgttc atgattccgc agtacggcta cctaacgctc aacaatggca    3360
gccaggcagt gggacgctca tccttttact gcctggaata tttcccatcg cagatgctga    3420
gaacgggcaa taactttacc ttcagctaca cccttcgagga cgtgccttc cacagcagct    3480
```

-continued

```
acgcgcacag ccagagcctg gaccggctga tgaatcctct catcgaccag tacctgtatt    3540
acctgaacag aactcacaat cagtccggaa gtgcccaaaa caaggacttg ctgtttagcc    3600
gtgggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg atttttggaa    3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
tggtgtggca agacagagac gtatacctgc agggtcctat ttgggccaaa attcctcaca    4080
cggatggaca ctttcacccg tctcctctca tgggcggctt tggacttaag cacccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggactttat actgagcctc    4380
gccccattgg cacccgttac ctcacccgtc ccctgtaatt gtgtgttaat caataaaccg    4440
gttaattcgt gtcagttgaa ctttggtctc atgtccttat tatcttatct ggtcaccata    4500
gcaaccggtt acacattaac tgcttagttg cgcttcgcga ataccctag tgatggagtt    4560 gcccactccc tctatgcgcg ctcgctcgct cggtggggcc ggcagagcag agctctgccg    4620
tctgcggacc tttggtccgc aggccccacc gagcgagcga gcgcgcatag agggagtggc    4680
caa                                                                  4683

<210> SEQ ID NO 20
<211> LENGTH: 16
<212> TYPE: DNA
<213> ORGANISM: rep binding motif

<400> SEQUENCE: 20
gctcgctcgc tcgctg                                                     16
```

ADENO-ASSOCIATED VIRUS SEROTYPE I NUCLEIC ACID SEQUENCES, VECTORS AND HOST CELLS CONTAINING SAME

CROSS-REFERENCE TO RELATED APPLICATIONS

This is a continuation of U.S. patent application Ser. No. 14/136,331, filed Dec. 20, 2013, which is a continuation of U.S. patent application Ser. No. 13/048,936, filed Mar. 16, 2011, now U.S. Pat. No. 8,637,255, which is a continuation of U.S. patent application Ser. No. 12/617,967, filed Nov. 13, 2009, now abandoned, which is a continuation of U.S. patent application Ser. No. 11/893,697, filed Aug. 17, 2007, now abandoned, which is a continuation of U.S. patent application Ser. No. 11/708,785, filed Feb. 20, 2007, now abandoned, which is a continuation of U.S. patent application Ser. No. 10/696,900, filed Oct. 30, 2003, now U.S. Pat. No. 7,186,552, which is a continuation of U.S. patent application Ser. No. 09/807,802, filed Nov. 29, 2001, now U.S. Pat. No. 6,759,237, which is a national stage under 35 USC 371 of PCT/US99/25694, filed Nov. 2, 1999, which claims the benefit under 35 USC 119(e) of the priority of U.S. Patent Application No. 60/107,114, filed Nov. 5, 1998.

U.S. patent application Ser. No. 11/893,697, filed Aug. 17, 2007, now abandoned, is also a continuation of U.S. patent application Ser. No. 11/430,226, filed May 8, 2006, now abandoned, which is a divisional of U.S. patent application Ser. No. 10/696,282, filed Oct. 29, 2003, now U.S. Pat. No. 7,105,345, which is a divisional of U.S. patent application Ser. No. 09/807,802, filed Nov. 29, 2001, now U.S. Pat. No. 6,759,237, which is a national stage of PCT/US99/25694, filed Nov. 2, 1999, which claims the benefit of the priority of U.S. Patent Application No. 60/107,114, filed Nov. 5, 1998.

STATEMENT REGARDING FEDERALLY SPONSORED RESEARCH OR DEVELOPMENT

This work was supported by the National Institutes of Health, grant no. P30 DK47757-06 and PO1 HD32649-04. The US government may have certain rights in this invention.

BACKGROUND OF THE INVENTION

This invention relates generally to viral vector, and more particularly, to recombinant viral vectors useful for gene delivery.

Adeno-associated viruses are small, single-stranded DNA viruses which require helper virus to facilitate efficient replication [K. I. Berns, *Parvoviridae: the viruses and their replication*, p. 1007-1041, in F. N. Fields et al., *Fundamental virology*, 3rd ed., vol. 2, (Lippencott-Raven Publishers, Philadelphia, Pa.) (1995)]. The 4.7 kb genome of AAV is characterized by two inverted terminal repeats (ITR) and two open reading frames which encode the Rep proteins and Cap proteins, respectively. The Rep reading frame encodes four proteins of molecular weight 78 kD, 68 kD, 52 kD and 40 kD. These proteins function mainly in regulating AAV replication and integration of the AAV into a host cell's chromosomes. The Cap reading frame encodes three structural proteins in molecular weight 85 kD (VP 1), 72 kD (VP2) and 61 kD (VP3) [Berns, cited above]. More than 80% of total proteins in AAV virion comprise VP3. The two ITRs are the only cis elements essential for AAV replication, packaging and integration. There are two conformations of AAV ITRs called "flip" and "flop". These differences in conformation originated from the replication model of adeno-associated virus which use the ITR to initiate and reinitiate the replication [R. O. Snyder et al., *J. Virol.*, 67:6096-6104 (1993); K. I. Berns, *Microbiological Reviews*, 54:316-329 (1990)].

AAVs have been found in many animal species, including primates, canine, fowl and human [F. A. Murphy et al., "The Classification and Nomenclature of Viruses: Sixth Report of the International Committee on Taxonomy of Viruses", *Archives of Virology*, (Springer-Verlag, Vienna) (1995)]. In addition to five known primate AAVs (AAV-1 to AAV-5), AAV-6, another serotype closely related to AAV-2 and AAV-1 has also been isolated [E. A. Rutledge et al., *J. Virol.*, 72:309-319 (1998)]. Among all known AAV serotypes, AAV-2 is perhaps the most well-characterized serotype, because its infectious clone was the first made [R. J. Samulski et al., *Proc. Natl. Acad. Sci. USA*, 79:2077-2081 (1982)]. Subsequently, the full sequences for AAV-3A, AAV-3B, AAV-4 and AAV-6 have also been determined [Rutledge, cited above; J. A. Chiorini et al., *J. Virol.*, 71:6823-6833 (1997); S. Muramatsu et al., *Virol.*, 221:208-217 (1996)]. Generally, all AAVs share more than 80% homology in nucleotide sequence.

A number of unique properties make AAV a promising vector for human gene therapy [Muzyczka, *Current Topics in Microbiology and Immunology*, 158:97-129 (1992)]. Unlike other viral vectors, AAVs have not been shown to be associated with any known human disease and are generally not considered pathogenic. Wild type AAV is capable of integrating into host chromosomes in a site specific manner [R. M. Kotin et al., *Proc. Natl. Acad. Sci. USA*, 87:2211-2215 (1990); R. J. Samulski, *EMBO J.*, 10(12):3941-3950 (1991)]. Recombinant AAV vectors can integrate into tissue cultured cells in chromosome 19 if the rep proteins are supplied in trans [C. Balague et al., *J. Virol.*, 71:3299-3306 (1997); R. T. Surosky et al., *J. Virol.*, 71:7951-7959 (1997)]. The integrated genomes of AAV have been shown to allow long term gene expression in a number of tissues, including, muscle, liver, and brain [K. J. Fisher, *Nature Med.*, 3(3): 306-312 (1997); R. 0. Snyder et al., *Nature Genetics*, 16:270-276 (1997); X. Xiao et al., *Experimental Neurology*, 144:113-124 (1997); Xiao, *J. Virol.*, 70(11):8098-8108 (1996)].

AAV-2 has been shown to be present in about 80-90% of the human population. Earlier studies showed that neutralizing antibodies for AAV-2 are prevalent [W. P. Parks et al., *J. Virol.*, 2:716-722 (1970)]. The presence of such antibodies may significantly decrease the usefulness of AAV vectors based on AAV-2 despite its other merits. What are needed in the art are vectors characterized by the advantages of AAV-2, including those described above, without the disadvantages, including the presence of neutralizing antibodies.

SUMMARY OF THE INVENTION

In one aspect, the invention provides an isolated AAV-1 nucleic acid molecule which is selected from among SEQ ID NO: 1, the strand complementary to SEQ ID NO: 1, and cDNA and RNA sequences complementary to SEQ ID NO: 1 and its complementary strand.

In another aspect, the present invention provides AAV ITR sequences, which include the 5' ITR sequences, nt 1 to 143 of SEQ ID NO: 1; the 3' ITR sequences, nt 4576 to 4718 of SEQ ID NO: 1, and fragments thereof.

In yet another aspect, the present invention provides a recombinant vector comprising an AAV-1 ITR and a selected transgene. Preferably, the vector comprises both the 5' and 3' AAV-1 ITRs between which the selected transgene is located.

In still another aspect, the invention provides a recombinant vector comprising an AAV-1 P5 promoter having the sequence of nt 236 to 299 of SEQ ID NO: 1 or a functional fragment thereof.

In a further aspect, the present invention provides a nucleic acid molecule encoding an AAV-1 rep coding region and an AAV-1 cap coding region.

In still another aspect, the present invention provides a host cell transduced with a recombinant viral vector of the invention. The invention further provides a host cell stably transduced with an AAV-1 P5 promoter of the invention.

In still a further aspect, the present invention provides a pharmaceutical composition comprising a carrier and a vector of the invention.

In yet another aspect, the present invention provides a method for AAV mediated delivery of a transgene to a host involving the step of delivering to a selected host a recombinant viral vector comprising a selected transgene under the control of sequences which direct expression thereof and an adeno-associated virus 1 (AAV-1) virion.

In another aspect, the invention provides a method for in vitro production of a selected gene product using a vector of the invention.

Other aspects and advantages of the invention will be readily apparent to one of skill in the art from the detailed description of the invention.

BRIEF DESCRIPTION OF THE DRAWINGS

FIGS. 1A-1F illustrate the alignment of nucleotides of AAV-1 [SEQ ID NO: 1], AAV-2 [SEQ ID NO: 18] and AAV-6 [SEQ ID NO: 19]. The alignment was done with MacVector 6.0. The full sequences of AAV-1 are shown in the top line. Nucleotides in AAV-2 and AAV-6 identical to AAV-1 are symbolized by "." and gaps by "-". Some of the conserved features among AAVs are marked in this figure. Note the 3' ITRs of AAV-1 and AAV-6 are shown in different orientations.

FIG. 2 illustrates the predicted secondary structure of AAV-1 ITR (nt 1-146 of SEQ ID NO:1). The nucleotides in AAV-2 (nt 1-144 of SEQ ID NO:18) and AAV-6 (nt 1-136 of SEQ ID NO:19) are shown in italic and bold respectively.

FIG. 4A is a bar chart illustrating expression levels of human alpha 1 anti-trypsin (α1AT) in serum following delivery of hAAT via recombinant AAV-1 and recombinant AAV-2 viruses.

DETAILED DESCRIPTION OF THE INVENTION

Figure 3A:
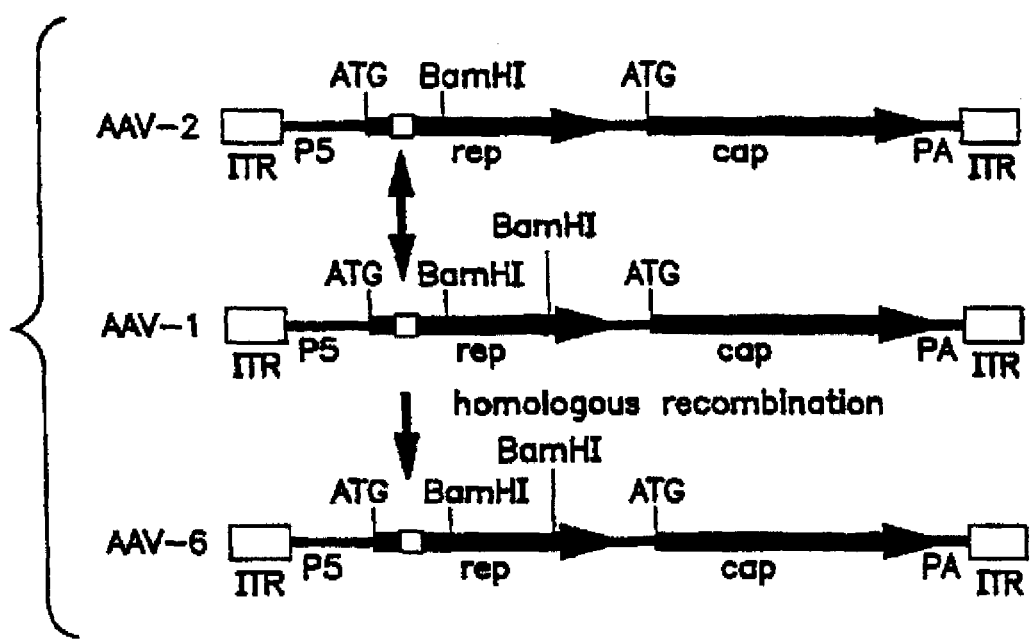
FIG. 3A illustrates a hypothesis of how AAV-6 arose from the homologous recombination between AAV-1 and AAV-2. The major elements of AAV-1 are indicated in the graph. A region that is shared between AAV-1, AAV-2 and AAV-6 is shown in box with waved lines.

The present invention provides novel nucleic acid sequences for an adeno-associated virus of serotype 1 (AAV-1). Also provided are fragments of these AAV-1 sequences. Among particularly desirable AAV-1 fragments are the inverted terminal repeat sequences (ITRs), rep and cap. Each of these fragments may be readily utilized, e.g., as a cassette, in a variety of vector systems and host cells. Such fragments may be used alone, in combination with other AAV-1 sequences or fragments, or in combination with elements from other AAV or non-AAV viral sequences. In one particularly desirable embodiment, a cassette may contain the AAV-1 ITRs of the invention flanking a selected transgene. In another desirable embodiment, a cassette may contain the AAV-1 rep and/or cap proteins, e.g., for use in producing recombinant (rAAV) virus.

Thus, the AAV-1 sequences and fragments thereof are useful in production of rAAV, and are also useful as antisense delivery vectors, gene therapy vectors, or vaccine vectors. The invention further provides nucleic acid molecules, gene delivery vectors, and host cells which contain the AAV-1 sequences of the invention. Also provided a novel methods of gene delivery using AAV vectors.

As described herein, the vectors of the invention containing the AAV-1 capsid proteins of the invention are particularly well suited for use in applications in which the neutralizing antibodies diminish the effectiveness of other AAV serotype based vectors, as well as other viral vectors. The rAAV vectors of the invention are particularly advantageous in rAAV readministration and repeat gene therapy.

These and other embodiments and advantages of the invention are described in more detail below. As used throughout this specification and the claims, the term "comprising" is inclusive of other components, elements, integers, steps and the like.

I. AAV1 Nucleic Acid and Protein Sequences

The AAV-1 nucleic acid sequences of the invention include the DNA sequences of SEQ ID NO: 1 (FIGS. 1A-1F), which consists of 4718 nucleotides. The AAV-1 nucleic acid sequences of the invention further encompass the strand which is complementary to SEQ ID NO: 1, as well as the RNA and cDNA sequences corresponding to SEQ ID NO: 1 and its complementary strand. Also included in the nucleic acid sequences of the invention are natural variants and engineered modifications of SEQ ID NO: 1 and its complementary strand. Such modifications include, for example, labels which are known in the art, methylation, and substitution of one or more of the naturally occurring nucleotides with an analog.

Further included in this invention are nucleic acid sequences which are greater than 85%, preferably at least about 90%, more preferably at least about 95%, and most preferably at least about 98-99% identical or homologous to SEQ ID NO:1.

The term "percent sequence identity" or "identical" in the context of nucleic acid sequences refers to the residues in the two sequences which are the same when aligned for maximum correspondence. The length of sequence identity comparison may be over the full-length sequence, or a fragment at least about nine nucleotides, usually at least about 20-24 nucleotides, at least about 28-32 nucleotides, and preferably at least about 36 or more nucleotides. There are a number of different algorithms known in the art which can be used to measure nucleotide sequence identity. For instance, polynucleotide sequences can be compared using Fasta, a program in GCG Version 6.1. Fasta provides alignments and percent sequence identity of the regions of the best overlap between the query and search sequences (Pearson, 1990, herein incorporated by reference). For instance, percent sequence identity between nucleic acid sequences can be determined using Fasta with its default parameters (a word size of 6 and the NOPAM factor for the scoring matrix) as provided in GCG Version 6.1, herein incorporated by reference.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 95-99% of the sequence.

Also included within the invention are fragments of SEQ ID NO: 1, its complementary strand, cDNA and RNA complementary thereto. Suitable fragments are at least 15 nucleotides in length, and encompass functional fragments which are of biological interest. Certain of these fragments may be identified by reference to FIGS. 1A-1F. Examples of particularly desirable functional fragments include the AAV-1 inverted terminal repeat (ITR) sequences of the invention. In contrast to the 145 nt ITRs of AAV-2, AAV-3, and AAV-4, the AAV-1 ITRs have been found to consist of only 143 nucleotides, yet advantageously are characterized by the T-shaped hairpin structure which is believed to be responsible for the ability of the AAV-2 ITRs to direct site-specific integration. In addition, AAV-1 is unique among other AAV serotypes, in that the 5' and 3' ITRs are identical. The full-length 5' ITR sequences of AAV-1 are provided at nucleotides 1-143 of SEQ ID NO: 1 (FIG. 1A) and the full-length 3' ITR sequences of AAV-1 are provided at nt 4576-4718 of SEQ ID NO: 1 (FIG. 1F). One of skill in the art can readily utilize less than the full-length 5' and/or 3' ITR sequences for various purposes and may construct modified ITRs using conventional techniques, e.g., as described for AAV-2 ITRs in Samulski et al, Cell, 33:135-143 (1983).

Another desirable functional fragment of the AAV-1 genome is the P5 promoter of AAV-1 which has sequences unique among AAV P5 promoters, while maintaining critical regulatory elements and functions. This promoter is located within nt 236-299 of SEQ ID NO: 1 (FIG. 1A). Other examples of functional fragments of interest include the sequences at the junction of the rep/cap, e.g., the sequences spanning nt 2306-2223, as well as larger fragments which encompass this junction which may comprise 50 nucleotides on either side of this junction. Still other examples of functional fragments include the sequences encoding the rep proteins. Rep 78 is located in the region of nt 334-2306 of SEQ ID NO: 1; Rep 68 is located in the region of nt 334-2272, and contains an intron spanning nt 1924-2220 of SEQ ID NO: 1. Rep 52 is located in the region of nt 1007-2304 of SEQ ID NO: 1; rep 40 is located in the region of nt 1007-2272, and contains an intron spanning nt 1924-2246 of SEQ ID NO: 1. Also of interest are the sequences encoding the capsid proteins, VP 1 [nt 2223-4431 of SEQ ID NO: 1], VP2 [nt 2634-4432 of SEQ ID NO: 1] and VP3 [nt 2829-4432 of SEQ ID NO: 1]. Other fragments of interest may include the AAV-1 P19 sequences, AAV-1 P40 sequences, the rep binding site, and the terminal resolute site (TRS).

The invention further provides the proteins and fragments thereof which are encoded by the AAV-1 nucleic acids of the invention. Particularly desirable proteins include the rep and cap proteins, which are encoded by the nucleotide sequences identified above. These proteins include rep 78 [SEQ ID NO:5], rep 68 [SEQ ID NO:7], rep 52 [SEQ ID NO:9], rep 40 [SEQ ID NO: 11], vp1 [SEQ ID NO: 13], vp2 [SEQ ID NO: 15], and vp3 [SEQ ID NO: 17] and functional fragments thereof while the sequences of the rep and cap proteins have been found to be closely related to those of AAV-6, there are differences in the amino acid sequences (see Table 1 below), as well as differences in the recognition of these proteins by the immune system. However, one of skill in the art may readily select other suitable proteins or protein fragments of biological interest. Suitably, such fragments are at least 8 amino acids in length. However, fragments of other desired lengths may be readily utilized. Such fragments may be produced recombinantly or by other suitable means, e.g., chemical synthesis.

The sequences, proteins, and fragments of the invention may be produced by any suitable means, including recombinant production, chemical synthesis, or other synthetic means. Such production methods are within the knowledge of those of skill in the art and are not a limitation of the present invention.

II. Viral Vectors

In another aspect, the present invention provides vectors which utilize the AAV-1 sequences of the invention, including fragments thereof, for delivery of a heterologous gene or other nucleic acid sequences to a target cell. Suitably, these heterologous sequences (i.e., a transgene) encode a protein or gene product which is capable of being expressed in the target cell. Such a transgene may be constructed in the form of a "minigene". Such a "minigene" includes selected heterologous gene sequences and the other regulatory elements necessary to transcribe the gene and express the gene product in a host cell. Thus, the gene sequences are operatively linked to regulatory components in a manner which permit their transcription. Such components include conventional regulatory elements necessary to drive expression of the transgene in a cell containing the viral vector. The minigene may also contain a selected promoter which is linked to the transgene and located, with other regulatory elements, within the selected viral sequences of the recombinant vector.

Selection of the promoter is a routine matter and is not a limitation of this invention. Useful promoters may be constitutive promoters or regulated (inducible) promoters, which will enable control of the timing and amount of the transgene to be expressed. For example, desirable promoters include the cytomegalovirus (CMV) immediate early promoter/enhancer [see, e.g., Boshart et al, *Cell*, 41:521-530 (1985)], the Rous sarcoma virus LTR promoter/enhancer, and the chicken cytoplasmic β-actin promoter [T. A. Kost et al, *Nucl. Acids Res.*, 11(23):8287 (1983)]. Still other desirable promoters are the albumin promoter and an AAV P5 promoter. Optionally, the selected promoter is used in conjunction with a heterologous enhancer, e.g., the β-actin promoter may be used in conjunction with the CMV enhancer. Yet other suitable or desirable promoters and enhancers may be selected by one of skill in the art.

The minigene may also desirably contain nucleic acid sequences heterologous to the viral vector sequences including sequences providing signals required for efficient polyadenylation of the transcript (poly-A or pA) and introns with functional splice donor and acceptor sites. A common poly-A sequence which is employed in the exemplary vectors of this invention is that derived from the papovavirus SV-40. The poly-A sequence generally is inserted in the minigene downstream of the transgene sequences and upstream of the viral vector sequences. A common intron sequence is also derived from SV-40, and is referred to as the SV40 T intron sequence. A minigene of the present invention may also contain such an intron, desirably located between the promoter/enhancer sequence and the transgene. Selection of these and other common vector elements are conventional [see, e.g., Sambrook et al, "Molecular Cloning. A Laboratory Manual", 2d edit., Cold Spring Harbor Laboratory, New York (1989) and references cited therein] and many such sequences are available from commercial and industrial sources as well as from Genbank.

The selection of the transgene is not a limitation of the present invention. Suitable transgenes may be readily selected from among desirable reporter genes, therapeutic genes, and optionally, genes encoding immunogenic polypeptides. Examples of suitable reporter genes include (3-galactosidase (β-gal), an alkaline phosphatase gene, and green fluorescent protein (GFP). Examples of therapeutic genes include, cytokines, growth factors, hormones, and differentiation factors, among others. The transgene may be readily selected by one of skill in the art. See, e.g., WO 98/09657, which identifies other suitable transgenes.

Suitably, the vectors of the invention contain, at a minimum, cassettes which consist of fragments of the AAV-1 sequences and proteins. In one embodiment, a vector of the invention comprises a selected transgene, which is flanked by a 5' ITR and a 3' ITR, at least one of which is an AAV-1 ITR of the invention. Suitably, vectors of the invention may contain a AAV-1 P5 promoter of the invention. In yet another embodiment, a plasmid or vector of the invention contains AAV-1 rep sequences. In still another embodiment, a plasmid or vector of the invention contains at least one of the AAV-1 cap proteins of the invention. Most suitably, these AAV-1-derived vectors are assembled into viral vectors, as described herein.

A. AAV Viral Vectors

In one aspect, the present invention provides a recombinant AAV-1 viral vector produced using the AAV-1 capsid proteins of the invention. The packaged rAAV-1 virions of the invention may contain, in addition to a selected minigene, other AAV-1 sequences, or may contain sequences from other AAV serotypes.

Methods of generating rAAV virions are well known and the selection of a suitable method is not a limitation on the present invention. See, e.g., K. Fisher et al, *J. Virol.*, 70:520-532 (1993) and U.S. Pat. No. 5,478,745. In one suitable method, a selected host cell is provided with the AAV sequence encoding a rep protein, the gene encoding the AAV cap protein and with the sequences for packaging and subsequent delivery. Desirably, the method utilizes the sequences encoding the AAV-1 rep and/or cap proteins of the invention.

In one embodiment, the rep/cap genes and the sequences for delivery are supplied by co-transfection of vectors carrying these genes and sequences. In one currently preferred embodiment, a cis (vector) plasmid, a trans plasmid containing the rep and cap genes, and a plasmid containing the adenovirus helper genes are co-transfected into a suitable cell line, e.g., 293. Alternatively, one or more of these functions may be provided in trans via separate vectors, or may be found in a suitably engineered packaging cell line.

An exemplary cis plasmid will contain, in 5' to 3' order, AAV 5' ITR, the selected transgene, and AAV 3' ITR. In one desirable embodiment, at least one of the AAV ITRs is a 143 nt AAV-1 ITR. However, other AAV serotype ITRs may be readily selected. Suitably, the full-length ITRs are utilized. However, one of skill in the art can readily prepare modified AAV ITRs using conventional techniques. Similarly, methods for construction of such plasmids is well known to those of skill in the art.

A trans plasmid for use in the production of the rAAV-1 virion particle may be prepared according to known techniques. In one desired embodiment, this plasmid contains the rep and cap proteins of AAV-1, or functional fragments thereof. Alternatively, the rep sequences may be from another selected AAV serotype.

The cis and trans plasmid may then be co-transfected with a wild-type helper virus (e.g., Ad2, Ad5, or a herpesvirus), or more desirably, a replication defective adenovirus, into a selected host cell. Alternatively, the cis and trans plasmid may be co-transfected into a selected host cell together with a transfected plasmid which provides the necessary helper functions. Selection of a suitable host cell is well within the skill of those in the art and include such mammalian cells as 293 cells, HeLa cells, among others.

Alternatively, the cis plasmid and, optionally the trans plasmid, may be transfected into a packaging cell line which provides the remaining helper functions necessary for production of a rAAV containing the desired AAV-1 sequences of the invention. An example of a suitable packaging cell line, where an AAV-2 capsid is desired, is B-50, which stably expresses AAV-2 rep and cap genes under the control of a homologous P5 promoter. This cell line is characterized by integration into the cellular chromosome of multiple copies (at least 5 copies) of P5-rep-cap gene cassettes in a concatomer form. This B-50 cell line was deposited with the American Type Culture Collection, 10801 University Boulevard, Manassas, Va. 20110-2209, on Sep. 18, 1997 under Accession No. CRL-12401 pursuant to the provisions of the Budapest Treaty. However, the present invention is not limited as to the selection of the packaging cell line.

Exemplary transducing vectors based on AAV-1 capsid proteins have been tested both in vivo and in vitro, as described in more detail in Example 4. In these studies, it was demonstrated that recombinant AAV vector with an AAV-1 virion can transduce both mouse liver and muscle. These, and other AAV-1 based gene therapy vectors which may be generated by one of skill in the art are beneficial for gene delivery to selected host cells and gene therapy patients since the neutralization antibodies of AAV-1 present in much of the human population exhibit different patterns from other AAV serotypes and therefore do not neutralize the AAV-1 virions. One of skill in the art may readily prepare other rAAV viral vectors containing the AAV-1 capsid proteins provided herein using a variety of techniques known to those of skill in the art. One may similarly prepare still other rAAV viral vectors containing AAV-1 sequence and AAV capsids of another serotype.

B. Other Viral Vectors

One of skill in the art will readily understand that the AAV-1 sequences of the invention can be readily adapted for use in these and other viral vector systems for in vitro, ex vivo or in vivo gene delivery. Particularly well suited for use in such viral vector systems are the AAV-1 ITR sequences, the AAV-1 rep, the AAV-1 cap, and the AAV-1 P5 promoter sequences.

For example, in one desirable embodiment, the AAV-1 ITR sequences of the invention may be used in an expression cassette which includes AAV-1 5' ITR, a non-AAV DNA sequences of interest (e.g., a minigene), and 3' ITR and which lacks functional rep/cap. Such a cassette containing an AAV-1 ITR may be located on a plasmid for subsequent transfection into a desired host cell, such as the cis plasmid described above. This expression cassette may further be provided with an AAV capsid of a selected serotype to permit infection of a cell or stably transfected into a desired host cell for packaging of rAAV virions. Such an expression cassette may be readily adapted for use in other viral systems, including adenovirus systems and lentivirus systems. Methods of producing Ad/AAV vectors are well known to those of skill in the art. One desirable method is described in PCT/US95/14018. However, the present invention is not limited to any particular method.

Another aspect of the present invention is the novel AAV-1 P5 promoter sequences which are located in the region spanning nt 236-299 of SEQ ID NO: 1. This promoter is useful in a variety of viral vectors for driving expression of a desired transgene.

Similarly, one of skill in the art can readily select other fragments of the AAV-1 genome of the invention for use in a variety of vector systems. Such vectors systems may include, e.g., lentiviruses, retroviruses, poxviruses, vaccinia viruses, and adenoviral systems, among others. Selection of these vector systems is not a limitation of the present invention.

C. Host Cells and Packaging Cell Lines

In yet another aspect, the present invention provides host cells which may be transiently transfected with AAV-1 nucleic acid sequences of the invention to permit expression of a desired transgene or production of a rAAV particle. For example, a selected host cell may be transfected with the AAV-1 P5 promoter sequences and/or the AAV-1 5' ITR sequences using conventional techniques. Providing AAV helper functions to the transfected cell lines of the invention results in packaging of the rAAV as infectious rAAV particles. Such cell lines may be produced in accordance with known techniques [see, e.g, U.S. Pat. No. 5,658,785], making use of the AAV-1 sequences of the invention.

Alternatively, host cells of the invention may be stably transfected with a rAAV expression cassette of the invention, and with copies of AAV-1 rep and cap genes. Suitable parental cell lines include mammalian cell lines and it may be desirable to select host cells from among non-simian mammalian cells. Examples of suitable parental cell lines include, without limitation, HeLa [ATCC CCL 2], A549 [ATCC Accession No. CCL 185], KB [CCL 17], Detroit [e.g., Detroit 510, CCL 72] and WI38 [CCL 75] cells. These cell lines are all available from the American Type Culture Collection, 10801 University Boulevard, Manassas, Va. 20110-2209 USA. Other suitable parent cell lines may be obtained from other sources and may be used to construct stable cell lines containing the P5 and/or AAV rep and cap sequences of the invention.

Recombinant vectors generated as described above are useful for delivery of the DNA of interest to cells.

III. Methods of Delivering Genes Via AAV-1 Derived Vectors

In another aspect, the present invention provides a method for delivery of a transgene to a host which involves transfecting or infecting a selected host cell with a recombinant viral vector generated with the AAV-1 sequences (or functional fragments thereof) of the invention. Methods for delivery are well known to those of skill in the art and are not a limitation of the present invention.

In one desirable embodiment, the invention provides a method for AAV-mediated delivery of a transgene to a host. This method involves transfecting or infecting a selected host cell with a recombinant viral vector containing a selected transgene under the control of sequences which direct expression thereof and AAV-1 capsid proteins.

Optionally, a sample from the host may be first assayed for the presence of antibodies to a selected AAV serotype. A variety of assay formats for detecting neutralizing antibodies are well known to those of skill in the art. The selection of such an assay is not a limitation of the present invention. See, e.g., Fisher et al, *Nature Med.*, 3(3):306-312 (March 1997) and W. C. Manning et al, *Human Gene Therapy*, 9:477-485 (Mar. 1, 1998). The results of this assay may be used to determine which AAV vector containing capsid proteins of a particular serotype are preferred for delivery, e.g., by the absence of neutralizing antibodies specific for that capsid serotype.

In one aspect of this method, the delivery of vector with AAV-1 capsid proteins may precede or follow delivery of a gene via a vector with a different serotype AAV capsid protein. Thus, gene delivery via rAAV vectors may be used for repeat gene delivery to a selected host cell. Desirably, subsequently administered rAAV vectors carry the same transgene as the first rAAV vector, but the subsequently administered vectors contain capsid proteins of serotypes which differ from the first vector. For example, if a first vector has AAV-2 capsid proteins, subsequently administered vectors may have capsid proteins selected from among the other serotypes, including AAV-1, AAV-3A, AAV-3B, AAV-4 and AAV-6.

Thus, a rAAV-1-derived recombinant viral vector of the invention provides an efficient gene transfer vehicle which can deliver a selected transgene to a selected host cell in vivo or ex vivo even where the organism has neutralizing antibodies to one or more AAV serotypes. These compositions are particularly well suited to gene delivery for therapeutic purposes. However, the compositions of the invention may also be useful in immunization. Further, the compositions of the invention may also be used for production of a desired gene product in vitro.

The above-described recombinant vectors may be delivered to host cells according to published methods. An AAV viral vector bearing the selected transgene may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The viral vectors are administered in sufficient amounts to transfect the cells and to provide sufficient levels of gene transfer and expression to provide a therapeutic benefit without undue adverse effects, or with medically acceptable physiological effects, which can be determined by those skilled in the medical arts. Conventional and pharmaceutically acceptable routes of administration include, but are not limited to, direct delivery to the liver, oral, intranasal, intravenous, intramuscular, subcutaneous, intradermal, and other parental routes of administration. Routes of administration may be combined, if desired.

Dosages of the viral vector will depend primarily on factors such as the condition being treated, the age, weight and health of the patient, and may thus vary among patients. For example, a therapeutically effective human dosage of the viral vector is generally in the range of from about 1 ml to about 100 ml of solution containing concentrations of from about $1\times10^9$ to $1\times10^{16}$ genomes virus vector. A preferred human dosage may be about $1\times10^{13}$ to $1\times10^{16}$ AAV genomes. The dosage will be adjusted to balance the therapeutic benefit against any side effects and such dosages may vary depending upon the therapeutic application for which the recombinant vector is employed. The levels of expression of the transgene can be monitored to determine the frequency of dosage resulting in viral vectors, preferably AAV vectors containing the minigene. Optionally, dosage regimens similar to those described for therapeutic purposes may be utilized for immunization using the compositions of the invention. For in vitro production, a desired protein may be obtained from a desired culture following transfection of host cells with a rAAV containing the gene encoding the desired protein and culturing the cell culture under conditions which permits expression. The expressed protein may then be purified and isolated, as desired. Suitable techniques for transfection, cell culturing, purification, and isolation are known to those of skill in the art.

The following examples illustrate several aspects and embodiments of the invention.

Example 1

Generation of Infectious Clone of AAV-1

The replicated form DNA of AAV-1 was extracted from 293 cells that were infected by AAV-1 and wild type adenovirus type 5.

A. Cell Culture and Virus

AAV-free 293 cells and 84-31 cells were provided by the human application laboratory of the University of Pennsylvania. These cells were cultured in Dulbecco's Modified Eagle Medium with 10% fetal bovine serum (Hyclone), penicillin (100 U/ml) and streptomycin at 37° C. in a moisturized environment supplied with 5% $CO_2$. The 84-31 cell line constitutively expresses adenovirus genes E1a, E1b, E4/ORF6, and has been described previously [K. J. Fisher, *J. Virol.*, 70:520-532 (1996)]. AAV-1 (ATCC VR-645) seed stock was purchased from American Type Culture Collection (ATCC, Manassas, Va.). AAV viruses were propagated in 293 cells with wild type Ad5 as a helper virus.

B. Recombinant AAV Generation

The recombinant AAV viruses were generated by transfection using an adenovirus free method. Briefly, the cis plasmid (with AAV ITR), trans plasmid (with AAV rep gene and cap gene) and helper plasmid (pFΔ13, with essential regions from the adenovirus genome) were simultaneously co-transfected into 293 cells in a ratio of 1:1:2 by calcium phosphate precipitation. The pFΔ13 helper plasmid has an 8 kb deletion in the adenovirus E2B region and has deletions in most of the late genes. This helper plasmid was generated by deleting the RsrII fragment from pFG140 (Microbix, Canada). Typically, 50 µg of DNA (cis:trans:PFA13 at ratios of 1:1:2, respectively) was transfected onto a 15 cm tissue culture dish. The cells were harvested 96 hours post-transfection, sonicated and treated with 0.5% sodium deoxycholate (37° C. for 10 min). Cell lysates were then subjected to two rounds of a CsCl gradient. Peak fractions containing AAV vector were collected, pooled, and dialyzed against PBS before injecting into animals. To make rAAV virus with AAV-1 virion, the pAV1H or p5E18 (2/1) was used as the trans plasmid to provide rep and cap function.

For the generation of rAAV based on AAV-2, p5E18 was used as the trans plasmid since it greatly improved the rAAV yield. This plasmid, p5E18(2/2), expresses AAV-2 Rep and Cap and contains a P5 promoter relocated to a position 3' to the Cap gene, thereby minimizing expression of Rep78 and Rep68. The strategy was initially described by Li et al, *J. Virol.*, 71:5236-5243 (1997). P5E18(2/2) was constructed in the following way. The previously described pMMTV-trans vector (i.e., the mouse mammary tumor virus promoter substituted for the P5 promoter in an AAV-2-based vector) was digested with SmaI and ClaI, filled in with the Klenow enzyme, and then recircularized with DNA ligase. The resulting construct was digested with XbaI, filled in, and ligated to the blunt-ended BamHI-XbaI fragment from pCR-p5, constructed in the following way. The P5 promoter of AAV was amplified by PCR and the amplified fragment was subsequently cloned into pCR2.1 (Invitrogen) to yield pCR-P5. The helper plasmid pAV1H was constructed by cloning the BfaI fragment of pAAV-2 into pBluescript II-SK(+) at the BcorV and SmaI sites. The 3.0-kb XbaI-KpnI fragment from p5E18(2/2), the 2.3-kb XbaI-KpnI fragment from pAV1H, and the 1.7-kb KpnI fragment from p5E18(2/2) were incorporated into a separate plasmid P5E18(2/1), which contains AAV-2 Rep, AAV-1 Cap, and the AAV-2 P5 promoter located 3' to the Cap gene. Plasmid p5E18(2/1) produced 10- to 20-fold higher quantities of the vector than pAV1H (i.e., $10^{12}$ genomes/50 15-cm² plates).

C. DNA Techniques

Hirt DNA extraction was performed as described in the art with minor modification [R. J. Samulski et al., *Cell*, 33:135-143 (1983)]. More particularly, Hirst solution without SDS was used instead of using original Hirt solution containing SDS. The amount of SDS present in the original Hirst solution was added after the cells had been fully suspended. To construct AAV-1 infectious clone, the Hirt DNA from AAV-1 infected 293 cells was repaired with Klenow enzyme (New England Biolabs) to ensure the ends were blunt. The treated AAV-1 Hirt DNA was then digested with BamHI and cloned into three vectors, respectively. The internal BamHI was cloned into pBlueScript II-SK+ cut with BamHI to get pAV1-BM. The left and right fragments were cloned into pBlueScript II-SK+ cut with BamHI+EcoRV to obtain pAV1-BL and pAV1-BR, respectively. The AAV sequence in these three plasmids were subsequently assembled into the same vector to get AAV-1 infectious clone pAAV-1. The helper plasmid for recombinant AAV-1 virus generation was constructed by cloning the Bfa I fragment of pAAV-1 into pBlueScript II-SK+ at the EcoRV site.

Analysis of the Hirt DNA revealed three bands, a dimer at 9.4 kb, a monomer at 4.7 kb and single-stranded DNA at 1.7 kb, which correlated to different replication forms of AAV-1. The monomer band was excised from the gel and then digested with BamHI. This resulted in three fragments of 1.1 kb, 0.8 kb and 2.8 kb. This pattern is in accordance with the description by Bantel-schaal and zur Hausen, *Virol.*, 134(1):52-63 (1984). The 1.1 kb and 2.8 kb BamHI fragments were cloned into pBlueScript-KS(+) at BamHI and EcoRV site. The internal 0.8 kb fragment was cloned into BamHI site of pBlueScript-KS(+).

These three fragments were then subcloned into the same construct to obtain a plasmid (pAAV-1) that contained the full sequence of AAV-1. The pAAV-1 was then tested for its ability to rescue from the plasmid backbone and package infectious virus. The pAAV-1 was then transfected to 293 cells and supplied with adenovirus type as helper at MOI 10. The virus supernatant was used to reinfect 293 cells.

For Southern blot analysis, Hirt DNA was digested with DpnI to remove bacteria-borne plasmid and probed with internal BamHI fragment of AAV-1. The membrane was then washed at high stringency conditions, which included: twice 30 minutes with 2×SSC, 0.1% SDS at 65° C. and twice 30 minutes with 0.1×SSC, 0.1% SDS at 65° C. The membrane was then analyzed by both phosphor image and X-ray autoradiography. The results confirmed that pAAV-1 is indeed an infectious clone of AAV serotype 1.

Example 2

Sequencing Analysis of AAV-1

The entire AAV-1 genome was then determined by automatic sequencing and was found to be 4718 nucleotides in length (FIGS. 1A-1F). For sequencing, an ABI 373 automatic sequencer as used to determine the sequences for all plasmids and PCR fragments related to this study using the FS dye chemistry. All sequences were confirmed by sequencing both plus and minus strands. These sequences were also confirmed by sequencing two independent clones of pAV-BM, pAV-BL and pAV-BR. Since the replicated form of AAV-1 DNA served as the template for sequence determination, these sequences were also confirmed by sequencing a series of PCR products using original AAV-1 seed stock as a template.

The length of AAV-1 was found to be within the range of the other serotypes: AAV-3 (4726 nucleotides), AAV-4 (4774 nucleotides), AAV-2 (4681 nucleotides), and AAV-6 (4683 nucleotides).

Figure 3B:
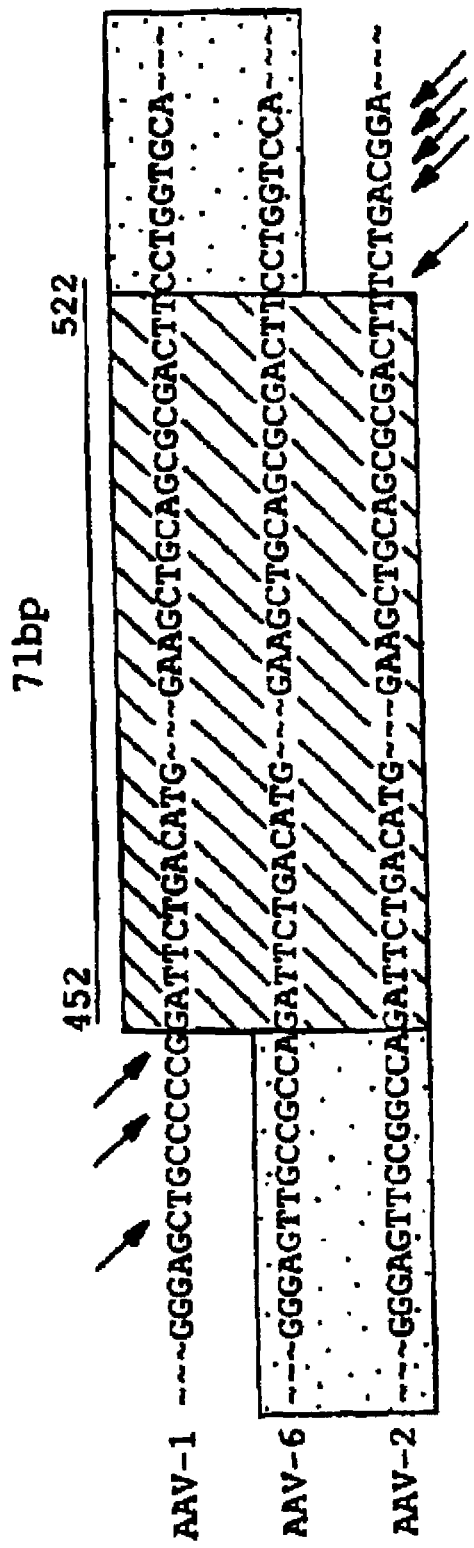
FIG. 3B is a detailed illustration of a 71 bp homologous region among AAV-1 (438-531 of SEQ ID NO:1), AAV-2 (424-513 of SEQ ID NO:18) and AAV-6 (423-512 of SEQ ID NO:19). Nucleotides that differ among these serotypes are indicated by arrows.

The AAV-1 genome exhibited similarities to other serotypes of adeno-associated viruses. Overall, it shares more than 80% identity with other known AAV viruses as determined by the computer program Megalign using default settings [DNASTAR, Madison, Wis.]. The key features in AAV-2 can also be found in AAV-1. First, AAV-1 has the same type of inverted terminal repeat which is capable of forming T-shaped hairpin structures, despite the differences at the nucleotide level (FIGS. 2 and 3). The sequences of right ITRs and left ITRs of AAV-1 are identical. The AAV TR sequence is subdivided into A, A', B, B', C, C', D and D' [Bern, cited above].

These AAV ITR sequences are also virtually the same as those found in AAV-6 right ITR, there being one nucleotide difference in each of A and A' sequence, and the last nucleotide of the D sequence. Second, the AAV-2 rep binding motif [GCTCGCTCGCTCGCTG (SEQ ID NO: 20)] is well conserved. Such motif can also be found in the human chromosome 19 AAV-2 pre-integration region. Finally, non-structural and structural coding regions, and regulatory elements similar to those of other AAV serotypes also exist in AAV-1 genome.

Although the overall features of AAV terminal repeats are very much conserved, the total length of the AAV terminal repeat exhibits divergence. The terminal repeat of AAV-1 consists of 143 nucleotides while those of AAV-2, AAV-3, and AAV-4 are about 145 or 146 nucleotides. The loop region of AAV-1 ITR most closely resembles that of AAV-4 in that it also uses TCT instead of the TTT found in AAV-2 and AAV-3. The possibility of sequencing error was eliminated using restriction enzyme digestion, since these three nucleotides are part of the SacI site (gagctc; nt 69-74 of SEQ ID NO: 1). The p5 promoter region of AAV-1 shows more variations in nucleotide sequences with other AAV serotypes. However, it still maintains the critical regulatory elements. The two copies of YY1 [See, FIGS. 1A-1F] sites seemed to be preserved in all known AAV serotypes, which have been shown to be involved in regulating AAV gene expression. In AAV-4, there are 56 additional nucleotides inserted between YY1 and E-box/USF site, while in AAV-1, there are 26 additional nucleotides inserted before the E-box/USF site. The p19 promoter, p40 promoter and polyA can also be identified from the AAV-1 genome by analogy to known AAV serotypes, which are also highly conserved.

Thus, the analysis of AAV terminal repeats of various serotypes showed that the A and A' sequence is very much conserved. One of the reasons may be the Rep binding motif $(GCTC)_3GCTG$ [SEQ ID NO: 20]. These sequences appear to be essential for AAV DNA replication and site-specific integration. The same sequence has also been shown to be preserved in a monkey genome [Samulski, personal communication]. The first 8 nucleotides of the D sequence are also identical in all known AAV serotypes. This is in accordance with the observation of the Srivastava group that only the first 10 nucleotides are essential for AAV packaging [X. S. Wang et al, *J. Virol.*, 71:3077-3082 (1997); X. S. Wang et al, *J. Virol.*, 71:1140-1146 (1997)]. The function of the rest of the D sequences still remain unclear. They may be somehow related to their tissue specificities. The variation of nucleotide in B and C sequence may also suggest that the secondary structure of the ITRs is more critical for its biological function, which has been demonstrated in many previous publications.

Example 3

Comparison of AAV-1 Sequences

The nucleotide sequences of AAV-1, obtained as described above, were compared with known AAV sequences, including AAV-2, AAV-4 and AAV-6 using DNA Star Megalign. This comparison revealed a stretch of 71 identical nucleotides shared by AAV-1, AAV-2 and AAV-6. See, FIGS. 1A-1F.

This comparison further suggested that AAV-6 is a hybrid formed by homologous recombination of AAV-1 and AAV-2. See, FIGS. 3A and 3B. These nucleotides divide the AAV-6 genome into two regions. The 5' half of AAV-6 of 522 nucleotides is identical to that of AAV-2 except in 2 positions. The 3' half of AAV-6 including the majority of the rep gene, complete cap gene and 3' ITR is 98% identical to AAV-1.

Biologically, such recombination may enable AAV-1 to acquire the ability to transmit through the human population. It is also interesting to note that the ITRs of AAV-6 comprise one AAV-1 ITR and one AAV-2 ITR. The replication model of defective parvovirus can maintain this special arrangement. Studies on AAV integration have shown that a majority of AAV integrants carries deletions in at least one of the terminal repeats. These deletions have been shown to be able to be repaired through gene conversion using the other intact terminal repeat as a template. Therefore, it would be very difficult to maintain AAV-6 as a homogenous population when an integrated copy of AAV-6 is rescued from host cells with helper virus infection. The AAV-6 with two identical AAV-2 ITRs or two identical AAV-1 ITRs should be the dominant variants. The AAV-6 with two AAV-1 ITRs has been observed by Russell's group [Rutledge, cited above (1998)]. So far there is no report on AAV-6 with two AAV-2 ITRs. Acquirement of AAV-2 P5 promoter by AAV-6 may have explained that AAV-6 have been isolated from human origin while AAV-1 with the same virion has not. The regulation of P5 promoter between different species of AAV may be different in vivo. This observation suggests the capsid proteins of AAV were not the only determinants for tissue specificity.

Although it is clear that AAV-6 is a hybrid of AAV-1 and AAV-2, AAV-6 has already exhibited divergence from either AAV-1 or AAV-2. There are two nucleotide differences between AAV-6 and AAV-2 in their first 450 nucleotides. There are about 1% differences between AAV-6 and AAV-1 in nucleotide levels from nucleotides 522 to the 3' end. There also exists a quite divergent region (nucleotide 4486-4593) between AAV-6 and AAV-1 (FIGS. 1A-1F). This region does not encode any known proteins for AAVs. These differences in nucleotide sequences may suggest that AAV-6 and AAV-1 have gone through some evolution since the recombination took place. Another possible explanation is that there exists another variant of AAV-1 which has yet to be identified. So far, there is no evidence to rule out either possibility. It is still unknown if other hybrids (AAV-2 to AAV-4, etc.) existed in nature.

The coding region of AAV-1 was deduced by comparison with other known AAV serotypes. Table 1 illustrates the coding region differences between AAV-1 and AAV-6. The amino acid residues are deduced according to AAV-2.

With reference to the amino acid position of AAV-1, Table 1 lists the amino acids of AAV-1 which have been changed to the corresponding ones of AAV-6. The amino acids of AAV-1 are shown to the left of the arrow. Reference may be made to SEQ ID NO: 5 of the amino acid sequence of AAV-1 Rep 78 and to SEQ ID NO: 13 for the amino acid sequence of AAV-1 VP1.

TABLE 1

Coding region variations between AAV-1 and AAV-6

| Rep protein (Rep78) | | Cap protein (VP1) | |
|---|---|---|---|
| Position(s) | Amino acids | Position(s) | Amino acids |
| 28 | S→N | 129 | L→F |
| 191 | Q→H | 418 | E→D |
| 192 | H→D | 531 | E→K |
| 308 | E→D | 584 | F→L |
| | | 598 | A→V |
| | | 642 | N→H |

It was surprising to see that the sequence of the AAV-1 coding region is almost identical to that of AAV-6 from position 452 to the end of coding region (99%). The first 508 nucleotides of AAV-6 have been shown to be identical to those of AAV-2 [Rutledge, cited above (1998)]. Since the components of AAV-6 genome seemed to be AAV-2 left ITR—AAV-2 p5 promoter—AAV-1 coding region—AAV-1 right ITR, it was concluded that AAV-6 is a naturally occurred hybrid between AAV-1 and AAV-2.

Example 4

Gene Therapy Vector Based on AAV-1

Recombinant gene transfer vectors based on AAV-1 viruses were constructed by the methods described in Example 1. To produce a hybrid recombinant virus with AAV-1 virion and AAV-2 ITR, the AAV-1 trans plasmid (pAV1H) and the AAV-2 cis-lacZ plasmid (with AAV-2 ITR) were used. The AAV-2 ITR was used in this vector in view of its known ability to direct site-specific integration. Also constructed for use in this experiment was an AAV-1 vector carrying the green fluorescent protein (GFP) marker gene under the control of the immediate early promoter of CMV using pAV1H as the trans plasmid.

A. rAAV-1 Viruses Transfect Host Cells In Vitro 84-31 cells, which are subclones of 293 cells (which express adenovirus E1a, E1b) which stably express E4/ORFS, were infected with rAAV-1 GFP or rAAV-lacZ. High levels of expression of GFP and lacZ was detected in the cultured 84-31 cells. This suggested that rAAV-1 based vector was very similar to AAV-2 based vectors in ability to infect and expression levels.

B. rAAV-1 Viruses Transfect Cells In Vivo

The performance of AAV-1 based vectors was also tested in vivo. The rAAV-1 CMV-α1AT virus was constructed as follows. The EcoRI fragment of pAT85 (ATCC) containing human α1-antitrypsin (α1AT) cDNA fragment was blunted and cloned into PCR (Promega) at a SmaI site to obtain PCR-α1AT. The CMV promoter was cloned into PCR-α1AT at the XbaI site. The Alb-α1AT expression cassette was removed by XhoI and ClaI and cloned into pAV1H at the XbaI site. This vector plasmid was used to generate AAV-1-CMV-α1AT virus used in the experiment described below.

For screening human antibodies against AAV, purified AAV virus is lysed with Ripa buffer (10 mM Tris pH 8.2, 1% Triton X-100, 1% SDS, 0.15 M NaCl) and separated in 10% SDS-PAGE gel. The heat inactivated human serum was used at a 1 to 1000 dilution in this assay. The rAAV-1 CMV-α1AT viruses were injected into Rag-1 mice through tail vein injection at different dosages. The concentration of human α1-antitrypsin in mouse serum was measured using ELISA. The coating antibody is rabbit anti-human human α1-antitrypsin (Sigma). The goat-antihuman α1-antitrypsin (Sigma) was used as the primary detection antibodies. The sensitivity of this assay is around 0.3 ng/ml to 30 ng/ml. The expression of human α1-antitrypsin in mouse blood can be detected in a very encouraging level. This result is shown in Table 2.

TABLE 2

Human α1-Antitrypsin Expressed in Mouse Liver

| Amount of virus injected | Week 2 (ng/ml) | Week 4 (ng/ml) |
|---|---|---|
| $2 \times 10^{10}$ genomes | 214.2 | 171.4 |
| $1 \times 10^{10}$ genomes | 117.8 | 109.8 |
| $5 \times 10^{10}$ genomes | 64.5 | 67.8 |
| $2.5 \times 10^{10}$ genomes | 30.9 | 58.4 | rAAV-1 CMV-lacZ viruses were also injected into the muscle of C57BL6 mice and similar results were obtained. Collectively, these results suggested that AAV-1 based vector would be appropriate for both liver and muscle gene delivery.

Example 5

Neutralizing Antibodies Against AAV-1

Simple and quantitative assays for neutralizing antibodies (NAB) to AAV-1 and AAV-2 were developed with recombinant vectors. A total of 33 rhesus monkeys and 77 normal human subjects were screened.

1. Nonhuman Primates

Wild-caught juvenile rhesus monkeys were purchased from Covance (Alice, Tex.) and LABS of Virginia (Yemassee, S.C.) and kept in full quarantine. The monkeys weighed approximately 3 to 4 kg. The nonhuman primates used in the Institute for Human Gene Therapy research program are purposefully bred in the United States from specific-pathogen-free closed colonies. All vendors are US Department of Agriculture class A dealers. The rhesus macaques are therefore not infected with important simian pathogens, including the tuberculosis agent, major simian lentiviruses (simian immunodeficiency virus and simian retroviruses), and cercopithecine herpesvirus. The animals are also free of internal and external parasites. The excellent health status of these premium animals minimized the potential for extraneous variables. For this study, serum was obtained from monkeys prior to initiation of any protocol.

NAB titers were analyzed by assessing the ability of serum antibody to inhibit the transduction of reporter virus expressing green fluorescent protein (GFP) (AAV1-GFP or AAV2-GFP) into 84-31 cells. Various dilutions of antibodies preincubated with reporter virus for 1 hour at 37° C. were added to 90% confluent cell cultures. Cells were incubated for 48 hours and the expression of green fluorescent protein was measured by Fluorolmaging (Molecular Dynamics). NAB titers were calculated as the highest dilution at which 50% of the cells stained green.

Analysis of NAB in rhesus monkeys showed that 61% of animals tested positive for AAV-1; a minority (24%) has NAB to AAV-2. Over one-third of animals had antibodies to AAV-1 but not AAV-2 (i.e., were monospecific for AAV-1), whereas no animals were positive for AAV-2 without reacting to AAV-1. These data support the hypothesis that AAV-1 is endemic in rhesus monkeys. The presence of true AAV-2 infections in this group of nonhuman primates is less clear, since cross-neutralizing activity of an AAV-1 response to AAV-2 can not be ruled out. It is interesting that there is a linear relationship between AAV-2 NAB and AAV-1 NAB in animals that had both.

2. Humans

For these neutralization antibody assays, human serum samples were incubated at 56° C. for 30 min to inactivate complement and then diluted in DMEM. The virus (rAAV or rAd with either lacZ or GFP) was then mixed with each serum dilution (20×, 400×, 2000×, 4000×, etc.) and incubated for 1 hour at 37° C. before applied to 90% confluent cultures of 84-31 cells (for AAV) or Hela cells (for adenovirus) in 96-well plates. After 60 minutes of incubation at culture condition, 100 µl additional media containing 20% FCS was added to make final culture media containing 10% FCS.

The results are summarized in Table 3.

TABLE 3

| Adenovirus | AAV-1 | AAV-2 | # of samples | Percentage |
|---|---|---|---|---|
| − | − | − | 41 | 53.2% |
| + | − | − | 16 | 20.8% |
| − | + | − | 0 | 0.0% |
| − | − | + | 2 | 2.6% |
| − | + | + | 2 | 2.6% |
| + | − | + | 3 | 3.9% |

TABLE 3-continued

| Adenovirus | AAV-1 | AAV-2 | # of samples | Percentage |
|---|---|---|---|---|
| + | + | − | 0 | 0.0% |
| + | + | + | 13 | 16.9% |
| | | Total | 77 | 100% |

The human neutralizing antibodies against these three viruses seemed to be unrelated since the existence of neutralizing antibodies against AAV are not indications for antibodies against adenovirus. However, AAV requires adenovirus as helper virus, in most of the cases, the neutralizing antibodies against AAV correlated with the existence of neutralizing antibodies to adenovirus. Among the 77 human serum samples screened, 41% of the samples can neutralize the infectivity of recombinant adenovirus based on Ad5. 15/77 (19%) of serum samples can neutralize the transduction of rAAV-1 while 20/77 (20%) of the samples inhibit rAAV-2 transduction at 1 to 80 dilutions or higher. All serum samples positive in neutralizing antibodies for AAV-1 in are also positive for AAV-2. However, there are five (6%) rAAV-2 positive samples that failed to neutralize rAAV-1. In samples that are positive for neutralizing antibodies, the titer of antibodies also varied in the positive ones. The results from screening human sera for antibodies against AAVs supported the conclusion that AAV-1 presents the same epitome as that of AAV-2 to interact with cellular receptors since AAV-1 neutralizing human serums can also decrease the infectivity of AAV-2. However, the profile of neutralizing antibodies for these AAVs is not identical, there are additional specific receptors for each AAV serotype.

Example 6

Recombinant AAV Viruses Exhibit Tissue Tropism

The recombinant AAV-1 vectors of the invention and the recombinant AAV-2 vectors [containing the gene encoding human α1-antitrypsin (α1AT) or murine erythropoietin (Epo) from a cytomegalovirus-enhanced β-actin promoter (CB)] were evaluated in a direct comparison to equivalent copies of AAV-2 vectors containing the same vector genes.

Recombinant viruses with AAV-1 capsids were constructed using the techniques in Example 1. To make rAAV with AAV-1 virions, pAV1H or p5E18 (2/1) was used as the trans plasmid to provide Rep and Cap functions. For the generation of the rAAV based on AAV-2, p5E18(2/2) was used as the trans plasmid, since it greatly improved the rAAV yield. [Early experiments indicated similar in vivo performances of AAV-1 vectors produced with pAV1H and p5E19 (2/1). All subsequent studies used AAV-1 vectors derived from p5E18(2/1) because of the increased yield.]

Figure 4A:
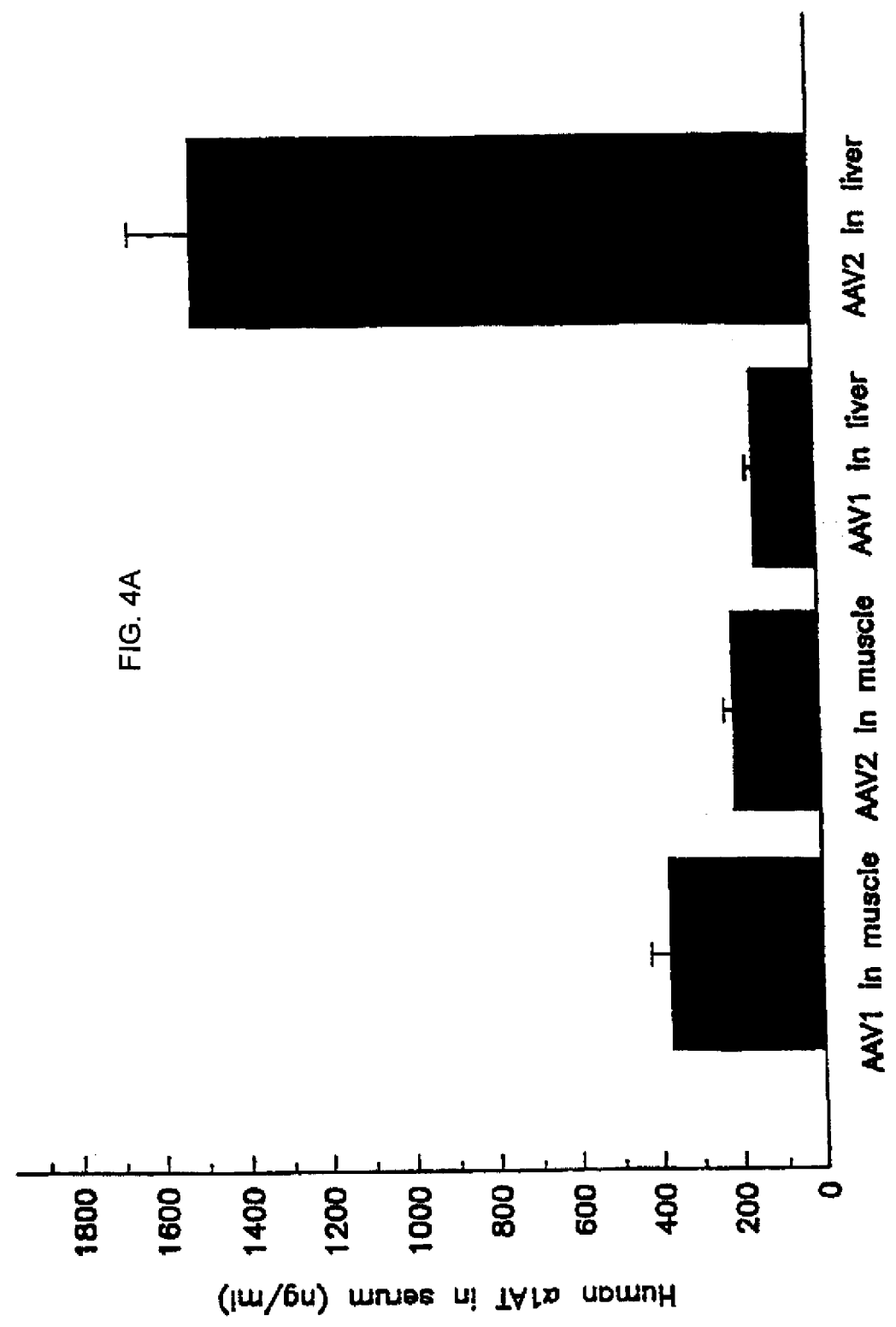
Figure 4B:
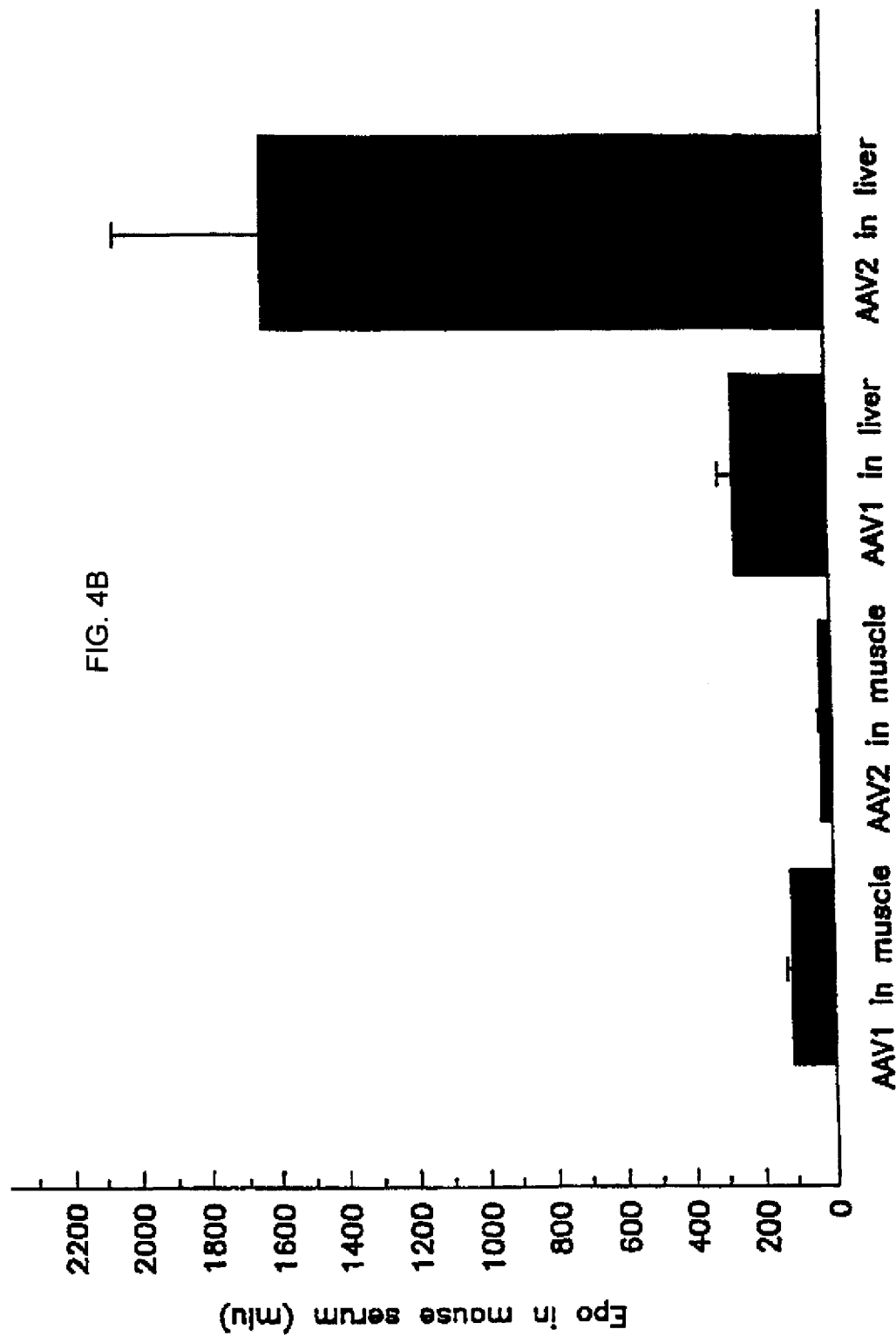
FIG. 4B is a bar chart illustrating expression levels of erythropoietin (epo) in serum following delivery of the epo gene via recombinant AAV-1 and recombinant AAV-2 viruses.
Figure 5A:
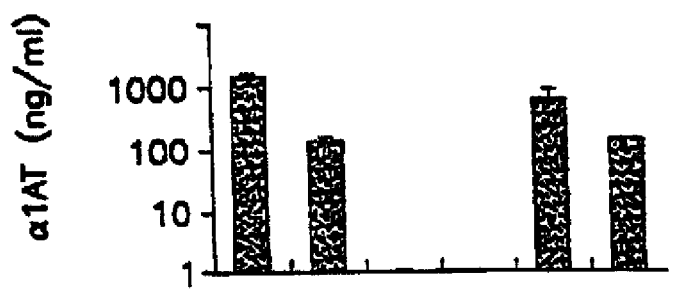
FIG. 5A is a bar chart illustrating expression levels of α1AT in liver following delivery of α1AT as described in Example 7.
Figure 5B:
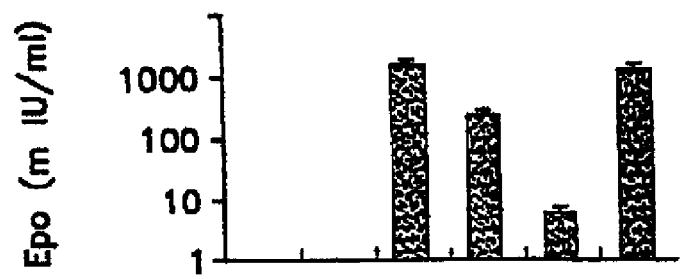
FIG. 5B is a bar chart demonstrating expression levels of epo in liver following delivery of epo as described in Example 7.
Figure 5C:
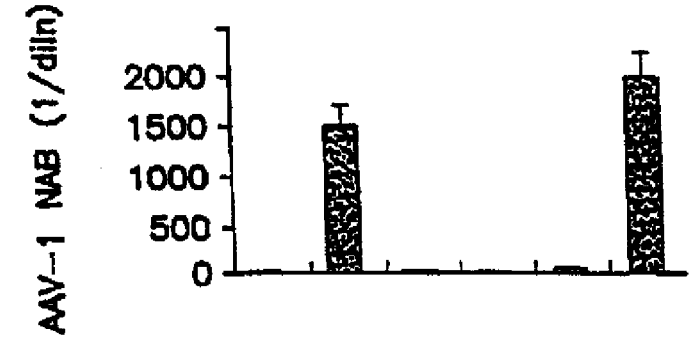
FIG. 5C is a bar chart demonstrating neutralizing antibodies (NAB) directed to AAV-1 following delivery of α1AT or epo to liver as described in Example 7.
Figure 5D:
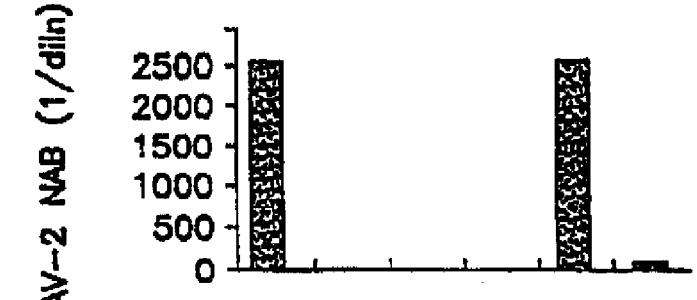
FIG. 5D is a bar chart demonstrating neutralizing antibodies (NAB) directed to AAV-2 following delivery of α1AT or epo to liver as described in Example 7.
Figure 6A:
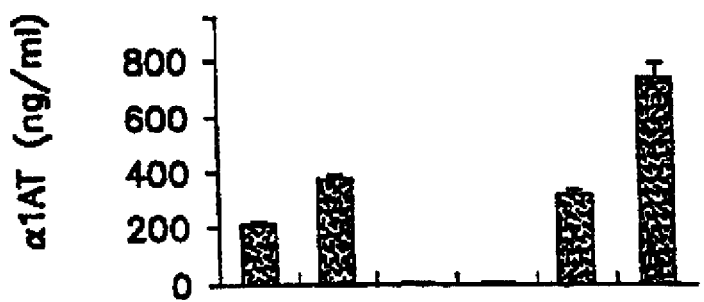
FIG. 6A is a bar chart illustrating expression levels of α1AT in muscle following delivery of α1AT as described in Example 7.
Figure 6B:
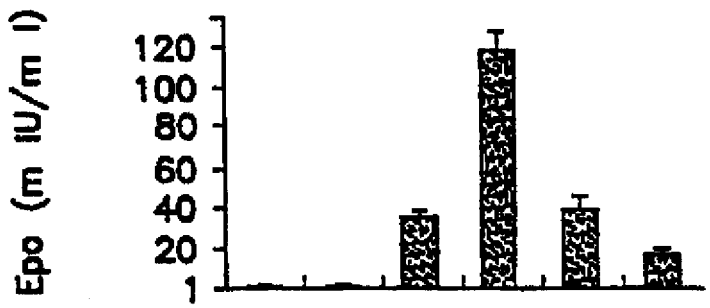
FIG. 6B is a bar chart demonstrating expression levels of epo in muscle following delivery of epo as described in Example 7.
Figure 6C:
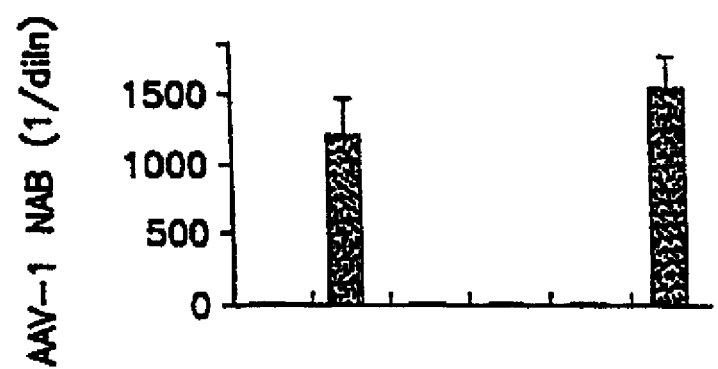
FIG. 6C is a bar chart demonstrating neutralizing antibodies (NAB) directed to AAV-1 following delivery of α1AT or epo to muscle as described in Example 7.
Figure 6D:
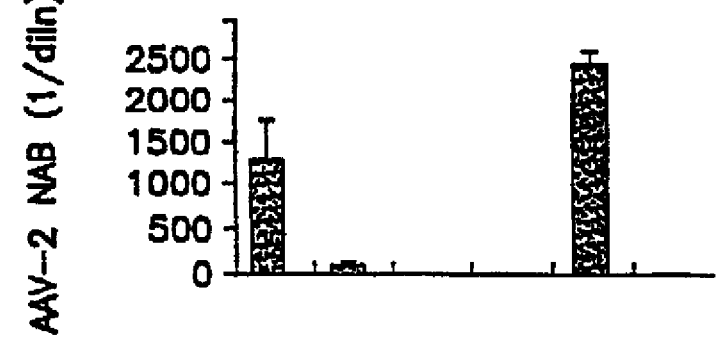
FIG. 6D is a bar chart demonstrating neutralizing antibodies (NAB) directed to AAV-2 following delivery of α1AT or epo to muscle as described in Example 7.

Equivalent stocks of the AAV-1 and AAV-2 vectors were injected intramuscularly ($5 \times 10^{10}$ genomes) or liver via the portal circulation ($1 \times 10^{11}$ genomes) into immunodeficient mice, and the animals (four groups) were analyzed on day 30 for expression of transgene. See, FIGS. 4A and 4B.

AAV-2 vectors consistently produced 10- to 50-fold more serum erythropoietin or α1-antitrypsin when injected into liver compared to muscle. (However, the AAV-1-delivered genes did achieve acceptable expression levels in the liver.) This result was very different from that for AAV-1 vectors, with which muscle expression was equivalent to or greater than liver expression. In fact, AAV-1 outperformed AAV-2 in muscle when equivalent titers based on genomes were administered.

Example 7

Gene Delivery Via rAAV-1

C57BL/6 mice (6- to 8-week old males, Jackson Laboratories) were analyzed for AAV mediated gene transfer to liver following intrasplenic injection of vector (i.e., targeted to liver). A total of $10^{11}$ genome equivalents of rAAV-1 or rAAV-2 vector were injected into the circulation in 100 µl buffered saline. The first vector contained either an AAV-1 capsid or an AAV-2 capsid and expressed α1AT under the control of the chicken β-actin (CB) promoter. Day 28 sera were analyzed for antibodies against AAV-1 or AAV-2 and serum α1AT levels were checked. Animals were then injected with an AAV-1 or AAV-2 construct expressing erythropoietin (Epo, also under the control of the CB promoter). One month later sera was analyzed for serum levels of Epo. The following groups were analyzed (FIGS. 5A-5D).

In Group 1, vector 1 was AAV-2 expressing α1AT and vector 2 was AAV-2 expressing Epo. Animals generated antibodies against AAV-2 following the first vector administration which prevented the readministration of the AAV-2 based vector. There was no evidence for cross-neutralizing the antibody to AAV-1.

In Group 2, vector 1 was AAV-1 expressing α1AT while vector 2 was AAV-1 expressing Epo. The first vector administration did result in significant α1AT expression at one month associated with antibodies to neutralizing antibodies to AAV-1. The animals were not successfully readministered with the AAV-1 Epo expressing construct.

In Group 3, the effectiveness of an AAV-2 vector expressing Epo injected into a naive animal was measured. The animals were injected with PBS and injected with AAV-2 Epo vector at day 28 and analyzed for Epo expression one month later. The neutralizing antibodies were evaluated at day 28 so we did not expect to see anything since they received PBS with the first vector injection. This shows that in naive animals AAV-2 is very efficient at transferring the Epo gene as demonstrated by high level of serum Epo one month later.

Group 4 was an experiment similar to Group 3 in which the animals originally received PBS for vector 1 and then the AAV-1 expressing Epo construct 28 days later. At the time of vector injection, there obviously were no antibodies to either AAV-1 or AAV-2. The AAV-1 based vector was capable of generating significant expression of Epo when measured one month later.

Group 5 is a cross-over experiment where the initial vector is AAV-2 expressing α1AT followed by the AAV-1 construct expressing Epo. The animals, as expected, were efficiently infected with the AAV-2 vector expressing α1AT as shown by high levels of the protein in blood at 28 days. This was associated with significant neutralizing antibodies to AAV-2. Importantly, the animals were successfully administered AAV-1 following the AAV-2 vector as shown by the presence of Epo in serum 28 days following the second vector administration. At the time of this vector administration, there was high level AAV-2 neutralizing antibodies and very low cross-reaction to AAV-1. The level of Epo was slightly diminished possibly due to a small amount of cross-reactivity. Group 6 was the opposite cross-over experiment in which the initial vector was AAV-1 based, whereas the second experiment was AAV-2 based. The AAV-1 vector did lead to significant gene expression of α1AT, which also resulted in high level AAV-1 neutralizing antibody. The animals were very efficiently administered AAV-2 following the initial AAV-1 vector as evidenced by high level Epo.

A substantially identical experiment was performed in muscle in which $5\times10^{10}$ genomes were injected into the tibialis anterior of C57BL/6 mice as a model for muscle directed gene therapy. The results are illustrated in FIGS. 6A-6D and are essentially the same as for liver.

In summary, this experiment demonstrates the utility of using an AAV-1 vector in patients who have pre-existing antibodies to AAV-2 or who had initially received an AAV-2 vector and need readministration.

Example 8

Construction of Recombinant Viruses Containing AAV-1 ITRs

This example illustrates the construction of recombinant AAV vectors which contain AAV-1 ITRs of the invention.

An AAV-1 cis plasmid is constructed as follows. A 160 bp Xho-NruI AAV-1 fragment containing the AAV-1 5' ITR is obtained from pAV1-BL. pAV1-BL was generated as described in Example 1. The Xho-NruI fragment is then cloned into a second pAV1-BL plasmid at an XbaI site to provide the plasmid with two AAV-1 ITRs. The desired transgene is then cloned into the modified pAV-1BL at the NruI and BamHI site, which is located between the AAV-1 ITR sequences. The resulting AAV-1 cis plasmid contains AAV-1 ITRs flanking the transgene and lacks functional AAV-1 rep and cap.

Recombinant AAV is produced by simultaneously transfecting three plasmids into 293 cells. These include the AAV-1 cis plasmid described above; a trans plasmid which provides AAV rep/cap functions and lacks AAV ITRs; and a plasmid providing adenovirus helper functions. The rep and/or cap functions may be provided in trans by AAV-1 or another AAV serotype, depending on the immunity profile of the intended recipient. Alternatively, the rep or cap functions may be provided in cis by AAV-1 or another serotype, again depending on the patient's immunity profile.

In a typical cotransfection, 50 µg of DNA (cis:trans:helper at ratios of 1:1:2, respectively) is transfected onto a 15 cm tissue culture dish. Cells are harvested 96 hours post transfection, sonicated and treated with 0.5% sodium deoxycholate (37° for 10 min) Cell lysates are then subjected to 2-3 rounds of ultracentrifugation in a cesium gradient. Peak fractions containing rAAV are collected, pooled and dialyzed against PBS. A typical yield is $1\times10^{13}$ genomes/$10^9$ cells.

Using this method, one recombinant virus construct is prepared which contains the AAV-1 ITRs flanking the transgene, with an AAV-1 capsid. Another recombinant virus construct is prepared with contains the AAV-1 ITRs flanking the transgene, with an AAV-2 capsid.

All publications cited in this specification are incorporated herein by reference. While the invention has been described with reference to a particularly preferred embodiments, it will be appreciated that modifications can be made without departing from the spirit of the invention. Such modifications are intended to fall within the scope of the claims.

What is claimed is:

1. A recombinant virus having an AAV-1 capsid comprising a vp1 protein, a vp2 protein, and a vp3 protein, wherein said vp3 protein has an amino acid sequence of SEQ ID NO:17, wherein said recombinant virus further comprises a heterologous molecule which comprises an AAV 5' inverted terminal repeat sequence (ITR), a transgene, and an AAV 3' ITR.

2. The recombinant virus according to claim 1, wherein said vp1 protein has the amino acid sequence of SEQ ID NO: 13.

3. The recombinant virus according to claim 1, wherein said vp2 protein has the amino acid sequence of SEQ ID NO: 15.

4. The recombinant virus according to claim 1, wherein the 5' ITR and 3' ITR are of AAV serotype 2.

5. The recombinant virus according to claim 1, wherein the 5' ITR and 3' ITR are of AAV serotype 1.

6. The recombinant virus according to claim 1, further comprising a promoter which directs expression of the transgene.

7. The recombinant virus according to claim 1, wherein said transgene encodes a protein or peptide.

8. The recombinant virus according to claim 7, wherein said protein or peptide is a therapeutic protein or peptide.

9. The recombinant virus according to claim 7, wherein said protein or peptide is an immunogenic protein or peptide.

10. The recombinant virus according to claim 1, wherein said transgene encodes a cytokine, a hormone, or a growth factor.

11. The recombinant virus according to claim 1, wherein said transgene is alpha 1 anti-trypsin (α1AT).

12. The recombinant virus according to claim 1, wherein said transgene is erythropoietin (epo).

13. An isolated host cell transformed with the recombinant virus of claim 1.

14. A composition comprising a recombinant virus according to claim 1 and a pharmaceutically acceptable carrier.

15. The composition according to claim 14, wherein said composition is formulated for delivery to muscle.

16. The composition according to claim 14, wherein said composition is formulated for delivery to liver.

17. The composition according to claim 14, wherein said composition is formulated for intranasal delivery.

* * * * *

UNITED STATES PATENT AND TRADEMARK OFFICE
CERTIFICATE OF CORRECTION

PATENT NO. : 9,567,607 B2
APPLICATION NO. : 14/849722
DATED : February 14, 2017
INVENTOR(S) : James M. Wilson and Weidong Xiao Page 1 of 1

It is certified that error appears in the above-identified patent and that said Letters Patent is hereby corrected as shown below:

In the Specification

Column 1, Line 40, the paragraph immediately following the heading "STATEMENT REGARDING FEDERALLY SPONSORED RESEARCH OR DEVELOPMENT" is replaced with the following paragraph:
-- This invention was made with government support under DK047757 and HD036649 awarded by the National Institutes of Health. The government has certain rights in the invention. --

Signed and Sealed this
Fifteenth Day of October, 2019

Andrei Iancu
*Director of the United States Patent and Trademark Office*